(12) United States Patent
Henriksen et al.

(10) Patent No.: US 11,780,910 B1
(45) Date of Patent: Oct. 10, 2023

(54) ANTI-ANGPTL3 ANTIBODIES SUITABLE FOR HIGH CONCENTRATION COMPOSITIONS AND SUBCUTANEOUS ADMINISTRATION

(71) Applicant: Novo Nordisk A/S, Bagsvaerd (DK)

(72) Inventors: Anette Henriksen, Alleroed (DK); Thomas Nylandsted Krogh, Jyllinge (DK); Per J. Greisen, Belmont, MA (US); Thomas Egebjerg, Ganloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 18/142,242

(22) Filed: May 2, 2023

(30) Foreign Application Priority Data

May 2, 2022 (EP) .................................... 22171090
Oct. 13, 2022 (EP) .................................... 22201248

(51) Int. Cl.
| | |
|---|---|
| *A61K 39/395* | (2006.01) |
| *A61K 39/00* | (2006.01) |
| *C07K 16/00* | (2006.01) |
| *C07K 16/46* | (2006.01) |
| *C07K 16/22* | (2006.01) |
| *A61P 3/10* | (2006.01) |

(52) U.S. Cl.
CPC ............... *C07K 16/22* (2013.01); *A61P 3/10* (2018.01); *A61K 2039/505* (2013.01); *C07K 2317/35* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,834,871 B2 | 9/2014 | Ober | |
| 9,951,127 B2 * | 4/2018 | Sleeman | A61P 3/00 |
| 10,618,965 B2 | 4/2020 | Igawa et al. | |
| 10,766,960 B2 | 9/2020 | Igawa et al. | |
| 10,919,953 B2 | 2/2021 | Katada et al. | |
| 11,267,868 B2 | 3/2022 | Mimoto et al. | |
| 2003/0078385 A1 | 4/2003 | Arathoon et al. | |
| 2003/0190311 A1 | 10/2003 | Dall'Acqua et al. | |
| 2014/0199294 A1 | 7/2014 | Mimoto et al. | |
| 2020/0093939 A1 | 3/2020 | Danos et al. | |

FOREIGN PATENT DOCUMENTS

| | | |
|---|---|---|
| EP | 4095157 | 1/2021 |
| WO | 9108298 A2 | 6/1991 |
| WO | 199627011 A1 | 9/1996 |
| WO | 1998005043 A1 | 2/1998 |
| WO | 98/50431 A2 | 11/1998 |
| WO | 08073300 A2 | 6/2008 |
| WO | 11014469 A1 | 2/2011 |
| WO | 2012115241 A1 | 8/2012 |
| WO | 12174178 A1 | 12/2012 |
| WO | 2013002362 A1 | 1/2013 |
| WO | 2014030728 A1 | 2/2014 |
| WO | 2014104165 A1 | 7/2014 |
| WO | 2014163101 A1 | 10/2014 |
| WO | 2016098357 A1 | 6/2016 |
| WO | 2016125495 A1 | 8/2016 |
| WO | 2017104783 A1 | 6/2017 |
| WO | 17142832 A1 | 8/2017 |
| WO | 17189813 A1 | 11/2017 |
| WO | 2020243031 A1 | 12/2020 |
| WO | 2021147984 A1 | 7/2021 |

OTHER PUBLICATIONS

Ahmad et al., "Inhibition of Angiopoietin-Like Protein 3 With a Monoclonal Antibody Reduces Triglycerides in Hypertriglyceridemia", Circulation, Jun. 27, 2019, vol. 140, No. 6, pp. 470-486.
Anonymous, "BetterBet(TM) Anti-ANGPTL3 Recycling Antibody", Creative Biolabs DCC Antibody, Dec. 2022, retrieved Dec. 16, 2022 from https://adcc.creative-biolabs.com/betterbet-anti-angptl3-recycling-antibody-6678.htm.
Anonymous: "BetterBet(TM) Anti-ANGPTL3, a Fc[gamma]RIIB Binding Enhanced Antibody" Creative Biolabs DCC Antibody, Dec. 2022, retrieved Dec. 16, 2022 from https://adcc.creative-biolabs.com/betterbet-anti-angptl3-a-fc-riib-binding-enhanced-antibody-6990.htm.
Casipit et al., "Improving the binding affinity of an antibody using molecular modeling and site-directed mutagenesis", Protein Science, Aug. 1998, vol. 7, pp. 1671-1680.
Chien et al., "Significant Structural and Functional Change of an Antigen-Binding Site by a Distant Amino Acid Substitution: Proposal of a Structural Mechanism," Proc. Natl. Acad. Sci., Jul. 1989, vol. 86, No. 14, pp. 5532-5536.
Conklin et al., "Identification of a mammalian angiopoietin-related protein expressed specifically in liver." Genomics, Dec. 1999, vol. 62, No. 3, pp. 477-482.
Connolly, "Analytical molecular surface calculation", J. Appl. Cryst., 1983, vol. 16, pp. 548-558.
Dall'Acqua et al., "Properties of Human IgG1s Engineered for Enhanced Binding ito the Neonatal Fe Receptor (FcRn)," Journal of Biological Chemistry, Aug. 2006, vol. 281, No. 33, p. 23514-23524.
De Nardis et al., "A new approach for generating bispecific antibodies based on a common light chain format and the stable architecture of human immunoglobulin G1", J. Biol. Chem., Sep. 2017, vol. 292, pp. 14706-14717.

(Continued)

*Primary Examiner* — Maher M Haddad
(74) *Attorney, Agent, or Firm* — Jianjie Hu

(57) ABSTRACT

The present invention relates to novel monovalent anti-ANGPTL3 antibodies for use in medicine and in particular for lowering of plasma triglycerides levels in patients in need thereof, such as patients suffering from or at risk of hypertriglyceridemia and/or cardiovascular disease, such as atherosclerotic cardiovascular disease (ASCVD) as well as pharmaceutical compositions suitable for subcutaneous administration and kits comprising such compounds and compositions.

24 Claims, 18 Drawing Sheets

Specification includes a Sequence Listing.

(56) References Cited

OTHER PUBLICATIONS

Edelman et al., "The covalent structure of an entire gammaG immunoglobulin molecule", Proc. Natl. Acad. Sci. USA, May 1969, vol. 63, pp. 78-85.
Ghetie et al., "Increasing the Serum Persistence of an IgG Fragment by Random Mutagenesis," Nature Biotechnology, Jul. 1997, vol. 15, No. 7, pp. 637-640.
Glockshuber et al., "Mapping and modification of an antibody hapten binding site: a site-directed mutagenesis study of McPC603", Biochemistry, Mar. 26, 1991, vol. 30, No. 12, pp. 3049-3054.
Hinton et al., "An Engineered Human IgG1 Antibody with Longer Serum Half-Life", The Journal of immunology, Jan. 2006, vol. 176, pp. 346-356.
Hu et al., "A novel nanobody-heavy chain antibody against Angiopoietin-like protein 3 reduces plasma lipids and relieves nonalcoholic fatty liver disease", Research Square, Jan. 2022, pp. 1-29.
Igawa et al., "Sweeping antibody as a novel therapeutic antibody modality capable of eliminating soluble antigens from circulation", Immunol. Rev., Mar. 2016, vol. 270, pp. 132-151.
Kanai et al., "Reversible self-association of a concentrated monoclonal antibody solution mediated by Fab-Fab interaction that impacts solution viscosity", Journal of Pharmaceutical Sciences, Jan. 2008, vol. 97, No. 10, pp. 4219-4227.
Kobayashi et al., "Tryptophan H33 Plays an Important Role in Pyrimidine (6-4) Pyrimidine Photoproduct Binding by a High-Affinity Antibody," Protein Engineering, Jan. 1999, vol. 12, No. 10, pp. 879-844.
Kobrin et al., "A V region mutation in a phosphocholine-binding monoclonal antibody results in loss of antigen binding", Journal of Immunology, Mar. 1991, vol. 146, No. 6, pp. 2017-2020.
Labrijn et al., "Efficient generation of stable bispecific IgG1 by controlled Fab-arm exchange", PNAS USA, Mar. 2013, vol. 110, pp. 5145-5150.
Lee et al., "Identification of a New Functional Domain in Angiopoietin-like 3 (ANGPTL3) and Angiopoietin-like 4 (ANGPTL4) Involved in Binding and Inhibition of Lipoprotein Lipase (LPL)", The Journal of Biological Chemistry, May 15, 2009, vol. 284, No. 20, pp. 13735-13745.
Lee et al., "The interpretation of protein structures: estimation of static accessibility", J. Mol. Biol., Feb. 1971, vol. 65, pp. 379-400.
Li et al., "Triglyceride metabolism and angiopoietin-like proteins in lipoprotein lipase regulation", Clin. Chim. Acta, Jan. 2020, vol. 503, pp. 19-34.
Mackness et al., "Antibody Fc engineering for enhanced neonatal Fc receptor binding and prolonged circulation half-life", MAbs, Oct. 2019, vol. 11, pp. 1276-1288.
Merchant et al., "Monovalent antibody design and mechanism of action of onartuzumab, a MET antagonist with anti-tumor activity as a therapeutic agent", PNAS USA, Aug. 2013, vol. 110, pp. E2987-2996.
Needleman et al., "A general method applicable to the search for similarities in the amino acid sequence of two proteins", Journal of Molecular Biology, Mar. 1970, vol. 48, No. 3, pp. 443-453.
Ono et al., "Protein Region Important for Regulation of Lipid Metabolism in Angiopoietin-like 3 (ANGPTL3): ANGPTL3 is Cleaved and Activated in Vivo", Journal of Biological Chemistry, Oct. 2003, vol. 278, No. 43, p. 41804-41809.
Opolka-Hoffmann et al., "The impact of immunogenicity on therapeutic antibody pharmacokinetics: A preclinical evaluation of the effect of immune complex formation and antibody effector function on clearance", mAbs, Nov. 11, 2021, vol. 13, No. 1, pp. 1-12.
Pacios, "ARVOMOL/CONTOUR: Molecular surface areas and volumes on personal computers", Comput. Chem., 1994, vol. 18, No. 4, pp. 377-386.
Pacios,"Variations of Surface Areas and volumes in Distinct Molecular Surfaces of Biomolecules", Mol. Model. Annual, May 1995, vol. 1, pp. 46-53.
Panka et al., "Defining the structural correlates responsible for loss of arsonate affinity in an IdCR antibody isolated from an autoimmune mouse", Molecular Immunology, Aug. 1993, vol. 30 No. 11, pp. 1013-1020.
Petkova et al., "Enhanced half-life of genetically engineered human IgG1 antibodies in a humanized FcRn mouse model: potential application in humorally mediated autoimmune disease," International Immunology, Dec. 2006, vol. 18, pp. 1759-1769.
Raal et al., "Evinacumab for Homozygous Familial Hypercholesterolemia", NEJM, Aug. 2020, vol. 383, pp. 711-720.
Rudikoff et al., "Single amino acid substitution altering antigen-binding specificity," PNAS, Mar. 1982, vol. 79, pp. 1979-1983.
Schildbach et al.,"Modulation of antibody affinity by a non-contact residue", Protein Science, Feb. 1993, vol. 2, No. 2, pp. 206-214.
Shiraiwa et al., "Engineering a bispecific antibody with a common light chain: Identification and optimization of an anti-CD3 epsilon and anti-GPC3 bispecific antibody, ERY974", Methods, Feb. 2019, vol. 154, pp. 10-20.
St. Clair et al., "Immunogenicity of Isogenic IgG in Aggregates and Immune Complexes", PLOS ONE, Jan. 23, 2017, pp. 1-22.
Winkler et al., "Changing the Antigen Binding Specificity by Single Point Mutations of an Anti-p24 (HIV-1) Antibody," The Journal of Immunology, Oct. 15, 2000, vol. 165, No. 8, pp. 4505-4514.
Yamaguchi et al., "Pharmacology and Pharmacokinetics of NXT007; Emicizumab-Based; Engineered Fixa/Fx Bispecific Antibody with Improved Properties", Blood, Nov. 2020, vol. 136, Supplement 1, No. 19, pp. 1-3.
Zalevsky et al., "Enhanced antibody half-life improves in vivo activity", Nat. Biotechnol., Jan. 2010, vol. 28, pp. 157-159.
Zheng et al., "Translational pharmacokinetics and pharmacodynamics of an FcRn-variant anti-CD4 monoclonal antibody from preclinical model to phase I study", Clin. Pharm. & Ther., Dec. 2010, vol. 89, No. 2, pp. 283-290.

\* cited by examiner

FIG. 1A

| | CDR-, variable domain- and full-length sequences of tmAb1 | | | | | | |
|---|---|---|---|---|---|---|---|
| | | SEQ ID NO | CDR1 | SEQ ID NO | CDR2 | SEQ ID NO | CDR3 | SEQ ID NO |
| VH | EVQLLESGGGLVQPGGSLRL SCAASGFNFRSYWMTWVRQ APGKGLEWVSSISSHSTYIYY ADSVKGRFTISRDNSKNTLYL QMNSLRAEDTATYYCAREG WYDNWFDPWGQGTLVTVSS | 5 | SYWMT | 2 | SISSHSTYIYYADS VKG | 3 | EGWYDNWFD P | 4 |
| VL | EIVLTQSPGTLSLSPGERATL SCRASQNIRSPYLAWYQQKP GQAPRLLIYGVSSRAAGIPDR FSGSGSGTDFTLTISRLEPED FAVYYCQQYDDHPYTFGQG TKLEIK | 12 | RASQNIRSPY LA | 9 | GVSSRAA | 10 | QQYDDHPYT | 11 |
| HC des-(Gly-Lys) | EVQLLESGGGLVQPGGSLRLSCAASGFNFRSYWMTWVRQAPGKGLEWVSSISSHSTYIYYADSVKGRFTISRDNS KNTLYLQMNSLRAEDTATYYCAREGWYDNWFDPWGQGTLVTVSSASTKGPSVFPLAPSSKSTSGGTAALGCLVK DYFPEPVTVSWNSGALTSGVHTFPAVLQSSGLYSLSSVVTVPSSSLGTQTYICNVNHKPSNTKVDKKVEPKSCDKT HTCPPCPAPEYLGGPSVFLFPPKPKDVLTREPEVTCVVIDVSHEDPEVKFNWYVDGVEVHNAKTKPREEQYNST YRVVSVLTVLHQDWLNGKEYKCKVSNKALPAPIEKTISKAKGQPREPQVYTLPPSREEMTKNQVSLWCLVKGFYPS DIAVEWESNGQPENNYKTTPPVLDSDGSFFLYSKLTVDKSRWQQGNVFSCSVMHEALHNHYTQKSLSLSLSP | 6 | | | | | |
| tHC des-(Gly-Lys) | DKTHTCPPCPAPEYLGGDSVFLFPPKPKDVLTREPEVTCVVIDVSHEDPEVKFNWYVDGVEVHNAKTKPREEQY NSTYRVVSVLTVLHQDWLNGKEYKCKVSNKALPKPIEKTISKAKGQPREPQVYTLPPSREEMTKNQVSLSCAVKGF YPSDIAVEWESNGQPENNYKTTPPVLDSDGSFFLYSKLTVDKSRWQQGNVFSCSVMHEALHNHYTQKSLSLSP | 7 | | | | | |
| tHC (alternat.) | DKTHTCPPCPAPEYLGGDSVFLFPPKPKDVLTREPEVTCVVIDVSHEDPEVKFNWYVDGVEVHNAKTKPREEQY NSTYRVVSVLTVLHQDWLNGKEYKCKVSNKALPKPIEKTISKAKGQPREPQVYTLPPSREEMTKNQVSLSCAVKGF YPSDIAVEWESNGQPENNYKTTPPVLDSDGSFFLYSKLTVDKSRWQQGNVFSCSVMHEALHNHYTQKSLSLSPGK | 8 | | | | | |
| LC | EIVLTQSPGTLSLSPGERATLSCRASQNIRSPYLAWYQQKPGQAPRLLIYGVSSRAAGIPDRFSGSGSGTDFTLTISR LEPEDFAVYYCQQYDDHPYTFGQGTKLEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKSFNRGEC | 13 | | | | | |

FIG. 1B

| CDR-, variable domain- and full-length sequences of tmAb2 | | | | | | | |
|---|---|---|---|---|---|---|---|
| | SEQ ID NO | CDR1 | SEQ ID NO | CDR2 | SEQ ID NO | CDR3 | SEQ ID NO |
| VH | 17 | SYWMT | 14 | SISSHSTYIYYADSVKG | 15 | EGWYDNWFDP | 16 |
| | EVQLLESGGGLVQPGGSLRLSCAASDFNFRSYWMTWVRQAPGKGLEWVSSISSHSTYIYYADSVKGRFTISRDNSKNTLYLQMNSLRAEDTATYYCAREGWYDNWFDPWGQGTLVTVSS | | | | | | |
| VL | 12 | RASQNIRSPYLA | 9 | GVSSRAA | 10 | QQYDDHPYT | 11 |
| | EIVLTQSPGTLSLSPGERATLSCRASQNIRSPYLAWYQQKPGQAPRLLIYGVSSRAAGIPDRFSGSGSGTDFTLTISRLEPEDFAVYYCQQYDDHPYTFGQGTKLEIK | | | | | | |
| HC des-(Gly-Lys) | EVQLLESGGGLVQPGGSLRLSCAASDFNFRSYWMTWVRQAPGKGLEWVSSISSHSTYIYYADSVKGRFTISRDNSKNTLYLQMNSLRAEDTATYYCAREGWYDNWFDPWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEYLGGDSVFLFPPKPKDVLYITREPEVTCVVIDVSHEDPEVKFNWYVDGVEVHNAKTKPREEQYNSTYRVVSVLPVLHRDWLNGKEYKCKVSNKALPKPIEKTISKAKGQRREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSP | | 18 | | | | |
| tHC des-(Gly-Lys) | DKTHTCPPCPAPEYLGGDSVFLFPPKPKDVLYITREPEVTCVVIDVSHEDPEVKFNWYVDGVEVHNAKTKPREEQYNSTYRVVSVLPVLHRDWLNGKEYKCKVSNKALPKPIEKTISKAKGQRREPQVYTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSP | | 7 | | | | |
| tHC (alternat.) | DKTHTCPPCPAPEYLGGDSVFLFPPKPKDVLYITREPEVTCVVIDVSHEDPEVKFNWYVDGVEVHNAKTKPREEQYNSTYRVVSVLPVLHRDWLNGKEYKCKVSNKALPKPIEKTISKAKGQRREPQVYTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK | | 8 | | | | |
| LC | EIVLTQSPGTLSLSPGERATLSCRASQNIRSPYLAWYQQKPGQAPRLLIYGVSSRAAGIPDRFSGSGSGTDFTLTISRLEPEDFAVYYCQQYDDHPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | | 13 | | | | |

FIG. 1C

CDR-, variable domain- and full-length sequences of tmAb3

| | SEQ ID NO | CDR1 | SEQ ID NO | CDR2 | SEQ ID NO | CDR3 | SEQ ID NO |
|---|---|---|---|---|---|---|---|
| VH | 22 | SYWMT | 19 | SISSHSTYIYYADSVKG | 20 | EGWYDNWFDP | 21 |
| | | EVQLLESGGGLVQPGGSLRLSCAASGFNFESYWMTWVRQAPGKGLEWVSSISSHSTYIYYADSVKGRFTISRDNSKNTLYLQMNSLRAEDTATYYCAREGWYDNWFDPWGQGTLVTVSS | | | | | |
| VL | 12 | RASQNIRSPYLA | 9 | GVSSRAA | 10 | QQYDDHPYT | 11 |
| | | EIVLTQSPGTLSLSPGERATLSCRASQNIRSPYLAWYQQKPGQAPRLLIYGVSSRAAGIPDRFSGSGSGTDFTLTISRLEPEDFAVYYCQQYDDHPYTFGQGTKLEIK | | | | | |
| HC des-(Gly-Lys) | | EVQLLESGGGLVQPGGSLRLSCAASGFNFESYWMTWVRQAPGKGLEWVSSISSHSTYIYYADSVKGRFTISRDNSKNTLYLQMNSLRAEDTATYYCAREGWYDNWFDPWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEYLGGPSVFLFPPKPKDVLTIREPEVTCVVIDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSP | | | | | 23 |
| tHC des-(Gly-Lys) | | DKTHTCPPCPAPEYLGGDSVFLFPPKPKDVLMISRTPEVTCVVVDVSHEDPEVKFNWYVDGVEVHNAKTKPREEQYNSTYRVVSVLTVLHQDWLNGKEYKCKVSNKALPKPIEKTISKAKGQPREPQVYTLPPSREEMTKNQVSLSCAVKGFYPSDIAVEWESNGQPENNYKTTPPVLDSDGSFFLYSKLTVDKSRWQQGNVFSCSVMHEALHNHYTQKSLSLSP | | | | | 7 |
| tHC (alternat.) | | DKTHTCPPCPAPEYLGGDSVFLFPPKPKDVLMISRTPEVTCVVVDVSHEDPEVKFNWYVDGVEVHNAKTKPREEQYNSTYRVVSVLTVLHQDWLNGKEYKCKVSNKALPKPIEKTISKAKGQPREPQVYTLPPSREEMTKNQVSLSCAVKGFYPSDIAVEWESNGQPENNYKTTPPVLDSDGSFFLYSKLTVDKSRWQQGNVFSCSVMHEALHNHYTQKSLSLSPGK | | | | | 8 |
| LC | | EIVLTQSPGTLSLSPGERATLSCRASQNIRSPYLAWYQQKPGQAPRLLIYGVSSRAAGIPDRFSGSGSGTDFTLTISRLEPEDFAVYYCQQYDDHPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | | | | | 13 |

FIG. 1D

| | CDR-, variable domain- and full-length sequences of tmAb4 | | | | | | |
|---|---|---|---|---|---|---|---|
| | SEQ ID NO | CDR1 | SEQ ID NO | CDR2 | SEQ ID NO | CDR3 | SEQ ID NO |
| VH | EVQLLESGGGLVQPGGSLRLSC AASGFNFESYWMTWVRQAPGK GLEWVSSISSHSTYIYYADSVKG RFTISRDNSKNTLYLQMNSLRAE DTATYYCAREGWYDNWNDPW GQGTLVTVSS | 27 | SYWMT | 24 | SISSHSTYIYYADS VKG | 25 | EGWYDNWN DP | 26 |
| VL | EIVLTQSPGTLSLSPGERATLSC RASQNIRSPYLAWYQQKPGQA PRLLIYGVSSRAAGIPDRFSGSG SGTDFTLTISRLEPEDFAVYYCQ QYDDHPYTFGQGTKLEIK | 12 | RASQNIRSPY LA | 9 | GVSSRAA | 10 | QQYDDHPYT | 11 |
| HC des-(Gly-Lys) | EVQLLESGGGLVQPGGSLRLSCAASGFNFESYWMTWVRQAPGKGLEWVSSISSHSTYIYYADSVKGRFTISRDNSK NTLYLQMNSLRAEDTATYYCAREGWYDNWNDPWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICNVNHKPSNTKVDKKVEPKSCDKTHTC PPCPAPEYLGGDSVFLFPPKPKDVLYITREPEVTCVVIDVSHEDPEVKFNWYVDGVEVHNAKTKPREEQYNSTYRVV SVLPVLHRDWLNGKEYKCKVSNKALPKPIEKTISKAKGQPREPQVYTLPPSREEMTKNQVSLWCLVKGFYPSDIAVE WESNGQPENNYKTTPPVLDSDGSFFLYSKLTVDKSRWQQGNVFSCSVMHEALHNHYTQKSLSLSP | 28 | | | | | |
| tHC des-(Gly-Lys) | DKTHTCPPPCPAPEYLGGDSVFLFPPKPKDVLYITREPEVTCVVIDVSHEDPEVKFNWYVDGVEVHNAKTKPREEQYN STYRVVSVLPVLHRDWLNGKEYKCKVSNKALPKPIEKTISKAKGQRREPQVYTLPPSREEMTKNQVSLSCAVKGFYP SDIAVEWESNGQPENNYKTTPPVLDSDGSFFLVSKLTVDKSRWQQGNVFSCSVMHEALHNHYTQKSLSLSP | 7 | | | | | |
| tHC (alternat.) | DKTHTCPPPCPAPEYLGGDSVFLFPPKPKDVLYITREPEVTCVVIDVSHEDPEVKFNWYVDGVEVHNAKTKPREEQYN STYRVVSVLPVLHRDWLNGKEYKCKVSNKALPKPIEKTISKAKGQRREPQVYTLPPSREEMTKNQVSLSCAVKGFYP SDIAVEWESNGQPENNYKTTPPVLDSDGSFFLVSKLTVDKSRWQQGNVFSCSVMHEALHNHYTQKSLSLSPGK | 8 | | | | | |
| LC | EIVLTQSPGTLSLSPGERATLSCRASQNIRSPYLAWYQQKPGQAPRLLIYGVSSRAAGIPDRFSGSGSGTDFTLTISRL EPEDFAVYYCQQYDDHPYTFGQGTKLEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSFNRGEC | 13 | | | | | |

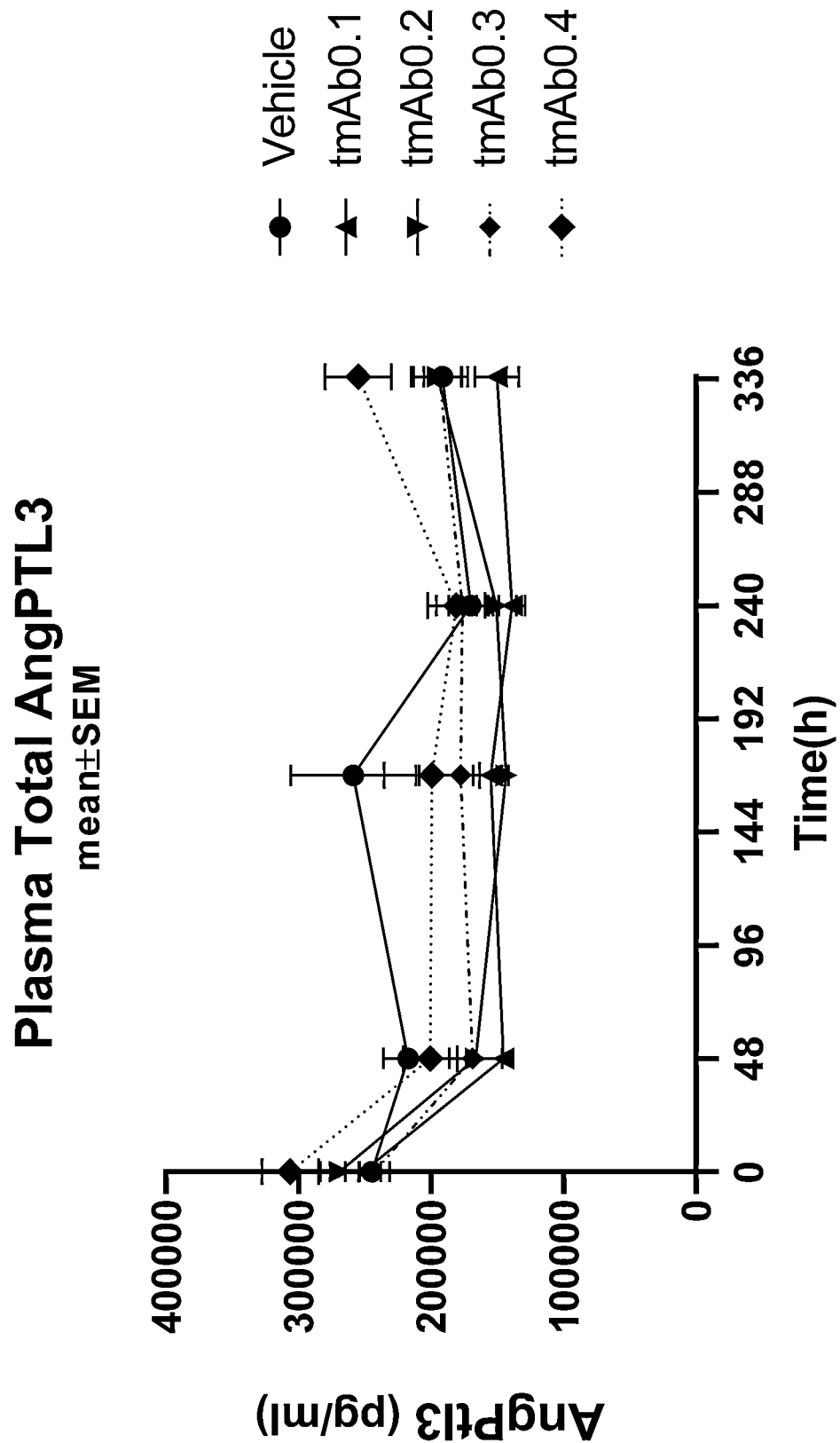

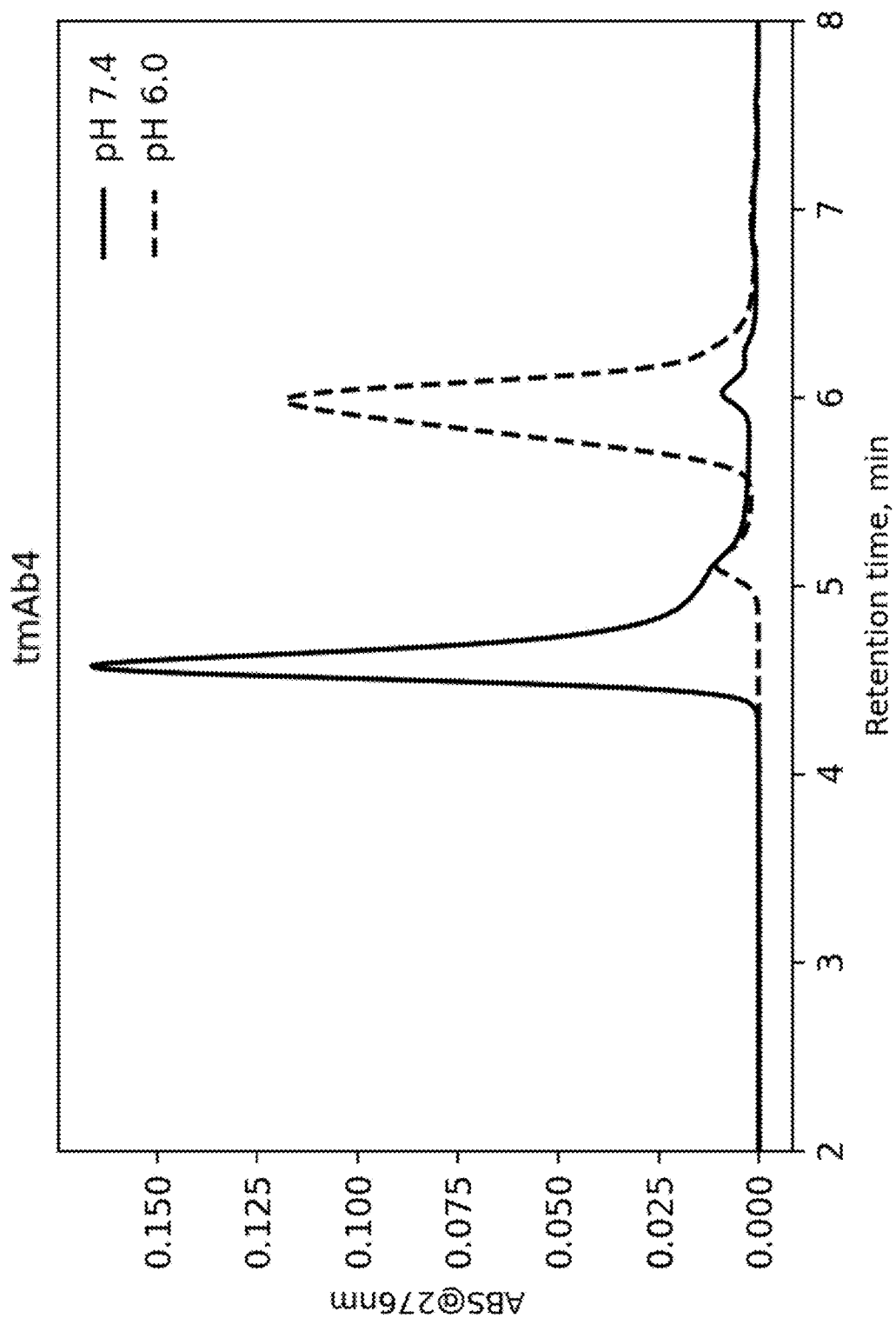

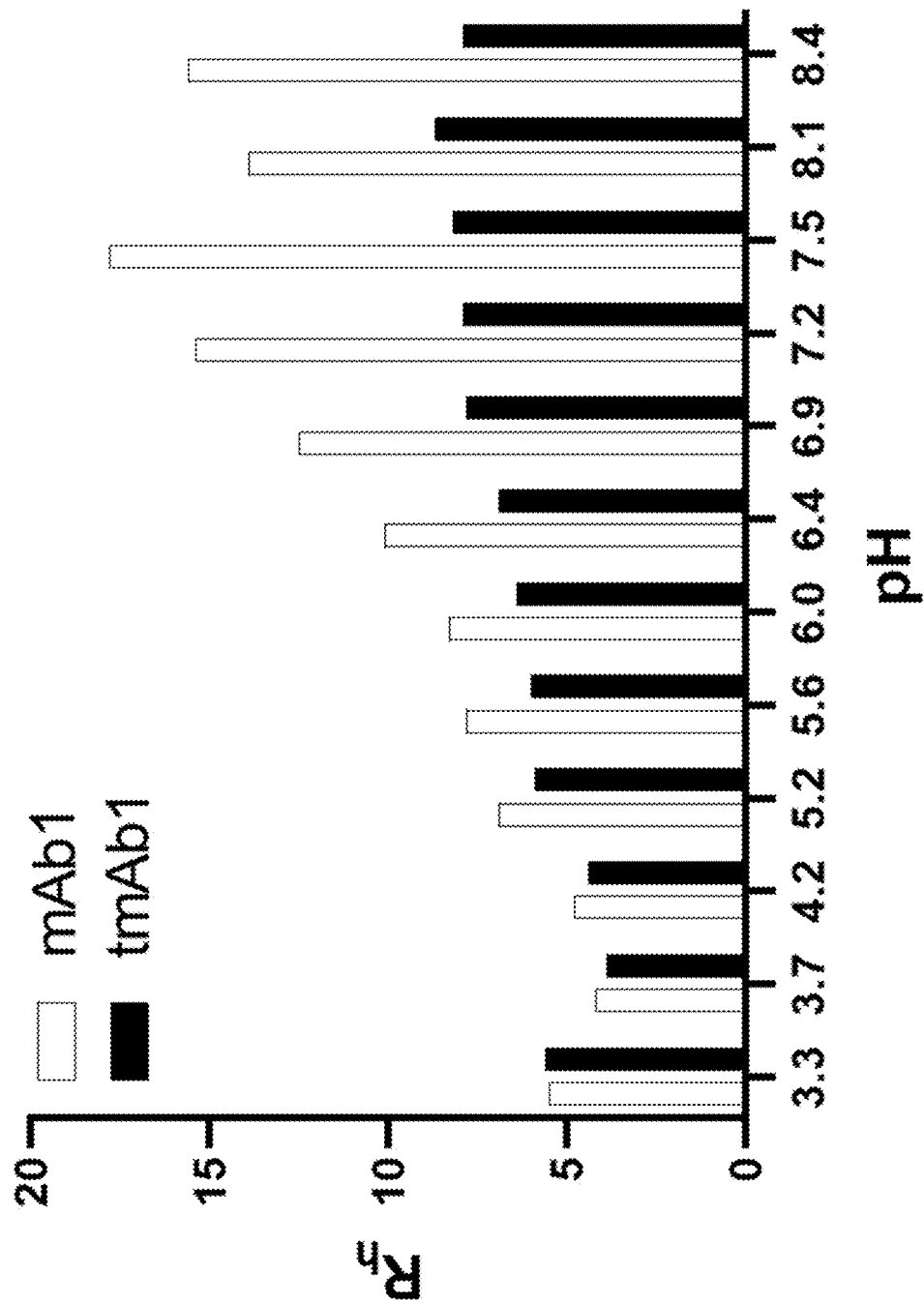

```
                               SEQUENCE LISTING

Sequence total quantity: 28
SEQ ID NO: 1            moltype = AA  length = 444
FEATURE                 Location/Qualifiers
source                  1..444
                        mol_type = protein
                        organism = Homo sapiens
SEQUENCE: 1
SRIDQDNSSF DSLSPEPKSR FAMLDDVKIL ANGLLQLGHG LKDFVHKTKG QINDIFQKLN  60
IFDQSFYDLS LQTSEIKEEE KELRRTTYKL QVKNEEVKNM SLELNSKLES LLEEKILLQQ  120
KVKYLEEQLT NLIQNQPETP EHPEVTSLKT FVEKQDNSIK DLLQTVEDQY KQLNQQHSQI  180
KEIENQLRRT SIQEPTEISL SSKPRAPRTT PFLQLNEIRN VKHDGIPAEC TTIYNRGEHT  240
SGMYAIRPSN SQVFHVYCDV ISGSPWTLIQ HRIDGSQNFN ETWENYKYGF GRLDGEFWLG  300
LEKIYSIVKQ SNYVLRIELE DWKDNKHYIE YSFYLGNHET NYTLHLVAIT GNVPNAIPEN  360
KDLVFSTWDH KAKGHFNCPE GYSGGWWWHD ECGENNLNGK YNKPRAKSKP ERRRGLSWKS  420
QNGRLYSIKS TKMLIHPTDS ESFE                                        444

SEQ ID NO: 2            moltype = AA  length = 5
FEATURE                 Location/Qualifiers
source                  1..5
                        mol_type = protein
                        organism = Synthetic construct
SEQUENCE: 2
SYWMT                                                              5

SEQ ID NO: 3            moltype = AA  length = 17
FEATURE                 Location/Qualifiers
source                  1..17
                        mol_type = protein
                        organism = Synthetic construct
SEQUENCE: 3
SISSHSTYIY YADSVKG                                                 17

SEQ ID NO: 4            moltype = AA  length = 10
FEATURE                 Location/Qualifiers
source                  1..10
                        mol_type = protein
                        organism = Synthetic construct
SEQUENCE: 4
EGWYDNWFDP                                                         10

SEQ ID NO: 5            moltype = AA  length = 119
FEATURE                 Location/Qualifiers
source                  1..119
                        mol_type = protein
                        organism = Synthetic construct
SEQUENCE: 5
EVQLLESGGG LVQPGGSLRL SCAASGFNFR SYWMTWVRQA PGKGLEWVSS ISSHSTYIYY  60
ADSVKGRFTI SRDNSKNTLY LQMNSLRAED TATYYCAREG WYDNWFDPWG QGTLVTVSS   119
```

```
SEQ ID NO: 6              moltype = AA  length = 447
FEATURE                   Location/Qualifiers
source                    1..447
                          mol_type = protein
                          organism = Synthetic construct
SEQUENCE: 6
EVQLLESGGG LVQPGGSLRL SCAASGFNFR SYWMTWVRQA PGKGLEWVSS ISSHSTYIYY   60
ADSVKGRFTI SRDNSKNTLY LQMNSLRAED TATYYCAREG WYDNWFDPWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEYLGGD  240
SVFLFPPKPK DVLYITREPE VTCVVIDVSH EDPEVKFNWY VDGVEVHNAK TKPREEQYNS  300
TYRVVSVLPV LHRDWLNGKE YKCKVSNKAL PKPIEKTISK AKGQRREPQV YTLPPSREEM  360
TKNQVSLWCL VKGFYPSDIA VEWESNGQPE NNYKTTPPVL DSDGSFFLYS KLTVDKSRWQ  420
QGNVFSCSVM HEALHNHYTQ KSLSLSP                                     447

SEQ ID NO: 7              moltype = AA  length = 225
FEATURE                   Location/Qualifiers
source                    1..225
                          mol_type = protein
                          organism = Synthetic construct
SEQUENCE: 7
DKTHTCPPCP APEYLGGDSV FLFPPKPKDV LYITREPEVT CVVIDVSHED PEVKFNWYVD   60
GVEVHNAKTK PREEQYNSTY RVVSVLPVLH RDWLNGKEYK CKVSNKALPK PIEKTISKAK  120
GQRREPQVYT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSP                 225

SEQ ID NO: 8              moltype = AA  length = 227
FEATURE                   Location/Qualifiers
source                    1..227
                          mol_type = protein
                          organism = Synthetic construct
SEQUENCE: 8
DKTHTCPPCP APEYLGGDSV FLFPPKPKDV LYITREPEVT CVVIDVSHED PEVKFNWYVD   60
GVEVHNAKTK PREEQYNSTY RVVSVLPVLH RDWLNGKEYK CKVSNKALPK PIEKTISKAK  120
GQRREPQVYT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 9              moltype = AA  length = 12
FEATURE                   Location/Qualifiers
source                    1..12
                          mol_type = protein
                          organism = Synthetic construct
SEQUENCE: 9
RASQNIRSPY LA                                                      12

SEQ ID NO: 10             moltype = AA  length = 7
FEATURE                   Location/Qualifiers
source                    1..7
                          mol_type = protein
                          organism = Synthetic construct
SEQUENCE: 10
GVSSRAA                                                             7

SEQ ID NO: 11             moltype = AA  length = 9
FEATURE                   Location/Qualifiers
source                    1..9
                          mol_type = protein
                          organism = Synthetic construct
SEQUENCE: 11
QQYDDHPYT                                                           9

SEQ ID NO: 12             moltype = AA  length = 108
FEATURE                   Location/Qualifiers
source                    1..108
                          mol_type = protein
                          organism = Synthetic construct
SEQUENCE: 12
EIVLTQSPGT LSLSPGERAT LSCRASQNIR SPYLAWYQQK PGQAPRLLIY GVSSRAAGIP   60
DRFSGSGSGT DFTLTISRLE PEDFAVYYCQ QYDDHPYTFG QGTKLEIK               108

SEQ ID NO: 13             moltype = AA  length = 215
FEATURE                   Location/Qualifiers
source                    1..215
                          mol_type = protein
                          organism = Synthetic construct
SEQUENCE: 13
EIVLTQSPGT LSLSPGERAT LSCRASQNIR SPYLAWYQQK PGQAPRLLIY GVSSRAAGIP   60
DRFSGSGSGT DFTLTISRLE PEDFAVYYCQ QYDDHPYTFG QGTKLEIKRT VAAPSVFIFP  120
```

```
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                              215

SEQ ID NO: 14           moltype = AA  length = 5
FEATURE                 Location/Qualifiers
source                  1..5
                        mol_type = protein
                        organism = Synthetic construct
SEQUENCE: 14
SYWMT                                                                 5

SEQ ID NO: 15           moltype = AA  length = 17
FEATURE                 Location/Qualifiers
source                  1..17
                        mol_type = protein
                        organism = Synthetic construct
SEQUENCE: 15
SISSHSTYIY YADSVKG                                                   17

SEQ ID NO: 16           moltype = AA  length = 10
FEATURE                 Location/Qualifiers
source                  1..10
                        mol_type = protein
                        organism = Synthetic construct
SEQUENCE: 16
EGWYDNWFDP                                                           10

SEQ ID NO: 17           moltype = AA  length = 119
FEATURE                 Location/Qualifiers
source                  1..119
                        mol_type = protein
                        organism = Synthetic construct
SEQUENCE: 17
EVQLLESGGG LVQPGGSLRL SCAASDFNFR SYWMTWVRQA PGKGLEWVSS ISSHSTYIYY    60
ADSVKGRFTI SRDNSKNTLY LQMNSLRAED TATYYCAREG WYDNWFDPWG QGTLVTVSS    119

SEQ ID NO: 18           moltype = AA  length = 447
FEATURE                 Location/Qualifiers
source                  1..447
                        mol_type = protein
                        organism = Synthetic construct
SEQUENCE: 18
EVQLLESGGG LVQPGGSLRL SCAASDFNFR SYWMTWVRQA PGKGLEWVSS ISSHSTYIYY    60
ADSVKGRFTI SRDNSKNTLY LQMNSLRAED TATYYCAREG WYDNWFDPWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEYLGGD   240
SVFLFPPKPK DVLYITREPE VTCVVIDVSH EDPEVKFNWY VDGVEVHNAK TKPREEQYNS   300
TYRVVSVLPV LHRDWLNGKE YKCKVSNKAL PKPIEKTISK AKGQRREPQV YTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSP                                       447

SEQ ID NO: 19           moltype = AA  length = 5
FEATURE                 Location/Qualifiers
source                  1..5
                        mol_type = protein
                        organism = Synthetic construct
SEQUENCE: 19
SYWMT                                                                 5

SEQ ID NO: 20           moltype = AA  length = 17
FEATURE                 Location/Qualifiers
source                  1..17
                        mol_type = protein
                        organism = Synthetic construct
SEQUENCE: 20
SISSHSTYIY YADSVKG                                                   17

SEQ ID NO: 21           moltype = AA  length = 10
FEATURE                 Location/Qualifiers
REGION                  1..10
                        note = Artificial
source                  1..10
                        mol_type = protein
                        organism = synthetic construct
SEQUENCE: 21
EGWYDNWFDP                                                           10

SEQ ID NO: 22           moltype = AA  length = 119
FEATURE                 Location/Qualifiers
```

```
source                   1..119
                         mol_type = protein
                         organism = Synthetic construct
SEQUENCE: 22
EVQLLESGGG LVQPGGSLRL SCAASGFNFE SYWMTWVRQA PGKGLEWVSS ISSHSTYIYY    60
ADSVKGRFTI SRDNSKNTLY LQMNSLRAED TATYYCAREG WYDNWFDPWG QGTLVTVSS    119

SEQ ID NO: 23            moltype = AA   length = 447
FEATURE                  Location/Qualifiers
source                   1..447
                         mol_type = protein
                         organism = Synthetic construct
SEQUENCE: 23
EVQLLESGGG LVQPGGSLRL SCAASGFNFE SYWMTWVRQA PGKGLEWVSS ISSHSTYIYY    60
ADSVKGRFTI SRDNSKNTLY LQMNSLRAED TATYYCAREG WYDNWFDPWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEYLGGD   240
SVFLFPPKPK DVLYITREPE VTCVVIDVSH EDPEVKFNWY VDGVEVHNAK TKPREEQYNS   300
TYRVVSVLPV LHRDWLNGKE YKCKVSNKAL PKPIEKTISK AKGQRREPQV YTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSP                                      447

SEQ ID NO: 24            moltype = AA   length = 5
FEATURE                  Location/Qualifiers
source                   1..5
                         mol_type = protein
                         organism = Synthetic construct
SEQUENCE: 24
SYWMT                                                                5

SEQ ID NO: 25            moltype = AA   length = 17
FEATURE                  Location/Qualifiers
source                   1..17
                         mol_type = protein
                         organism = Synthetic construct
SEQUENCE: 25
SISSHSTYIY YADSVKG                                                  17

SEQ ID NO: 26            moltype = AA   length = 10
FEATURE                  Location/Qualifiers
source                   1..10
                         mol_type = protein
                         organism = Synthetic construct
SEQUENCE: 26
EGWYDNWNDP                                                          10

SEQ ID NO: 27            moltype = AA   length = 119
FEATURE                  Location/Qualifiers
source                   1..119
                         mol_type = protein
                         organism = Synthetic construct
SEQUENCE: 27
EVQLLESGGG LVQPGGSLRL SCAASGFNFE SYWMTWVRQA PGKGLEWVSS ISSHSTYIYY    60
ADSVKGRFTI SRDNSKNTLY LQMNSLRAED TATYYCAREG WYDNWNDPWG QGTLVTVSS    119

SEQ ID NO: 28            moltype = AA   length = 447
FEATURE                  Location/Qualifiers
source                   1..447
                         mol_type = protein
                         organism = Synthetic construct
SEQUENCE: 28
EVQLLESGGG LVQPGGSLRL SCAASGFNFE SYWMTWVRQA PGKGLEWVSS ISSHSTYIYY    60
ADSVKGRFTI SRDNSKNTLY LQMNSLRAED TATYYCAREG WYDNWNDPWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEYLGGD   240
SVFLFPPKPK DVLYITREPE VTCVVIDVSH EDPEVKFNWY VDGVEVHNAK TKPREEQYNS   300
TYRVVSVLPV LHRDWLNGKE YKCKVSNKAL PKPIEKTISK AKGQRREPQV YTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSP                                      447
```

ANTI-ANGPTL3 ANTIBODIES SUITABLE FOR HIGH CONCENTRATION COMPOSITIONS AND SUBCUTANEOUS ADMINISTRATION

TECHNICAL FIELD

Anti-ANGPTL3 antibodies and compositions comprising such compounds for use in medicine.

CROSS-REFERENCE TO RELATED APPLICATIONS

This application claims priority under 35 U.S.C. § 119 to European Patent Application 22201248.6, filed Oct. 13, 2022 and European Patent Application 22171090.8, filed May 2, 2022; the contents of which are incorporated herein by reference.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on May 2, 2023, is named "220003US01", and is 29 kilobytes in size.

BACKGROUND

Human Angiopoietin-like protein 3 (hANGPTL3) is a 460 amino acid long protein first identified by Conklin et al. (Conklin, Gilbertson et al. (1999) Genomics 62(3): 477-482). hANGPTL3 circulates in plasma as a trimer made by the two coil-coil domains present in the N-terminal part of the protein. hANGPTL3 is part of a family of Angiopoietin-like proteins influencing the lipid metabolism by inhibiting the lipoprotein lipase (LPL) and the endothelial lipase (EL).

hANGPTL3 is the most abundantly expressed member of this family and a well-described inhibitor of LPL. It mainly exerts its action in the non-fasted state. LPL is anchored in the endothelial cells and is a key enzyme responsible for hydrolysing triglycerides from triglyceride-rich lipo-particles (VLDL and chylomicrons). The more LPL activity, the more removal of triglycerides from circulation.

The inhibition of LPL by hANGPTL3 results in increased triglyceride and LDL concentration in plasma.

LPL inhibition by hANGPTL3 is believed to function through interactions with human Angiopoietin-like protein 8 (hANGPTL8) and possibly human Angiopoietin-like protein 4 (hANGPTL4). While hANGPTL8 have no in vitro inhibitory function in the absence of hANGPTL3, hANGPTL3 can inhibit LPL on its own. hANGPTL4 is also known to inhibit LPL independent of hANGPTL3 and 8. While hANGPTL3 is generally expressed by the liver, hANGPTL4 and 8 show different expression patterns in different organisms and while hANGPTL4 and 8 are mainly expressed upon external stimuli, hANGPTL3 shows high and constitutive expression from the liver.

Different cleavage forms exist in circulation (Ono, Shimizugawa et al. (2003) J Biol Chem 278(43): 41804-41809). Full-length hANGPTL3 and the cleaved forms of hANGPTL3 containing the N-terminal domain all inhibit LPL and EL resulting in increased levels of triglycerides.

Loss-of-function variants in the gene encoding hANGPTL3 are associated with hypolipidemia and protection against atherosclerotic cardiovascular disease. Evinacumab (Evkeeza®), a monoclonal antibody against hANGPTL3 (WO2012/174178), has shown benefits in patients with homozygous familial hypercholesterolemia at a dose of 15 mg per kilogram of body weight every 4 weeks (Rall et al., (2020) NEJM, 383(8), 711-720).

The high doses needed for treatment makes the currently available antibody product Evkeeza® (the recommended dose of EVKEEZA is a 15 mg/kg dose administered by i.v. infusion over 60 minutes every 4 weeks with an inline or add-on filter) unavailable for self-administration and more optimal treatment scenarios could be beneficial for the patient population.

There is a need in the art for improved anti-hANGPTL3 antibodies.

SUMMARY

The present invention relates to monovalent antibodies and antigen-binding fragments thereof that are capable of binding human ANGPTL3 (hANGPTL3) and reducing hANGPTL3-mediated inhibition of LPL and use thereof in medicine as well as in pharmaceutical compositions comprising such compounds.

In one aspect the monovalent antibodies and antigen-binding fragments thereof are capable. of binding hANGPTL3 and capable of reducing the concentration of triglycerides in human plasma.

In one aspect the monovalent antibodies and antigen-binding fragments thereof are capable of binding to hANGPTL3 and capable of reducing the concentration of hANGPTL3 in human plasma thereby reducing inhibition of LPL.

In one aspect the monovalent antibodies and antigen-binding fragments thereof are capable of binding hANGPTL3 and capable of inhibiting hANGPTL3-mediated inhibition of LPL.

In one aspect the monovalent antibodies and antigen-binding fragments thereof are capable. of binding hANGPTL3 and capable of inhibiting hANGPTL3-mediated inhibition of LPL as well as reducing the concentration of hANGPTL3 in human plasma thereby reducing hANGPTL3-mediated inhibition of LPL.

In one particular aspect the present invention relates to a monovalent antibody or antigen-binding fragment thereof capable of binding human ANGPTL3 (hANGPTL3) (SEQ ID NO:1) wherein
  a) the heavy chain of said antibody or antigen-binding fragment thereof comprises:
    a CDR1 sequence of amino acid residues SYWMT (SEQ ID NO:2) wherein none or one of these amino acid residues may be substituted by a different amino acid residue, and
    a CDR2 sequence of amino acid residues SISSHS-TYIYYADSVKG (SEQ ID NO:3), wherein none, one, two or three of these amino acid residues may be substituted by a different amino acid residue, and
    a CDR3 sequence of amino acid residues EGWYDNWFDP (SEQ ID NO:4), wherein none, one, two or three of these amino acid residues may be substituted by a different amino acid residue; or
  b) the heavy chain of said antibody or antigen-binding fragment thereof comprises:
    a CDR1 sequence of amino acid residues SYWMT (SEQ ID NO:24), wherein none or one of these amino acid residues may be substituted by a different amino acid residue, and a CDR2 sequence of amino acid residues SISSHS-TYIYYADSVKG (SEQ ID NO:25), wherein none, one, two or three of these amino acid residues may be substituted by a different amino acid residue, and a CDR3 sequence of amino acid residues EGWYDNWNDP (SEQ ID NO:26), wherein none, one, two or three of these amino acid residues may be substituted by a different amino acid residue;

and wherein the light chain of said antibody or antigen-binding fragment thereof comprises:

a CDR1 sequence of amino acid residues RASQNIR-SPYLA (SEQ ID NO:9), wherein none, one, two or three of these amino acid residues may be substituted with a different amino acid residue, and a CDR2 sequence of amino acid residues GVSSRAA (SEQ ID NO:10), wherein none, one or two of these amino acid residues may be substituted with a different amino acid residue, and a CDR3 sequence of amino acid residues QQYDDHPYT (SEQ ID NO:11), wherein none, one or two of these amino acid residues may be substituted with a different amino acid residue.

In one aspect the monovalent antibodies and antigen-binding fragments thereof may be formulated in high concentration compositions.

In one aspect the monovalent antibodies and antigen-binding fragments thereof are suitable for subcutaneous administration.

BRIEF DESCRIPTION OF FIGURES

FIG. 1A-D shows SEQ ID NOs:2-28 in tabular format.

FIGS. 4A and 4B show the effect of administration of tmAb0.1, tmAb0.2, tmAb0.3, tmAb0.4, an evinacumab sequence identical analogue (SIA) and vehicle on total ANGPTL3 concentration in mouse plasma. FIG. 4B focusses on the 100000-400000 pg/mL ANGPTL3 plasma concentration range, which is below the plasma level of ANGPTL3 in evinacumab SIA treated mice hence evinacumab SIA data are not shown in the figure.

FIG. 6A-E show SE-UPLC profiles of antibody-ANGPTL3 complexes, including evinacumab SIA (FIG. 6A), tmAb1 (FIG. 6B), tmAb2 (FIG. 6C), tmAb3 (FIG. 6D), tmAb4 (FIG. 6E) at different pH values. Dotted line represents complexes analysed at pH 6. Full line represents complexes analysed at pH 7.4.

FIG. 7 shows the self-association of tmAb1 and the bivalent form thereof designated "mAb1" at different pH values.

BRIEF DESCRIPTION OF SEQUENCES

Figure 2:
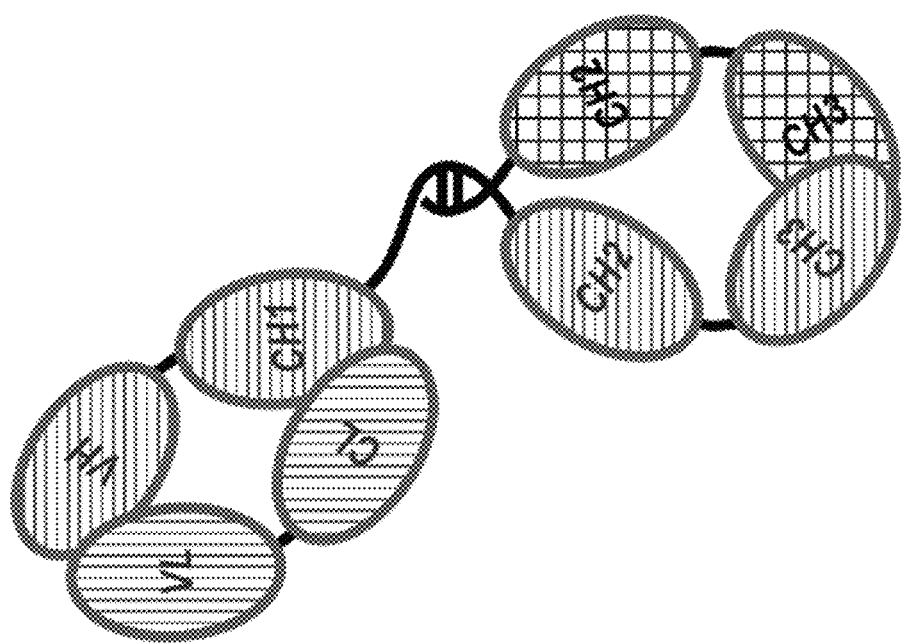
FIG. 2 shows a (non-limiting) schematic drawing of a monovalent antibody.

SEQ ID NO:1 represents the amino acid sequence of human ANGPTL3.

SEQ ID NOs:2, 3 and 4 represent the amino acid sequence of Complementarity Determining Region (CDR) 1-3, respectively, of the heavy chain of tmAb1.

SEQ ID NO:5 represents the amino acid sequence of the heavy chain variable domain (VH) of tmAb1.

SEQ ID NO:6 represents the amino acid sequence of the heavy chain of tmAb1 comprising a C-terminal Gly-Lys deletion (des-(Gly-Lys)).

SEQ ID NO:7 represents the amino acid sequence of the truncated heavy chain (tHC) of tmAb1, tmAb2, tmAb3 and tmAb4 also comprising a C-terminal Gly-Lys deletion (des-(Gly-Lys)).

SEQ ID NO:8 represents the amino acid sequence of an alternative truncated heavy chain (tHC) differing from SEQ ID NO:7 in not having a C-terminal Gly-Lys deletion.

SEQ ID NOs:9, 10 and 11 represent the amino acid sequence of Complementarity Determining Region (CDR) 1-3, respectively, of the light chain of tmAb1, tmAb2, tmAb3 and tmAb4.

SEQ ID NO:12 represents the amino acid sequence of the light chain variable domain (VL) of tmAb1, tmAb2, tmAb3 and tmAb4.

SEQ ID NO:13 represents the amino acid sequence of the light chain of tmAb1, tmAb2, tmAb3 and tmAb4.

SEQ ID NOs:14, 15 and 16 represent Complementarity Determining Region (CDR) 1-3, respectively, of the heavy chain of tmAb2.

SEQ ID NO:17 represents the amino acid sequence of the heavy chain variable domain (VH) of tmAb2.

SEQ ID NO:18 represents the amino acid sequence of the heavy chain of tmAb2.

SEQ ID NOs:19, 20 and 21 represent the amino acid sequence of Complementarity Determining Region (CDR) 1-3, respectively, of the heavy chain of tmAb3.

SEQ ID NO:22 represents the amino acid sequence of the heavy chain variable domain (VH) of tmAb3.

SEQ ID NO:23 represents the amino acid sequence of the heavy chain of tmAb3.

SEQ ID NOs:24, 25 and 26 represent the amino acid sequence of Complementarity Determining Region (CDR) 1-3, respectively, of the heavy chain of tmAb4.

SEQ ID NO:27 represents the amino acid sequence of the heavy chain variable domain (VH) of tmAb4.

SEQ ID NO:28 represents the amino acid sequence of the heavy chain of tmAb4.

DESCRIPTION

Upon intravenous (i.v.) administration of anti-ANGPTL3 antibodies such as Evkeeza® as used for inhibition of ANGPTL3 inhibition of LPL for lowering of triglycerides in human plasma, dose dependent accumulation of ANGPTL3 has been observed (Ahmad et al. (2019) Circulation August 6; 140(6): 470-486 supplemental information FIG. 2).

The phenomenon is known as antibody-mediated antigen accumulation and can cause the required antibody dosage to be hugely increased to reach therapeutic efficacy. The need for a high therapeutically effective dose can pose challenges irt. the route of administration. For example, subcutaneous (s.c.) administration of high doses of an antibody requires the antibody to have sufficiently good properties with respect to solubility, self-association and viscosity in solution.

So-called sweeping antibodies have been developed to generally increase elimination of soluble antigen bound by such antibodies (Igawa et al. (2016) Immun. Rev. 270:132-151) but oligomeric target proteins, such as ANGPTL3, pose a specific challenge for this concept when several antibodies are bound to the same target thereby exposing multiple binding opportunities for the Fc receptors. This adds avidity to the antibody-Fc receptor affinity in the antibody recycling mechanism thereby assisting uptake of the immune complexes (IC) to the endosomes. However, at the same time this challenges pH dependent antigen release and sweeping in the endosomes/lysosomes and also challenge antibody recycling by triggering clearance of the multicomponent immune complex (IC) generated when several antibodies binds to a single multimeric antigen. The presence of two or more Fab moieties on each antibody molecule exposes several binding opportunities for oligomeric targets to the same antibody potentially generating complex and heterogenous IC networks the size of which is correlated with immunologic reactions and clearance of the ICs (Opolka-Hoffmann et al. (2021) mAbs, 13:1, 1995929; St. Clair et al. (2017) PLOS one, 12(1):e0170556).

The present inventors have found that an improved viscosity profile of antibodies could be achieved by utilizing a monovalent antibody format further having pH-dependent binding properties, thereby giving the antibody a potential for being administered by s.c. administration. Surprisingly, the switching to a monovalent format with only one ANGPTL3 binding site per molecule resulted in triglyceride-lowering potency on par with Evkeeza® having two ANGPTL3 binding sites per molecule. The smaller size of the antibodies disclosed herein further strengthens the potential for s.c. administration. The antibodies disclosed herein have biophysical properties allowing for a concentration in solution of at least 70 mg/ml, in contrast to Evkeeza®, which is to be prepared in an i.v. infusion bag at a concentration of 20 mg/ml at the most.

The present invention thus relates to monovalent antibodies and antigen-binding fragments thereof that are capable of binding hANGPTL3 and reducing hANGPTL3-mediated inhibition of LPL and use thereof in medicine as well as in pharmaceutical compositions comprising such compounds, including pharmaceutical compositions suitable for s.c. administration.

In one aspect the monovalent antibodies or antigen-binding fragments thereof are capable of binding hANGPTL3 and reducing the concentration of triglycerides in human plasma.

In one such aspect the monovalent antibodies and antigen-binding fragments thereof are capable of binding to hANGPTL3 and reducing the concentration of hANGPTL3 in human plasma thereby reducing inhibition of LPL.

In another such aspect the monovalent antibodies and antigen-binding fragment thereof are antagonists capable of binding hANGPTL3 and inhibiting hANGPTL3-mediated inhibition of LPL.

In one aspect the monovalent antibodies and antigen-binding fragment thereof are capable of binding hANGPTL3 and inhibiting hANGPTL3-mediated inhibition of LPL as well as reducing the concentration of hANGPTL3 in human plasma thereby reducing hANGPTL3-mediated inhibition of LPL.

In one aspect the monovalent antibodies or antigen-binding fragment thereof do not increase the concentration of hANGPTL3 in human plasma after administration.

In one aspect the monovalent antibodies or antigen-binding fragments thereof lower the concentration of hANGPTL3 in human plasma after administration.

In one aspect the monovalent antibodies or antigen-binding fragment thereof provide reduced viscosity, reduced gel formation and a low self-association tendency across a broad pH interval in solution as compared to corresponding bivalent antibodies.

In one particular aspect the present invention relates to a monovalent antibody or antigen-binding fragment thereof capable of binding human ANGPTL3 (hANGPTL3) (SEQ ID NO:1) wherein
  a) the heavy chain of said antibody or antigen-binding fragment thereof comprises:
    a CDR1 sequence of amino acid residues SYWMT (SEQ ID NO:2) wherein none or one of these amino acid residues may be substituted by a different amino acid residue, and
    a CDR2 sequence of amino acid residues SISSHSTYIYYADSVKG (SEQ ID NO:3), wherein none, one, two or three of these amino acid residues may be substituted by a different amino acid residue, and
    a CDR3 sequence of amino acid residues EGWYDNWFDP (SEQ ID NO:4), wherein none, one, two or three of these amino acid residues may be substituted by a different amino acid residue; or
  b) the heavy chain of said antibody or antigen-binding fragment thereof comprises:
    a CDR1 sequence of amino acid residues SYWMT (SEQ ID NO:24), wherein none or one of these amino acid residues may be substituted by a different amino acid residue, and
    a CDR2 sequence of amino acid residues SISSHSTYIYYADSVKG (SEQ ID NO:25), wherein none, one, two or three of these amino acid residues may be substituted by a different amino acid residue, and
    a CDR3 sequence of amino acid residues EGWYDNWNDP (SEQ ID NO:26), wherein none, one, two or three of these amino acid residues may be substituted by a different amino acid residue;
and
wherein the light chain of said antibody or antigen-binding fragment thereof comprises:
  a CDR1 sequence of amino acid residues RASQNIRSPYLA (SEQ ID NO:9), wherein none, one, two or three of these amino acid residues may be substituted with a different amino acid residue, and
  a CDR2 sequence of amino acid residues GVSSRAA (SEQ ID NO:10), wherein none, one or two of these amino acid residues may be substituted with a different amino acid residue, and
a CDR3 sequence of amino acid residues QQYDDHPYT (SEQ ID NO:11), wherein none, one or two of these amino acid residues may be substituted with a different amino acid residue.

In one aspect the monovalent antibodies and antigen-binding fragments thereof are suitable for subcutaneous administration.

In one aspect the monovalent antibodies and antigen-binding fragments thereof may be formulated in high concentration compositions.

In one aspect the monovalent antibodies or antigen-binding fragment thereof may be prepared in compositions; wherein the concentration of the antibody or antigen-binding fragment thereof is 25 mg/ml or more, preferably 50 mg/ml or more, such as 70 mg/ml or more.

In order that the present invention may be more readily understood, certain terms are first defined.

The term "a" or "an" is intended to mean "one or more." The term "comprise" and variations thereof such as "comprises" and "comprising," when preceding the recitation of a step or an element, are intended to mean that the addition of further steps or elements is optional and not excluded.

The term "about" is used herein to mean approximately, roughly, or around. When the term "about" is used in conjunction with a numerical range, it modifies that range by extending the boundaries above and below the numerical values set forth. In general, the term "about" can modify a numerical value above and below the stated value by 10 percent, up or down (higher or lower).

The term "antagonistic antibody" as used herein refers to an antibody that inhibits or decreases the biological activity of an antigen that the antibody binds, such as hANGPTL3. In some embodiments, the antibody or the antigen-binding fragment thereof specifically binds to hANGPTL3 such to partly or completely block its inhibitory effect on LPL, thereby, for example, reducing triglyceride levels in the plasma of a human patient.

The term "antibody" includes—but is not limited to— full-length antibodies comprising at least four polypeptide chains: two heavy chains (HC) and two light chains (LC) that are connected by disulphide bonds as well as antibodies comprising at least three polypeptide chains: two heavy chains (HC) and one light chain (LC) that are connected by disulphide bonds. One of the heavy chains can be a truncated heavy chain.

One class of immunoglobulins of particular pharmaceutical interest is the IgGs. In humans, the IgG class may be divided into four sub-classes IgG1, IgG2, IgG3 and IgG4, based on the sequence of their heavy chain constant regions. The light chains can be divided into two types, kappa and lambda chains, based on differences in their sequence composition. IgG molecules are composed of two heavy chains, interlinked by two or more disulphide bonds, and two light chains, each attached to a heavy chain by a disulphide bond.

An IgG heavy chain may comprise a heavy chain variable domain ($V_H$) and up to three heavy chain constant ($C_H$) domains: $C_H1$, $C_H2$ and $C_H3$. A light chain may comprise a light chain variable domain ($V_L$) and a light chain constant domain ($C_L$). $V_H$ and $V_L$ regions can be further subdivided into regions of hypervariability, termed complementarity determining regions (CDRs) or hypervariable regions (HvRs), interspersed with regions that are more conserved, termed framework regions (FR). $V_H$ and $V_L$ domains are typically composed of three CDRs and four FRs, arranged from amino-terminus to carboxy-terminus in the following order: FR1, CDR1, FR2, CDR2, FR3, CDR3, FR4. The heavy and light chain variable domains containing the hypervariable regions (CDRs) form a structure that is capable of interacting with an antigen, whilst the constant region of an antibody may mediate binding of the immunoglobulin to host tissues or factors, including, but not limited to various cells of the immune system (effector cells), Fc receptors and the first component, C1q, of the C1 complex of the classical complement system.

Antibodies of the invention may be monoclonal antibodies (mAbs), such as monovalent monoclonal antibodies. Antibodies of the invention may be produced and purified using various methods that are known to a person skilled in the art. For example, antibodies may be produced from hybridoma cells. Antibodies may be produced by B-cell expansion. Antibodies or antigen-binding fragments thereof may be recombinantly expressed in mammalian or microbial expression systems, or by in vitro translation. Antibodies or antigen-binding fragments thereof may also be recombinantly expressed as cell surface bound molecules, by means of e.g. phage display, bacterial display, yeast display, mammalian cell display or ribosome or mRNA display.

Antibodies or antigen-binding fragments thereof may be defined in terms of their complementarity-determining regions (CDRs). The term "Complementarity Determining Region" or "CDR", when used herein, refers to the regions of an antibody in which amino acid residues involved in antigen-binding are situated. The CDRs can be identified as the regions with the highest variability in amino acid alignments of antibody variable domains. Databases can be used for CDR identification such as the Kabat database, with the CDRs e.g. being defined as comprising amino acid residues 24-34 (L1), 50-56 (L2) and 89-97 (L3) of the light chain variable domain and 31-35 (H1), 50-65 (H2) and 95-102 (H3) in the heavy chain variable domain; (Kabat et al. 1991; Sequences of Proteins of Immunological Interest, Fifth Edition, U.S. Department of Health and Human Services, NIH Publication No. 91-3242). Typically, the numbering of amino acid residues in this region is performed by the method described in Kabat et al. supra. Phrases such as "Kabat position", "Kabat residue", and "according to Kabat" herein refer to this numbering system for heavy chain variable domains or light chain variable domains, and unless contradicted by the context numbering according to Kabat is used herein.

Numbering of amino acid residues in the constant region of antibodies is performed by reference to the numbering used for the crystal structure of human IgG1 (Edelman et al. (1969) Proc. Natl. Acad. Sci. USA 63: 78-85) and phrases such as "EU position", "EU residue" and "according to EU index" herein refer to numbering of heavy and light chain constant domains according to Edelman et al. (1969) Proc. Natl. Acad. Sci. USA 63: 78-85.

Reference to a position in a heavy (or light) chain such as "valine (V) in position 250" means that valine is found in position 250 in both heavy chains (to the extent that the given residue position exists in both heavy chains) unless otherwise stated or contradicted by the context.

The term "antigen-binding fragment" of an antibody refers to one or more fragment(s) of an antibody that retain(s) the ability to specifically bind to or recognise an antigen, such as ANGPTL3 and in particular hANGPTL3, as described herein. Examples of antigen-binding fragments include (but is not limited to) monovalent molecules comprising both a single $V_H$, a single $V_L$ domain, and a Fc-receptor interacting region.

Antibody fragments of the invention may be made e.g. by deletion of one or more amino acids from the N- and/or C-terminal ends of the heavy and/or light chain(s). Fragments may also be generated by one or more internal deletions.

The present invention encompasses variants of the antibodies, or antigen-binding fragments thereof as disclosed herein, which may comprise one or more amino acid substitutions and/or deletions and/or insertions in the individual sequences disclosed herein.

"Substitution" variants preferably involve the replacement of one or more amino acid(s) with the same number of amino acid(s). Substitutions may be, but are not limited to, conservative substitutions. For example, for conservative substitutions, an amino acid may be substituted to an amino acid with similar biochemical properties, for example, a basic amino acid may be substituted to another basic amino acid (e.g. lysine to arginine), an acidic amino acid may be substituted to another acidic amino acid (e.g. glutamate to aspartate), a neutral amino acid may be substituted to another neutral amino acid (e.g. threonine to serine), a charged amino acid may be substituted to another charged amino acid (e.g. glutamate to lysine), a hydrophilic amino acid may be substituted to another hydrophilic amino acid (e.g. asparagine to glutamine), a hydrophobic amino acid may be substituted to another hydrophobic amino acid (e.g. alanine to valine), a polar amino acid may be substituted to another polar amino acid (e.g. serine to threonine), an aromatic amino acid may be substituted to another aromatic amino acid (e.g. phenylalanine to tryptophan) and an aliphatic amino acid may be substituted to another aliphatic amino acid (e.g. leucine to isoleucine).

Preferred variants include those which, instead of the amino acid residue, which appears in the sequence, comprises a structural analogue of the amino acid residue.

Antibodies and antigen-binding fragments thereof as disclosed herein comprise a region that can interact with cell surface receptors called Fc receptors, such as, but not limited to, the crystallisable region ("Fc region", also known as a "Fc domain"). The Fc region is the C-terminal region of an antibody, which comprises the hinge and the constant $C_H2$ and $C_H3$ domains. The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as plasma half-life, complement fixation, Fc-receptor binding, protein stability and/or antigen-dependent cellular cytotoxicity, or lack thereof, among others (e.g., T252L/T254S/T256F Ghetie et al., (1997) Nature Biotechnol. 15:637-640; M428L/N434S, Zalevsky et al., (2010) Nat. Biotechnol. 28:157-159; H433K/N434F, Ober (2014) (U.S. Pat. No. 8,834,871); T307A/E380A/N434A, Petkova et al. (2006) Int. Immunol 18:1759-1769; T250A/M428L, Hinton et al. (2006) J. Immunol. 176:346-356; M252Y/S254T/T256E, US2003/0190311, Dall'Acqua et al. (2006) J. Biol. Chem. 281: 23514-23524; N434H, Zheng et al., (2011) Clin. Pharm.&Ther. 89:283-290; M252Y/T256D, T256D/T307Q, T256D/T307W, Mackness et al. (2019) mAbs 11:1276-1288, residue numbering according to the EU index). Furthermore, the antibodies and antigen-binding fragments thereof may be chemically modified (e.g., one or more chemical moieties can be attached to the antibody) or be modified to alter its glycosylation, again to alter one or more functional properties of the antibody.

An antibody, such as an IgG1 antibody, may carry a modified Fc domain comprising one or more, and preferably all of the following substitutions, that will result in increased binding to certain Fc-gamma receptors, such as Q311R and P343R in combination with L234Y, P238D, T250V, V264I, T307P and A330K (residue numbering according to the EU index). Alternatively, other amino acid substitutions, known in the art to lead to increased FcRn and/or Fc-gamma receptor binding, optionally in combination with the substitutions mentioned above, may be used. See for example WO2016/125495 as well as, WO2013/002362, WO2014/104165, WO2012/115241, WO2014/030728, WO2014/163101 and WO2017/104783, all of which are incorporated herein by reference.

An IgG1 antibody may carry a modified Fc domain comprising substitutions that will result in increased plasma half-life. In one embodiment such substitutions include M252Y, S254T and T256E in combination (residue numbering according to the EU index). See also US2003/0190311 incorporated herein by reference.

The term "binding affinity" is a measure of the strength of a non-covalent interaction between two molecules, e.g. an antibody, or fragment thereof, and an antigen. The term is used to describe monovalent interactions. Binding affinity between two molecules, e.g. an antibody, or fragment thereof, and an antigen, through a monovalent interaction may be quantified by determining the equilibrium dissociation constant ($K_D$). $K_D$ can be determined by measurement of the kinetics of complex formation and dissociation, e.g. by the Surface Plasmon Resonance (SPR) method or the Isothermal Titration calorimetry (ITC) method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D = k_d/k_a$.

Following the above definition, binding affinities associated with different molecular interactions, such as the binding affinity of different antibodies for a given antigen, may be compared by comparison of the $K_D$ values for the individual antibody/antigen complexes.

The value of the dissociation constant can be determined directly by well-known methods. Standard assays to evaluate the binding ability of ligands such as antibodies towards targets are known in the art and include, for example, ELISAs, Western blots, RIAs, and flow cytometry analysis. The binding kinetics and binding affinity of the antibody also can be assessed by standard assays known in the art, such as SPR.

A competitive binding assay can be conducted in which the binding of the antibody to the target is compared to the binding of the target in the presence of another ligand of that target, such as another antibody.

Unless contradicted by context, the $K_D$ is preferably determined by Surface Plasmon Resonance as described herein (see example 7).

A "cross-species reactive" antibody binds to ANGPTL3 from all indicated species (e.g. human, mouse and cynomolgus monkey) with comparable affinity, in particular with a $K_D$ in the range of a factor of 100, such as within a range of a factor of 50, within a range of a factor of 20, or within a range of a factor of 10. Within a $K_D$ range of a defined factor X means that the highest affinity for a particular listed species is not more than X-times higher than the lowest affinity measured for binding to a different listed species. A person skilled in the art will understand that any method for measuring affinity can be used to verify that a cross-species reactive antibody binds to the target antigen from all listed species within a given $K_D$ factor range as described herein as long as the same conditions are applied to the $K_D$ measurement for all listed species. Preferably, the $K_D$ values are measured using SPR, in particular at 25° C. Preferably, the affinities are measured using the cross-species reactive antibody as Fab fragment.

The term "elevated triglyceride concentration in plasma" as used herein refers to plasma levels of 150-500 mg/dL.

The term "highly elevated triglyceride concentration in plasma" as used herein refers to plasma levels above 500 mg/dL.

The term "normal triglyceride concentration in plasma" as used herein refers to plasma levels below 150 mg/dL.

The term "identity" as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues.

"Identity" measures the percent of identical matches between the smaller of two or more sequences with gap alignments (if any) addressed by a particular mathematical model or computer program (i.e., "algorithms"). Identity of related polypeptides can be readily calculated by known methods. In the present invention similarity and identity were determined using Needleman (Needleman et al. J. Mol. Biol. 1970; 48:443-453) from EMBOSS-6.6.0 using the parameters 10 and 0.5 for gaps opening and extensions, respectively (gapopen=10, gapextend=0.5).

The term "monovalent antibody" as used herein, refers to an antibody which is capable of binding one antigen molecule and not capable of antigen crosslinking.

The term "one-armed" as used herein, refers to a particular type of monovalent antibody constituted by an antibody single light chain, a heavy chain and a truncated heavy chain lacking at least the heavy chain Fv region.

The term "monospecific" antibody as used herein, refers to an antibody which is capable of binding to a single epitope.

The term "human antibody", as used herein, is intended to include antibodies having variable domains in which at least a portion of a framework region and/or at least a portion of a CDR region is/are derived from human germline immunoglobulin sequences. For example, a human antibody may have variable domains in which both the framework and CDR regions are derived from human germline immunoglobulin sequences. Furthermore, if the antibody contains a constant region, the constant region or a portion thereof is also derived from human germline immunoglobulin sequences. Preferably, a human antibody is a monoclonal antibody.

The term "heavy chain" includes a full-length heavy chain. A full-length heavy chain includes a variable domain, $V_H$, and three constant domains, $C_H1$, $C_H2$, and $C_H3$. The $V_H$ domain is at the amino-terminus of the polypeptide, and the CH domains are at the carboxyl-terminus, with the $C_H3$ being closest to the —COOH end. The C-terminal end of the heavy chain may comprise a C-terminal Gly-Lys deletion (des-(Gly-Lys)).

The term "light chain" as used herein includes a full-length light chain. A full-length light chain includes a variable domain, $V_L$, and a constant domain, $C_L$. The variable domain of the light chain is at the amino-terminus of the polypeptide. Light chains as described herein include kappa chains and lambda chains.

The term "immune complex" as used herein refers to the complex formed by one or more antibody(ies) when bound to one or more target antigen(s). An example hereof is one or more anti-ANGPTL3 antibody(ies) bound to two or more ANGPTL3 molecules. The term is used interchangeably with "immunocomplex".

The term "isoelectric point" or "pI" as used herein refers to the pH value where the overall net charge of a protein—such as an antibody—is zero. In proteins there may be many charged groups, and at the pI the sum of all these charges is zero. At a pH above the pI the overall net charge of the protein will be negative, whereas at pH values below the pI the overall net charge of the protein will be positive.

The pI may be either a theoretical or an experimentally determined pI.

The skilled person is aware of methods to determine the pI of a protein. Most commonly, the pI of a protein is computed based on the amino acid sequence of the protein. Numerous (online) tools allowing the determination of the isoelectric point of a protein are available, such as "ExPASy Compute pI/Mw"; see Protein Identification and Analysis Tools on the ExPASy Server; Gasteiger E., Hoogland C., Gattiker A., Duvaud S., Wilkins M. R., Appel R. D., Bairoch A.; (In) John M. Walker (ed): The Proteomics Protocols Handbook, Humana Press (2005), pp. 571-607.

The pI can also be determined experimentally and charge variants can, for example, be separated using charged based-separation techniques such as isoelectric focusing (IEF) gel electrophoresis or capillary isoelectric focusing (cIEF) gel electrophoresis.

The term "multimerization domain" as used herein refers to a region of each of the heavy chains of e.g. a monovalent antibody. The "multimerization domain" promotes stable interaction between the entities of chimeric monovalent antibody or antigen-binding fragments thereof. Preferably, the multimerization domain promotes interaction between a first heavy chain and a second heavy chain, thereby enhancing the formation of the desired heteromultimeric monovalent antibody and substantially reducing the probability of the formation of undesired homomultimeric antibodies. The multimerization domains may interact via an immunoglobulin sequence, leucine zipper, a hydrophobic region, a hydrophilic region, or a free thiol, which forms an intermolecular disulphide bond between the chimeric molecules of the chimeric heteromultimer. The free thiol may be introduced into the interface of one or more interacting polypeptides by substituting a naturally occurring residue of the polypeptide with, for example, a cysteine at a position allowing for the formation of a disulphide bond between the first and second heavy chains. The multimerization domain may comprise an immunoglobulin constant region. A possible multimerization domain is disclosed in PCT/US90/06849 in which hybrid immunoglobulins are described. In addition, a multimerization region may be engineered such that steric interactions not only promote stable interaction, but further promote the formation of heterodimers over homodimers from a mixture of monomers. See, for example, PCT/US96/01598 in which a "protuberance-into-cavity" strategy is disclosed for an interface between a first and a second polypeptide for hetero-oligomerization and in particular WO98/50431. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). The immunoglobulin sequence is an immunoglobulin constant domain. The immunoglobulin moiety in the antibodies as disclosed herein may be obtained from IgG1, IgG2, IgG3 or IgG4 subtypes.

Numerous technologies exist for generation of chimeric, hybrid or asymmetric immunoglobulins and the truncation technology used in the current application (Merchant et al., (2013) PNAS USA 110:E2987-2996) can potentially be used in combination with any of the chimeric formats (e.g. DEEK (De Nardis et al., (2017) J. Biol. Chem. 292:14706-14717), ART-Ig and FAST-Ig (Shiraiwa et al., (2019) Methods 154:10-20; Yamaguchi et al., (2020) Blood 136:19) or DuoBody (Labrijn et al., (2013) PNAS USA 110: 5145-5150).

The term "plasma half-life" as used herein refers to the time required for half the quantity of a substance administered to a patient to be metabolized or eliminated from the serum or plasma of the patient by normal biological processes.

The term "surface exposed amino acid residue" as used herein refers to amino acid residues whose side chain can be in contact with solvent molecules (which in general may be mostly water molecules). However, the side chain does not necessarily have to be wholly in contact with solvent molecules, and when even a portion of the side chain is in contact with the solvent molecules, the amino acid residue is defined as an "amino acid located on the surface". The amino acid residues located on the surface of a polypeptide can also include amino acid residues located close to the antibody surface and thereby can have a mutual electric charge influence from other amino acid residue(s) whose side chain, even partly, is in contact with the solvent molecules. Those of ordinary skill in the art can prepare a homology model or a machine learning based three-dimensional molecular model of a polypeptide or antibody by for example homology modelling or machine learning using commercially or publicly available softwares. Alternatively, it is possible to use methods such as X-ray crystallography for three-dimensional molecular model generation. The amino acid residues that may be exposed on the surface can be determined, for example, using coordinates from a three-dimensional molecular model of an antibody using a computer program such as MOE (Chemical Computing Group) or Bioluminate (Schrödinger). Surface exposed sites may be determined using algorithms known in the technical field (for example, Lee and Richards (1971) J. Mol. Biol. 55:379-400; Connolly, J. Appl. Cryst. (1983) 16:548-558). Surface exposable sites can be determined using software suitable for protein modelling and analysis of three-dimensional structure information obtained from the antibody. Software available for such purposes includes, for example, the MOE (Chemical Computing Group) or Bioluminate (Schrödinger). The solvent accessible surface (in A2) area are calculated using a water probe with a probe radius of 1.4 Å. Furthermore, methods for determining surface exposed regions and areas using software for personal computers have been described by Pacios (Pacios, Comput. Chem. 18(4):377-386 (1994); J. Mol. Model. 1:46-53 (1995)). Based on such information as described above, appropriate amino acid residues located on the surface of an antibody in contact with solvent can be selected.

The term "treatment", as used herein, refers to the medical therapy of any human subject in need thereof. Said subject is expected to have undergone physical examination by a medical practitioner, who has given a tentative or definitive diagnosis, which would indicate that the use of said specific treatment is beneficial to the health of said human subject. The timing and purpose of said treatment may vary from one individual to another, according to the status quo of the subject's health. Thus, said treatment may be prophylactic, palliative, symptomatic and/or curative. In terms of the present invention, prophylactic, palliative, symptomatic and/or curative treatments may represent separate aspects of the invention.

As used herein the terms "treating", "treat" or "treatment" and variations thereof include administering a therapeutically effective amount of an antibody as disclosed herein sufficient to reduce or eliminate at least one symptom of the disorder. "Treatment", however, need not be a cure.

As used herein the terms "preventing", "prevent" or "prevention" or variations thereof refers to protecting a subject from developing at least one symptom of a disease or reducing the severity of a symptom of a disorder.

The term "truncated heavy chain" as used herein refers to a heavy chain lacking at least part of the variable domain such to no longer being able to bind hANGPTL3 and optionally lacking the first constant IgG domain (CH1) or part thereof such to not comprise a cysteine residue suitable for heavy/light chain pairing (such as IgG1 Cys220 EU residue). In one embodiment "truncated heavy chain" refers to a heavy chain lacking the entire variable domain, $C_H1$ and part of the hinge region such that IgG1 Asp221 (EU residue) is the N-terminal amino acid residue. For clarity, a heavy chain wherein only the C-terminal glycine-lysine residues in positions 446 and 447 are removed is thus not considered a "truncated heavy chain".

In another embodiment the truncated heavy chain differs from a full-length heavy chain in that the Fab region is not present and that the C-terminal glycine-lysine residues in positions 446 and 447 in SEQ ID NO:8 (EU residues), respectively, are present (SEQ ID NO:8) or not present (SEQ ID NO:7).

In one such embodiment the monovalent antibodies as disclosed herein comprise a heavy chain and a truncated heavy chain wherein both said chains are of the IgG1 isotype or based on the IgG1 isotype and wherein the Fab region and Gly-Lys C-terminal residues in positions 446 and 447 (EU residues), respectively, are not present in the truncated heavy chain, and wherein the Gly-Lys C-terminal residues in positions 446 and 447 (EU residues) of the heavy chain are not present.

In a preferred embodiment the truncated heavy chain comprises SEQ ID NO:7.

The term "high concentration" as used herein in relation to pharmaceutical compositions means a concentration of 50 mg/ml or above.

Production of Monovalent Antibodies

The monovalent antibodies or antigen-binding fragments thereof as disclosed herein can be produced in one host cell line expressing three different polypeptide chains, in particular a heavy chain, a truncated heavy chain, and a light chain, see for example FIG. 2 for a non-limiting illustration of such antibody. No further arm-exchange or in vitro refolding of the antibody is needed to obtain the fully functional molecule.

In one embodiment, the monovalent antibodies or antigen-binding fragments thereof comprise the so-called knob-in-hole substitutions facilitating heterodimerization of two different heavy chains, such as a full-length heavy chain and a truncated heavy chain. Various sets of knob-in-hole substitutions exist and in a preferred embodiment the heavy chain comprises T366W (EU residue) and the truncated heavy chain comprises the T366S, L368A and Y407V (EU residue). See also WO98/50431, which is incorporated herein by reference.

In a preferred embodiment the monovalent antibodies contain a light chain, a full-length heavy chain, and a truncated heavy chain (221-445, EU residues) all being co-expressed and assembled in a host cell suitable for production of antibodies.

In another preferred embodiment the monovalent antibodies contain a light chain, a C-terminal des-Gly-Lys heavy chain (1-445, EU residues), and a C-terminal des-Gly-Lys truncated heavy chain (221-445, EU residues) all being co-expressed and assembled in a host cell suitable for production of antibodies.

Complexes comprising hANGPTL3 and antibodies as disclosed herein are observed at neutral pH (pH 7.4), thus the affinity of the monovalent antibodies is sufficient for efficient binding to hANGPTL3. Binding of 2-3 monovalent antibodies to the trimeric hANGPTL3 antigen has been demonstrated, resulting in more uniform and less heterogenous hANGPTL3/antibody immune complexes as compared to evinacumab SIA antibody/hANGPTL3 immune complexes (see example 6).

In one embodiment the antibodies or antigen-binding fragments thereof as disclosed herein provide smaller and less heterogenous antibody/hANGPTL3 immune complexes as compared to evinacumab SIA antibody/hANGPTL3 immune complexes. Smaller and/or less heterogeneous immune complexes are expected to lead to reduced immunogenicity as compared to the case where antibody/hANGPTL3 complexes are larger and/or more heterogeneous.

Increasing Cellular Uptake of Antibody-Antigen Complexes

The monovalent antibodies as disclosed herein are capable of pH-dependent binding of hANGPTL3 and comprise substitutions such to increase cellular uptake of antibody-antigen complexes.

pH-Dependent Antibodies

The monovalent antibodies or antigen-binding fragments thereof as disclosed herein have a lower antigen-binding activity in the acidic pH range than in the neutral pH range. Consequently, the decreased affinity towards hANGPTL3 at lower pH (see Example 7) result in full or almost full dissociation of hANGPTL3/antibody complexes at low pH (pH 6.0).

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 20 or higher.

In one embodiment the antibody or antigen-binding fragment thereof has a $K_D$(pH6)/15 $K_D$(pH7.4) value, defined as the ratio of $K_D$ for the antigen at pH6 and $K_D$ for the antigen at pH7.4, of 30 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 40 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 50 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 60 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 70 or higher.

In one embodiment the antibody or antigen-binding fragment thereof has a $K_D$(pH6)/30 $K_D$(pH7.4) value, defined as the ratio of $K_D$ for the antigen at pH6 and $K_D$ for the antigen at pH7.4, of 80 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 90 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 95 or higher.

In one embodiment the antibody or antigen-binding fragment thereof has a $K_D$(pH6)/5 $K_D$(pH7.4) value, defined as the ratio of $K_D$ for the antigen at pH6 and $K_D$ for the antigen at pH7.4, of 100 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 110 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 120 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 130 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 140 or higher.

In one embodiment the antibody or antigen-binding fragment thereof has a $K_D$(pH6)/20 $K_D$(pH7.4) value, defined as the ratio of $K_D$ for the antigen at pH6 and $K_D$ for the antigen at pH7.4, of 150 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 160 or higher, such as 166 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 170 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 180 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 190 or higher.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, of 200 or higher.

In one embodiment the antibody or antigen-binding fragment thereof has a $K_D$(pH6)/5 $K_D$(pH7.4) value, defined as the ratio of $K_D$ for the antigen at pH6 and $K_D$ for the antigen at pH7.4, in the range 40 to 500.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, in the range 40 to 400.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, in the range 40 to 300.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, in the range 40 to 200.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, in the range 90 to 500.

In one embodiment the antibody or antigen-binding fragment thereof has a $K_D$(pH6)/20 $K_D$(pH7.4) value, defined as the ratio of $K_D$ for the antigen at pH6 and $K_D$ for the antigen at pH7.4, in the range 90 to 400.

In one embodiment the antibody or antigen-binding fragment thereof has a $K_D$(pH6)/$K_D$(pH7.4) value, defined as the ratio of $K_D$ for the antigen at pH6 and $K_D$ for the antigen at pH7.4, in the range 90 to 300.

In one embodiment the antibody or antigen-binding fragment thereof has a $K_D(pH6)/K_D(pH7.4)$ value, defined as the ratio of $K_D$ for the antigen at pH6 and $K_D$ for the antigen at pH7.4, in the range 90 to 200.

In one embodiment the antibody or antigen-binding fragment thereof has a $K_D(pH6)/K_D(pH7.4)$ value, defined as the ratio of $K_D$ for the antigen at pH6 and $K_D$ for the antigen at pH7.4, in the range 80 to 250.

In one embodiment the antibody or antigen-binding fragment thereof has a $K_D(pH6)/K_D(pH7.4)$ value, defined as the ratio of $K_D$ for the antigen at pH6 and $K_D$ for the antigen at pH7.4, in the range 80 to 200.

In one embodiment the antibody or antigen-binding fragment thereof has a $K_D(pH6)/K_D(pH7.4)$ value, defined as the ratio of $K_D$ for the antigen at pH6 and $K_D$ for the antigen at pH7.4, in the range 80 to 170.

In one embodiment the antibody or antigen-binding fragment thereof has a $K_D(pH6)/5\ K_D(pH7.4)$ value, defined as the ratio of $K_D$ for the antigen at pH6 and $K_D$ for the antigen at pH7.4, in the range 90 to 250.

In one embodiment the antibody or antigen-binding fragment thereof has a $K_D(pH6)/K_D(pH7.4)$ value, defined as the ratio of $K_D$ for the antigen at pH6 and $K_D$ for the antigen at pH7.4, in the range 90 to 200.

In one embodiment the antibody or antigen-binding fragment thereof has a $K_D(pH6)/K_D(pH7.4)$ value, defined as the ratio of $K_D$ for the antigen at pH6 and $K_D$ for the antigen at pH7.4, in the range 90 to 170.

In one embodiment the antibody or antigen-binding fragment thereof has a $K_D(pH6)/K_D(pH7.4)$ value, defined as the ratio of $K_D$ for the antigen at pH6 and $K_D$ for the antigen at pH7.4, in the range 90 to 166.

In one embodiment the antibody or antigen-binding fragment thereof has a $K_D(pH6)/K_D(pH7.4)$ value, defined as the ratio of $K_D$ for the antigen at pH6 and $K_D$ for the antigen at pH7.4, in the range 95 to 250.

In one embodiment the antibody or antigen-binding fragment thereof has a $K_D(pH6)/20\ K_D(pH7.4)$ value, defined as the ratio of $K_D$ for the antigen at pH6 and $K_D$ for the antigen at pH7.4, in the range 95 to 200.

In one embodiment the antibody or antigen-binding fragment thereof has a $K_D(pH6)/K_D(pH7.4)$ value, defined as the ratio of $K_D$ for the antigen at pH6 and $K_D$ for the antigen at pH7.4, in the range 95 to 170.

In one embodiment the antibody or antigen-binding fragment thereof has a $K_D(pH6)/K_D(pH7.4)$ value, defined as the ratio of $K_D$ for the antigen at pH6 and $K_D$ for the antigen at pH7.4, in the range 95 to 166.

Improved Fc Receptor Binding

In the context of the present invention, increased cellular uptake of antibody-antigen complexes is desirable in order to lower the levels of circulating hANGPTL3.

In some embodiments the increased cellular uptake of antibody-antigen complexes is promoted by increasing affinity of the monovalent antibodies towards the cell surface. Introduction of additional positive charges in the Fc part of antibodies results in increased uptake due to increased interaction with the negatively charged surface of the cell, thus overall increasing the cellular uptake of antibody and antibody-antigen complexes.

In some embodiments the increased cellular uptake of antibody-antigen complexes is promoted by increased affinity of the monovalent antibodies towards human FcγRIIb (CD32). By amino acid substitutions in the Fc part of antibodies the affinity towards human FcγRIIb (CD32) is increased at pH 7.4, while the substitutions do not affect the affinity of the antibodies towards other Fc receptors on the cell surface.

In some embodiments the increased cellular uptake of antibody-antigen complexes is promoted by increased avidity of the antibody-antigen immunocomplex towards human FcγRIIb (CD32). By amino acid substitutions in the Fc part of antibodies the avidity of the antibody-antigen immunocomplex towards human FcγRIIb (CD32) is increased at pH 7.4, while the substitutions do not affect avidity towards other Fc receptors on the cell surface.

In one embodiment, monovalent antibodies or antigen-binding fragments thereof enhances the clearance of hANGPTL3 from the circulation by at least about 20%, about 30%, about 40%, about 50%, about 60%, about 70%, or about 80%, relative to not administering the monovalent antibodies or antigen-binding fragments thereof. Circulating levels of hANGPTL3 can be measured by in vitro assays well known in the art and that described herein (see example 5).

Inhibitory Effect of Monovalent Antibodies

The inhibitory activity of monovalent antibodies or antigen-binding fragments thereof as described herein on hANGPTL3-mediated LPL inhibition may be determined by methods such as those described in Example 4 herein.

In one embodiment, monovalent antibodies or antigen-binding fragments thereof as described herein are capable of reducing the triglyceride concentration in human plasma.

In one embodiment, the monovalent antibodies or antigen-binding fragments thereof as described herein are capable of suppressing elevation of the triglyceride concentration in human plasma.

Indications

The disease or disorder treatable by administering the monovalent antibodies or antigen-binding fragment thereof as disclosed herein is any disease or condition which is improved, ameliorated, inhibited or prevented, or its occurrence rate reduced, compared to that without anti-hANGPTL3 antibody treatment (e.g., hANGPTL3-mediated diseases or disorders), by removing, inhibiting, reducing, or otherwise interfering with, hANGPTL3 activity.

Examples of diseases or disorders treatable include, but are not limited to, those involving lipid metabolism, such as hyperlipidemia, hyperlipoproteinemia and dyslipidemia, including atherogenic dyslipidemia, diabetic dyslipidemia, hypertriglyceridemia, hypercholesterolemia, chylomicronemia, mixed dyslipidemia (obesity, metabolic syndrome, diabetes, etc.), and the like, which are caused by, for example, decreased LDL receptor (LDLR) activity and/or LDL receptor deficiency (e.g., homozygous familial hypercholesterolemia with LDLR−/−), altered ApoC2, ApoE deficiency, increased ApoB, increased production and/or decreased elimination of very low-density lipoprotein (VLDL) and the like.

The monovalent antibodies or antigen-binding fragment thereof as disclosed herein are also useful in the prevention or treatment of diseases or disorders associated with or resulting from hyperlipidemia, hyper-lipoproteinemia, and/or dyslipidemia, including, but not limited to, cardiovascular diseases or disorders, such as atherosclerosis, atherosclerotic cardiovascular disease, angina, stroke, cerebrovascular diseases, congestive heart failure, coronary artery diseases, myocardial infarction, peripheral vascular diseases, and the like.

Pharmaceutical Compositions

In another aspect, the present invention provides compositions comprising compounds of the invention, such as the monovalent antibodies or antigen-binding fragment thereof as described herein. For example, the invention provides a pharmaceutical composition that comprises one or more monovalent antibodies of the invention, formulated together with a pharmaceutically acceptable carrier.

Accordingly, one aspect of the invention is to provide a pharmaceutical composition comprising such a monovalent antibody or antigen-binding fragment which is present in a concentration from 0.25 mg/ml to 250 mg/ml, such as 1 mg/ml to 250 mg/ml, such as 25 mg/ml to 250 mg/ml, and wherein said composition has a pH from 4.0 to 9.0. The composition may further comprise one or more of a buffer system, a preservative, a tonicity agent, a chelating agent, a stabilizer, or a surfactant, as well as various combinations thereof. The use of preservatives, isotonic agents, chelating agents, stabilizers and surfactants in pharmaceutical compositions is well-known to the skilled person. Reference may be made to Remington: The Science and Practice of Pharmacy, 19th edition, 1995.

In one embodiment the pharmaceutical composition is an aqueous composition. Such a composition is typically a solution or a suspension, but may also include colloids, dispersions, emulsions, and multi-phase materials. The term "aqueous composition" is defined as a composition comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical composition is a freeze-dried composition, to which a solvent and/or a diluent is added prior to use.

In a further aspect, the pharmaceutical composition comprises an aqueous solution of a monovalent antibody or antigen-binding fragment thereof, and a buffer, wherein the antibody is present in a concentration of 1 mg/ml or above, and wherein said composition has a pH from about 5.0 to about 8.0.

In a further aspect, the pharmaceutical composition comprises an aqueous solution of a monovalent antibody or antigen-binding fragment thereof, and a buffer, wherein the antibody is present in a concentration of 1 mg/ml to 150 mg/ml, and wherein said composition has a pH from about 5.0 to about 8.0.

In one such embodiment the monovalent antibodies or antigen-binding fragments thereof may be prepared in compositions, wherein the concentration of the antibody or antigen-binding fragment thereof is 50 mg/ml or more. in one embodiment the monovalent antibodies or antigen-binding fragments thereof may be prepared in compositions, wherein the concentration of the antibody or antigen-binding fragment thereof is 60 mg/ml or more. In one embodiment the monovalent antibodies or antigen-binding fragments thereof may be prepared in compositions, wherein the concentration of the antibody or antigen-binding fragment thereof is 70 mg/ml or more. in one embodiment the monovalent antibodies or antigen-binding fragments thereof may be prepared in compositions, wherein the concentration of the antibody or antigen-binding fragment thereof is 80 mg/ml or more. In one embodiment the monovalent antibodies or antigen-binding fragments thereof may be prepared in compositions, wherein the concentration of the antibody or antigen-binding fragment thereof is 90 mg/ml or more. In one embodiment the monovalent antibodies or antigen-binding fragments thereof may be prepared in compositions, wherein the concentration of the antibody or antigen-binding fragment thereof is 100 mg/ml or more. In one embodiment the monovalent antibodies or antigen-binding fragments thereof may be prepared in compositions, wherein the concentration of the antibody or antigen-binding fragment thereof is 110 mg/ml or more. In one embodiment the monovalent antibodies or antigen-binding fragments thereof may be prepared in compositions, wherein the concentration of the antibody or antigen-binding fragment thereof is 120 mg/ml or more. in one embodiment the monovalent antibodies or antigen-binding fragments thereof may be prepared in compositions, wherein the concentration of the antibody or antigen-binding fragment thereof is 130 mg/ml or more. In one embodiment the monovalent antibodies or antigen-binding fragments thereof may be prepared in compositions, wherein the concentration of the antibody or antigen-binding fragment thereof is 140 mg/ml or more.

In one embodiment the monovalent antibodies or antigen-binding fragments thereof may be prepared in compositions, wherein the concentration of the antibody or antigen-binding fragment thereof is 150 mg/ml or more.

In one embodiment, the present invention relates to an injection device with content of said composition. In some embodiments the pharmaceutical composition of the invention is intended for use and/or contained in an injection device. In some embodiments, the injection device is a disposable, pre-filled, multi-dose pen of the FlexTouch® type (supplier Novo Nordisk A/S, Denmark). In some embodiments the injection device is a single shot device.

In some embodiments the injection device is a fixed dose device, such as one configured to deliver multiple predetermined doses of a drug, sometimes referred to as a multiple fixed dose device or a fixed dose, multi-shot device.

Administration and Dosages

The monovalent antibodies or antigen-binding fragment thereof as disclosed herein, may be administered parenterally, such as intravenously, such as intramuscularly, such as subcutaneously. In a preferred embodiment the antibody or antigen-binding fragment thereof is administered subcutaneously. The monovalent antibody or antigen-binding fragment thereof may be administered prophylactically. The monovalent antibody or antigen-binding fragment thereof may be administered therapeutically (on demand).

The dose of the compounds to be delivered may be from about 0.01 mg to 500 mg of the compound per day.

A suitable dose may also be adjusted for a particular compound based on the properties of that antibody, including its in vivo plasma half-life or mean residence time and its biological activity.

The compositions containing the monovalent antibody or antigen-binding fragment thereof as disclosed herein can be administered for prophylactic and/or in some embodiments therapeutic treatments. In therapeutic applications, pharmaceutical compositions such as those disclosed herein are administered to a subject already suffering from a disease, such as any of those described herein, in an amount sufficient to cure, alleviate or partially arrest the disease and its complications. An amount adequate to accomplish this is defined as "therapeutically effective amount". Amounts effective for this purpose will depend on the severity of the disease or injury as well as the weight and general state of the subject, as will be understood by the person skilled in the art.

Embodiments

In one embodiment, the monovalent antibodies or antigen-binding fragments thereof as disclosed herein provide a viscosity in solution, which is lower than that of the corresponding bivalent antibodies (comprising identical heavy chains).

In one embodiment, the monovalent antibodies or antigen-binding fragments thereof as disclosed herein provide physical stability in solution, which is higher than that of corresponding bivalent antibodies (comprising identical heavy chains).

In one embodiment, the monovalent antibodies or antigen-binding fragments thereof provide a viscosity and self-association tendency across a broad pH interval; which are lower than that of corresponding bivalent antibodies (comprising identical heavy chains).

In one embodiment, the monovalent antibodies are those designated tmAb1 or an antigen-binding fragment thereof, tmAb2 or an antigen-binding fragment thereof, tmAb3 or an antigen-binding fragment thereof and tmAb4 or an antigen-binding fragment thereof.

The invention is further described by the following embodiments:

1. A monovalent antibody or antigen-binding fragment thereof capable of binding human ANGPTL3 (hANGPTL3) (SEQ ID NO:1),
wherein said antibody or antigen-binding fragment thereof has a $K_D(pH6)/K_D(pH7.4)$ value, defined as the ratio of $K_D$ for the antigen at pH6 and $K_D$ for the antigen at pH 7.4, of 40 or higher, such as 50, 60, 70, 80, 90, 95, 100, 105, 110, 120, 130, 140, 150, 160, 165, 166, 170, 180, 190, 200 or higher, and
wherein said antibody or antigen-binding fragment thereof is capable of reducing the concentration of hANGPTL3 in human plasma.

2. The antibody or antigen-binding fragment thereof according to embodiment 1 wherein said antibody or antigen-binding fragment thereof has a $K_D(pH6)/K_D(pH7.4)$ value, defined as the ratio of $K_D$ for the antigen at pH6 and $K_D$ for the antigen at pH7.4, in the range 90-105 such as 90, 91, 92, 93, 94, 95, 96, 97, 98, 99, 100, 101, 102, 103, 104 or 105.

3. The antibody or antigen-binding fragment thereof according to any of the previous embodiments, wherein the antibody or antigen-binding fragment thereof comprises a region that can interact with cell surface Fc receptors.

4. The antibody or antigen-binding fragment thereof according to any of the previous embodiments, wherein the antibody or antigen-binding fragment thereof comprises an Fc region, such as one or two Fc regions.

5. The antibody or antigen-binding fragment thereof according to any of the previous embodiments wherein the antibody isotype is IgG and wherein at least one negatively charged or neutral surface exposed amino acid residue in the $C_H2$ or $C_H3$ domain is substituted with a positively charged amino acid residue such to increase the isoelectric point of the antibody or antigen-binding fragment thereof as determined using isoelectric focussing.

6. The antibody or antigen-binding fragment thereof according to any of the previous embodiments wherein the antibody isotype is IgG and comprises arginine (R) in positions 311 and/or 343 in the heavy chain(s) (EU residues).

7. The antibody or antigen-binding fragment thereof according to any of the previous embodiments wherein the antibody isotype is IgG and comprises arginine (R) in positions 311 and 343 in the heavy chain(s) (EU residues).

8. The antibody or antigen-binding fragment thereof according to any of the previous embodiments wherein the antibody isotype is IgG and wherein the Fc region is modified such to enhance binding to FcγRIIb.

9. The antibody or antigen-binding fragment thereof according to any of the previous embodiments wherein said antibody or antigen-binding fragment thereof comprises one or more of tyrosine (Y) in position 234, aspartate (D) in position 238, valine (V) in position 250, isoleucine (I) in position 264, proline (P) in position 307, and/or lysine (K) in position 330, in the heavy chain(s) (EU residues).

10. The antibody or antigen-binding fragment thereof according to any of the previous embodiments wherein said antibody or antigen-binding fragment thereof comprises tyrosine (Y) in position 234, aspartate (D) in position 238, valine (V) in position 250, isoleucine (I) in position 264, proline (P) in position 307, and lysine (K) in position 330, in the heavy chain(s) (EU residues).

11. The antibody or antigen-binding fragment thereof according to any of the previous embodiments wherein the antibody isotype is IgG and wherein the Fc region is modified such to enhance binding to FcRn.

12. The antibody or antigen-binding fragment thereof according to any of the previous embodiments wherein said antibody or antigen-binding fragment thereof comprises tyrosine (Y) in position 252, threonine (T) in position 254, and glutamate (E) in position 256, in the heavy chain(s) (EU residues).

13. The antibody or antigen-binding fragment thereof according to any of the previous embodiments wherein said antibody or antigen-binding fragment thereof is capable of reducing hANGPTL3-mediated inhibition of Lipoprotein lipase (LPL).

14. The antibody or antigen-binding fragment thereof according to any of the previous embodiments wherein said antibody or antigen-binding fragment thereof is an antagonist capable of inhibiting hANGPTL3-mediated inhibition of Lipoprotein lipase (LPL).

15. The antibody or antigen-binding fragment thereof according to any of the previous embodiments wherein said antibody or antigen-binding fragment thereof is capable of reducing the concentration of hANGPTL3 in human plasma.

16. The antibody or antigen-binding fragment thereof according to any of the previous embodiments wherein said antibody or antigen-binding fragment thereof is an antagonist capable of inhibiting hANGPTL3-mediated inhibition of Lipoprotein lipase (LPL) and capable of reducing the concentration of hANGPTL3 in human plasma.

17. The antibody or antigen-binding fragment thereof according to any of the previous embodiments wherein
a) the heavy chain of said antibody or antigen-binding fragment thereof comprises:
a CDR1 sequence of amino acid residues SYWMT (SEQ ID NO:2), wherein none or one of these amino acid residues may be substituted by a different amino acid residue, and
a CDR2 sequence of amino acid residues SISSHSTYIYYADSVKG (SEQ ID NO:3), wherein none, one, two or three of these amino acid residues may be substituted by a different amino acid residue, and
a CDR3 sequence of amino acid residues EGWYDNWFDP (SEQ ID NO:4), wherein none, one, two or three of these amino acid residues may be substituted by a different amino acid residue; or
b) the heavy chain of said antibody or antigen-binding fragment thereof comprises:
a CDR1 sequence of amino acid residues SYWMT (SEQ ID NO:24), wherein none or one of these amino acid residues may be substituted by a different amino acid residue, and
a CDR2 sequence of amino acid residues SISSHSTYIYYADSVKG (SEQ ID NO:25), wherein none, one, two or three of these amino acid residues may be substituted by a different amino acid residue, and
a CDR3 sequence of amino acid residues EGWYDNWNDP (SEQ ID NO:26), wherein none, one, two or three of these amino acid residues may be substituted by a different amino acid residue;
and wherein the light chain of said antibody or antigen-binding fragment thereof comprises:
a CDR1 sequence of amino acid residues RASQNIRSPYLA (SEQ ID NO:9), wherein none, one, two or three of these amino acid residues may be substituted with a different amino acid residue, and
a CDR2 sequence of amino acid residues GVSSRAA (SEQ ID NO:10), wherein none, one or two of these amino acid residues may be substituted with a different amino acid residue, and
a CDR3 sequence of amino acid residues QQYDDHPYT (SEQ ID NO:11), wherein none, one or two of these amino acid residues may be substituted with a different amino acid residue.

18. The antibody or antigen-binding fragment thereof according to embodiment 17 wherein said substitution(s) is/are a conservative substitution(s).

19. The antibody or antigen-binding fragment thereof according to any of the previous embodiments wherein the heavy chain of said antibody or antigen-binding fragment thereof comprises:
a CDR1 sequence of amino acid residues SYWMT (SEQ ID NO:2), and
a CDR2 sequence of amino acid residues SISSHSTYIYYADSVKG (SEQ ID NO:3), and
a CDR3 sequence of amino acid residues EGWYDNWFDP (SEQ ID NO:4); and
wherein the light chain of said antibody or antigen-binding fragment thereof comprises:
a CDR1 sequence of amino acid residues RASQNIRSPYLA (SEQ ID NO:9), and
a CDR2 sequence of amino acid residues GVSSRAA (SEQ ID NO:10), and
a CDR3 sequence of amino acid residues QQYDDHPYT (SEQ ID NO:11).

20. The antibody or antigen-binding fragment thereof according to any of the previous embodiments wherein the heavy chain variable domain has at least 90, 91, 92, 93, 94, 95, 96, 97, 98 or 99% identity to SEQ ID NO:5, and the light chain variable domain has at least 90, 91, 92, 93, 94, 95, 96, 97, 98 or 99% identity to SEQ ID NO:12.

21. The antibody or antigen-binding fragment thereof according to any of the previous embodiments wherein
a) the heavy chain variable domain comprises SEQ ID NO:5 and the light chain variable domain comprises SEQ ID NO:12, or
b) the heavy chain variable domain comprises SEQ ID NO:17 and the light chain variable domain comprises SEQ ID NO:12, or
c) the heavy chain variable domain comprises SEQ ID NO:22 and the light chain variable domain comprises SEQ ID NO:12, or
d) the heavy chain variable domain comprises SEQ ID NO:27 and the light chain variable domain comprises SEQ ID NO:12.

22. A monovalent antibody or antigen-binding fragment thereof capable of binding hANGPTL3 (SEQ ID NO:1) wherein
a) the heavy chain of said antibody or antigen-binding fragment thereof comprises:
a CDR1 sequence of amino acid residues SYWMT (SEQ ID NO:2), wherein none or one of these amino acid residues may be substituted by a different amino acid residue, and
a CDR2 sequence of amino acid residues SISSHSTYIYYADSVKG (SEQ ID NO:3), wherein none, one, two or three of these amino acid residues may be substituted by a different amino acid residue, and
a CDR3 sequence of amino acid residues EGWYDNWFDP (SEQ ID NO:4), wherein none, one, two or three of these amino acid residues may be substituted by a different amino acid residue; or
b) the heavy chain of said antibody or antigen-binding fragment thereof comprises:
a CDR1 sequence of amino acid residues 31 to 35 (SYWMT) of SEQ ID NO:24, wherein none or one of these amino acid residues may be substituted by a different amino acid residue, and
a CDR2 sequence of amino acid residues 50 to 66 (SISSHSTYIYYADSVKG) of SEQ ID NO:25, wherein none, one, two or three of these amino acid residues may be substituted by a different amino acid residue, and
a CDR3 sequence of amino acid residues 99 to 110 (EGWYDNWNDP) of SEQ ID NO:26, wherein none, one, two or three of these amino acid residues may be substituted by a different amino acid residue;
and wherein the light chain of said antibody or antigen-binding fragment thereof comprises:
a CDR1 sequence of amino acid residues RASQNIRSPYLA (SEQ ID NO:9), wherein none, one, two or three of these amino acid residues may be substituted with a different amino acid residue, and
a CDR2 sequence of amino acid residues GVSSRAA (SEQ ID NO:10), wherein none, one or two of these amino acid residues may be substituted with a different amino acid residue, and
a CDR3 sequence of amino acid residues QQYDDHPYT (SEQ ID NO:11), wherein none, one or two of these amino acid residues may be substituted with a different amino acid residue.

23. The antibody or antigen-binding fragment thereof according to embodiment 22 wherein said substitution(s) is/are a conservative substitution(s).
24. The antibody or antigen-binding fragment thereof according to any of embodiments 17-23 wherein the antibody or antigen-binding fragment thereof comprises a region that can interact with cell surface Fc receptors.
25. The antibody or antigen-binding fragment thereof according to any of embodiments 17-24, wherein the antibody or antigen-binding fragment thereof comprises an Fc region.
26. The antibody or antigen-binding fragment thereof according to any of embodiments 17-24 wherein said antibody or antigen-binding fragment thereof is capable of reducing hANGPTL3-mediated inhibition of Lipoprotein lipase (LPL).
27. The antibody or antigen-binding fragment thereof according to any of embodiments 17-24 wherein said antibody or antigen-binding fragment thereof is an antagonist capable of inhibiting hANGPTL3-mediated inhibition of Lipoprotein lipase (LPL).
28. The antibody or antigen-binding fragment thereof according to any of embodiments 17-24 wherein said antibody or antigen-binding fragment thereof is capable of reducing the concentration of hANGPTL3 in human plasma.
29. The antibody or antigen-binding fragment thereof according to any of embodiments 17-24 wherein said antibody or antigen-binding fragment thereof is an antagonist capable of inhibiting hANGPTL3-mediated inhibition of Lipoprotein lipase (LPL) and capable of reducing the concentration of hANGPTL3 in human plasma
30. The monovalent antibody or antigen-binding fragment thereof according to any of the previous embodiments wherein the heavy chain of said antibody or antigen-binding fragment thereof comprises:
   a CDR1 sequence of amino acid residues SYWMT (SEQ ID NO:2), and
   a CDR2 sequence of amino acid residues SISSHSTYIYYADSVKG (SEQ ID NO:3), and
   a CDR3 sequence of amino acid residues EGWYDNWFDP (SEQ ID NO:4); and
wherein the light chain of said antibody or antigen-binding fragment thereof comprises:
   a CDR1 sequence of amino acid residues RASQNIRSPYLA (SEQ ID NO:9), and
   a CDR2 sequence of amino acid residues GVSSRAA (SEQ ID NO:10), and
   a CDR3 sequence of amino acid residues QQYDDHPYT (SEQ ID NO:11).
31. The antibody or antigen-binding fragment thereof according to any of embodiments 22-30 wherein the heavy chain variable domain has at least 90, 91, 92, 93, 94, 95, 96, 97, 98 or 99% identity to SEQ ID NO:5, 17, 22, 27 or 32, and the light chain variable domain has at least 90, 91, 92, 93, 94, 95, 96, 97, 98 or 99% identity to SEQ ID NO:12.
32. The antibody or antigen-binding fragment thereof according to any of embodiments 22-31 wherein the heavy chain variable domain comprises SEQ ID NO:5 and the light chain variable domain comprises SEQ ID NO:12.
33. The antibody or antigen-binding fragment thereof according to any of the previous embodiments wherein the isotype of said antibody is IgG1, IgG2, IgG3 or IgG4.
34. The antibody or antigen-binding fragment thereof according to any of the previous embodiments wherein the isotype of said antibody is based on IgG1.
35. The antibody or antigen-binding fragment thereof according to any of the previous embodiments wherein the isotype of said antibody is based on IgG1, wherein glycine and/or lysine in positions 446 and/or 447 in the heavy chain(s) (EU residues), respectively, is/are deleted.
36. The antibody or antigen-binding fragment thereof according to any of the previous embodiments wherein the isotype of said antibody truncated heavy chain is based on IgG1, wherein glycine and lysine in positions 446 and/or 447 in the heavy chain(s) (EU residues), respectively, is/are deleted.
37. The antibody or antigen-binding fragment thereof according to any of embodiments 17-36 wherein the antibody isotype is IgG and wherein at least one negatively charged or neutral surface exposed amino acid residue in the $C_H2$ or $C_H3$ domain is substituted with a positively charged amino acid residue such to increase the isoelectric point of the antibody or antigen-binding fragment thereof as determined using isoelectric focussing.
38. The antibody or antigen-binding fragment thereof according to any of embodiments 17-37 wherein said antibody or antigen-binding fragment thereof comprises arginine (R) in positions 311 and/or 343 in the heavy chain(s) (EU residues).
39. The antibody or antigen-binding fragment thereof according to any of embodiments 17-38 wherein said antibody or antigen-binding fragment thereof comprises arginine (R) in positions 311 and 343 in the heavy chain(s) (EU residue).
40. The antibody or antigen-binding fragment thereof according to any of embodiments 17-39 wherein the antibody isotype is IgG and wherein the Fc region is modified such to enhance binding to FcγRIIb.
41. The antibody or antigen-binding fragment thereof according to any of embodiments 17-40 wherein said antibody or antigen-binding fragment thereof comprises one or more of tyrosine (Y) in position 234,
aspartate (D) in position 238,
valine (V) in position 250,
isoleucine (I) in position 264,
proline (P) in position 307, and
lysine (K) in position 330,
in the heavy chain(s) (EU residues).
42. The antibody or antigen-binding fragment thereof according to any of embodiments 17-41 wherein said antibody or antigen-binding fragment thereof comprises
tyrosine (Y) in position 234,
aspartate (D) in position 238,
valine (V) in position 250,
isoleucine (I) in position 264,
proline (P) in position 307, and
lysine (K) in position 330,
in the heavy chain(s) (EU residues).
43. The antibody or antigen-binding fragment thereof according to any of embodiments 17-42 wherein the antibody isotype is IgG and wherein the Fc region is modified such to enhance binding to FcRn.

44. The antibody or antigen-binding fragment thereof according to any of embodiments 17-43 wherein said antibody or antigen-binding fragment thereof comprises
tyrosine (Y) in position 252,
threonine (T) in position 254, and
glutamate (E) in position 256,
in the heavy chain(s) (EU residues).
45. The antibody or antigen-binding fragment thereof according to any of the previous embodiments comprising a first and a second heavy chain each comprising a multimerization domain, wherein the sequence of said heavy chains are different and wherein said heavy chains multimerize by interaction of said multimerization domains.
46. The antibody or antigen-binding fragment thereof according to any of the previous embodiments wherein said antibody comprises a first and a second heavy chain, wherein said first heavy chain comprises
tryptophan (W) in position 366, and
wherein said second heavy chain comprises
serine (S) in position 366,
alanine (A) in position 368, and
valine (V) in position 407 (EU residues).
47. The antibody or antigen-binding fragment thereof according to any of the previous embodiments wherein said antibody comprises a first and a second heavy chain, wherein said first and second heavy chain comprises lysine (K) in position 214 (EU residues).
48. The antibody or antigen-binding fragment thereof according to any of the previous embodiments wherein said antibody comprises a first and a second heavy chain, wherein said first and second heavy chains comprise
lysine (K) in position 214,
arginine (R) in positions 311 and 343,
tyrosine (Y) in position 234,
aspartate (D) in position 238,
valine (V) in position 250,
isoleucine (I) in position 264,
proline (P) in position 307,
lysine (K) in position 330,
tyrosine (Y) in position 252,
threonine (T) in position 254,
glutamate (E) in position 256, and
wherein said first heavy chain further comprises
tryptophan in position 366, and
wherein said second heavy chain further comprises
serine in position 366,
alanine in position 368,
valine in position 407, and
optionally wherein glycine and lysine in positions 446 and/or 447, respectively, of said first and/or second heavy chain is/are deleted (EU residues).
49. The antibody according to any of the previous embodiments wherein said antibody comprises a first heavy chain according to SEQ ID NO:6 and a second heavy chain according to SEQ ID NO:7 or 8, and a single light chain according to SEQ ID NO:13.
50. A monovalent antibody or antigen-binding fragment thereof capable of binding human ANGPTL3 (hANGPTL3) (SEQ ID NO:1), comprising a first heavy chain, a second heavy chain and a light chain,
wherein the first heavy chain comprises SEQ ID NO:6, the second heavy chain comprises SEQ ID NO:7 and the light chain comprises SEQ ID NO:13.
51. The antibody or antigen-binding fragment thereof according to any of the previous embodiments wherein said antibody or antigen-binding fragment thereof is capable of pH-dependent binding to hANGPTL3.
52. The antibody or antigen-binding fragment thereof according to any of the previous embodiments wherein said antibody or antigen-binding fragment thereof is capable of reducing the size of immune complexes formed between said antibody or antigen-binding fragment thereof and hANGPTL3.
53. The antibody or antigen-binding fragment thereof according to any of the previous embodiments wherein said antibody or antigen-binding fragment thereof is capable of increasing the homogeneity of immune complexes formed between said antibody or antigen-binding fragment thereof and hANGPTL3.
54. The antibody or antigen-binding fragment thereof according to any of the previous embodiments wherein said antibody or antigen-binding fragment thereof is capable of reducing the hANGPTL3 plasma concentration.
55. The antibody or antigen-binding fragment thereof according to any of the previous embodiments wherein said antibody or antigen-binding fragment thereof is capable of reducing triglyceride concentration in plasma without increasing the hANGPTL3 plasma concentration.
56. The antibody or antigen-binding fragment thereof according to any of the previous embodiments wherein the said antibody or antigen-binding fragment thereof is humanized or human.
57. The antibody or antigen-binding fragment thereof according to any of the previous embodiments wherein said antibody or antigen-binding fragment thereof is a one-armed antibody.
58. The antibody or antigen-binding fragment thereof according to any of the previous embodiments wherein said antibody or antigen-binding fragment thereof has cross-species reactivity.
59. The antibody or antigen-binding fragment thereof according to embodiment 58 wherein said antibody or antigen-binding fragment thereof is capable of binding mouse ANGPTL3, rat ANGPTL3, pig ANGPTL3, canine ANGPTL3 and/or cynomolgus monkey ANGPTL3.
60. A pharmaceutical composition comprising the antibody or antigen-binding fragment thereof according to any of the previous embodiments and one or more pharmaceutically acceptable carrier(s).
61. The antibody or antigen-binding fragment thereof according to any of embodiments 1-59 or the composition according to embodiment 60 for use in medicine.
62. The antibody or antigen-binding fragment thereof according to any of embodiments 1-59 or the composition according to embodiment 60 for use in the treatment or prevention of elevated triglyceride concentration in human plasma.
63. The antibody or antigen-binding fragment thereof according to any of embodiments 1-59 or the composition according to embodiment 60 for use in suppressing elevation of a triglyceride concentration in human plasma.
64. A method of treating a patient with elevated triglyceride concentration in human plasma, comprising administering to said patient of the antibody or antigen-binding fragment thereof according to any of embodiments 1-59 or the composition according to embodiment 60.

65. A method of treating a patient with highly elevated triglyceride concentration in human plasma, comprising administering to said patient of the antibody or antigen-binding fragment thereof according to any of embodiments 1-59 or the composition according to embodiment 60.

66. A method of reducing triglyceride concentration in human plasma, comprising administering the antibody or antigen-binding fragment thereof according to any of embodiments 1-59 or the composition according to embodiment 60 to a patient in need thereof.

67. A method of suppressing elevation of the triglyceride concentration in plasma, comprising administering the antibody or antigen-binding fragment thereof according to any of embodiments 1-59 or the composition according to embodiment 60 to a patient in need thereof.

68. Use of an antibody or antigen-binding fragment thereof according to any of embodiments 1-59 or the composition according to embodiment 60 for the manufacture of a medicament for the treatment of a patient with elevated triglycerides.

69. Use of an antibody or antigen-binding fragment thereof according to any of embodiments 1-59 or the composition according to embodiment 60 for the manufacture of a medicament for the treatment of a patient with highly elevated triglycerides.

70. The use or method according to any of embodiments 61-69 or the composition according to embodiment 60 wherein the patient is diagnosed with atherosclerotic cardiovascular disease (ASCVD) and/or type 2 diabetes.

71. The antibody or antigen-binding fragment thereof according to any of embodiments 1-59 or the composition according to embodiment 60 for use in the treatment or prevention of cardiovascular disease.

72. The antibody or antigen-binding fragment thereof according to any of embodiments 1-59 or the composition according to embodiment 60 for use in the treatment or prevention of atherosclerotic cardiovascular disease (ASCVD).

73. A method of treatment or prevention of cardiovascular disease in a patient, comprising administering to said patient the antibody or antigen-binding fragment thereof according to any of embodiments 1-59 or the composition according to embodiment 60.

74. A method of treatment or prevention of atherosclerotic cardiovascular (ASCVD) disease in a patient, comprising administering to said patient the antibody or antigen-binding fragment thereof according to any of embodiments 1-59 or the composition according to embodiment 60.

75. Use of an antibody or antigen-binding fragment thereof according to any of embodiments 1-59 or the composition according to embodiment 60 for the manufacture of a medicament for the treatment or prevention of cardiovascular disease.

76. Use of an antibody or antigen-binding fragment thereof according to any of embodiments 1-59 or the composition according to embodiment 60 for the manufacture of a medicament for the treatment or prevention of atherosclerotic cardiovascular disease (ASCVD).

77. A kit comprising the antibody or antigen-binding fragment thereof according to any of embodiments 1-59 or the composition according to embodiment 60, and instructions for use.

78. The antibody or antigen-binding fragment thereof according to any of embodiments 45-48 wherein the first heavy chain is a truncated heavy chain.

79. The antibody or antigen-binding fragment thereof according to any of embodiments 45-50 wherein the second heavy chain is a truncated heavy chain.

EXAMPLES

List of Abbreviations

BSA: Bovine Serum Albumin
ELISA Enzyme Linked ImmunoSorbent Assay
hIgG Human Immunoglobulin G
HPC4: 12 amino acid sequence of Protein C
HPLC: High-Performance Liquid Chromatography
LPL: Lipoprotein lipase
LC (example 2): Light Chain
LC (example 3): Liquid Chromatography
LLOQ: Lower Limit of Quantification
LOCI: Luminescence Oxygen Channelling Immunoassay
MRT: Mean retention time
MS: Mass Spectrometry
$OD_{600}$: Optical Density at 600 nm
QC: Quality control
hANGPTL3: Human ANGPTL3
rhANGPTL3: Recombinant human ANGPTL3
P20: Polysorbate 20
PBS: Phopsphate Buffered Saline
PEG: Poly Ethylene Glycol
RT: Retention time
SE-HPLC: Size-Exclusion High-Performance Liquid Chromatography
SE-UPLC: Size-Exclusion Ultra-Performance Liquid Chromatography
SIA: Sequence Identical Analog
SPR: Surface Plasmon Resonance
ULOQ: Upper Limit of Quantification
UV-VIS: Ultraviolet-Visible Spectroscopy Example 1: Generation of pH-Dependent Antibody Variants Initial Human-Antibody Library A Human Fab library was constructed with highly stable framework and a diversity of over $10^{10}$ in CDR3s:

Phage Panning Initial Screen:

Biotinylated hANGPTL3 was coated on M280-streptavidin Dynabeads (Thermo Fisher Scientific #11205D). The phage display library (>1013 pfu/mL) was depleted for non-specific binders with non-coated streptavidin Dynabeads, followed by addition of the hANGPTL3 coated beads for binding at pH 7.4. After being washed ten times with PBS, 0.05% Tween20 and three times with PBS, the beads with ANGPLT3 bound phages were suspended in 1 mL PBS and mixed with 9 mL of actively growing *E. coli* XL-Blue culture ($OD_{600}$=0.6) in 2×YT media (2% glucose, 25 ug/ml chloramphenicol, 10 ug/ml tetracycline) and incubated at 37° C. for 30 minutes. All cells were centrifuged and resuspended in 24 cm×24 cm plates with 2×YT media at 37° C. overnight. *E. coli* cells were infected with M13K07 helper phages to amplify and produce phage. After 24 hours, *E. coli* cells were removed, and phages were harvested by precipitation with a PEG/NaCl solution followed by resuspension in PBS-buffer for the following rounds of panning.

Antibody Identification:

After 4 rounds of panning, single colonies were picked for Sanger sequencing and ELISA. The top hits were selected for gene synthesis in full antibody format. After expression and purification (See Example 2), the full antibodies were tested for ANGPTL3 binding at pH 7.4 and pH 6 by SPR analysis (See Example 7). The antibody mAb0 was identified as having the most ideal binding to hANGPTL3.

Construction of Library for Incorporation of pH Dependent Binding

To incorporate a pH-switch into the variable domain of mAb0 binding to ANGPTL3, a computational analysis was performed on homology models. Briefly, all mAb0 residues within a 7.5 Ångstrøms distance from a positively charged residue in the interface were identified. The identified positions were changed to histidine, another charged residue (positive or negative), or a stabilizing substitution e.g., prolines in turn. The amino acid substitutions stereochemistry and intramolecular interactions were evaluated computationally from a homology model. Next, a library was constructed using degenerate codons with 16 mutational sites with an approximate diversity of ~$10^7$.

Phage Panning for Identification of pH Dependent Variants of mAb0

Biotinylated hANGPTL3 was coated on M280-streptavidin Dynabeads. The produced phage library ($10^{12}$ pfu/mL) was depleted with non-coated streptavidin Dynabeads. The depleted phage library was added to hANGPTL3 (17-460) coated beads for binding at pH 7.4. After being washed three times with PBT and three times with PB, bound phages were eluted twice with elution buffer at pH 5.5, followed by 15 min incubation. The eluted phage particles were then amplified and subjected to additional rounds of screening.

The eluent was transferred into a 1.5 mL microfuge tube and neutralized with 1 M Tris-HCl (pH 8.0). Half of the neutralized phage solution was mixed with 1 mL of actively growing *E. coli* NEB 5-alpha F' ($OD_{600}$=0.8) in 2×YT media containing 10 μg/mL tetracycline and incubated at 37° C. for 1 hour. $1\times10^{10}$ pfu of M13K07 helper phages were added and incubated for 1 hour. The infected *E. coli* were amplified in 50 mL 2×YT medium containing 50 μg/mL carbenicillin and 25 μg/mL kanamycin, by shaking at 200 rpm and growing overnight at 37° C. The next day, phages were harvested by precipitation with PEG/NaCl solution and resuspension in PBS buffer for the following rounds of panning.

Identification of Antibodies Showing pH Dependent Binding of hANGPTL3

The phage pools from 3 rounds of panning were collected for next generation sequencing. The most enriched Abs sequences were selected for gene synthesis followed by expression and purification (see Example 2). The prepared antibodies were analyzed by SPR essentially as in Example 7. Full-length His6-tagged hANGPTL3 was captured by an anti-His antibody immobilized on the SPR sensor chip, and anti-hANGPTL3 antibodies were flowed through at pH 6.0 and pH 7.4, respectively. Antibodies with relatively weaker affinities at pH 6.0 than pH 7.4 were selected. Antibodies containing the variable domains of the heavy and light chains of tmAb0.1 and tmAb1 were identified using this approach. These antibodies retained inhibitory activity on hANGPTL3.

Example 2: Recombinant Expression of Antibodies or Fragments Hereof

Antibodies or fragments hereof were expressed using transient transfection of HEK293 suspension cells (293Expi, Invitrogen) essentially following manufacturer's instructions. 293Expi cells were typically subcultivated every 3-4 days in Expi293F expression medium (Invitrogen, catalogue number A1435104) supplemented with 1% P/S (GIBCO catalogue number 15140-122). Expi293F cells were transfected at a cell density of 2.5-3 mill/mL using Expifectamine. For each litre of Expi293F cells, the transfection was performed by diluting a total of 1 mg of plasmid DNA ($V_H$-$C_H$1 (for Fab) or (HC for mAb) and LC plasmids in 1:1 ratio) into 50 mL Optimem (GIBCO, cat. No. 51985-026, dilution A) and by diluting 2.7 mL Expifectamine into 50 mL Optimem (dilution B). For Fab and mAb producing co-transfections, $V_H$-$C_H$1 and LC plasmids (Fab) and HC and LC plasmids (mAb), respectively, were used in a 1:1 ratio. Dilution A and B were mixed and incubated at room temperature for 10-20 minutes. The transfection mix was hereafter added to the Expi293F cells and cells were incubated at 37° C. in a humidified incubator with orbital rotation (85-125 rpm). One day post-transfection, transfected cells were supplemented with 5 ml of ExpiFectamine 293 Transfection Enhancer 1 and 50 ml of ExpiFectamine 293 Transfection Enhancer 2. Cell culture supernatants were typically harvested 4-5 days post-transfection by centrifugation followed by filtration.

The expression of monovalent antibodies was performed essentially as described above, however, using co-transfection of 3 different plasmids. One-armed antibodies consist of one heavy chain (HC), one truncated heavy chain (tHC) and one LC and accordingly, transfections were setup using a DNA mixture of HC, tHC and LC plasmids in a 1:1:1 ratio.

The monovalent antibodies designated tmAb1, tmAb2, tmAb3 and tmAb4, comprise a HC, a tHC and a LC based on the human IgG1 kappa isotype. The constant regions of tmAb1-4 HC and tHC were engineered such to comprise the following substitutions compared to wild type IgG1: L234Y, P238D, T250V, M252Y, S254T, T256E, V264I, T307P, Q311R, A330K and P343R (EU residues). In order to ensure correct HC and tHC heterodimerization for efficient tmAb1-4 production, the knob-in-hole technology (US Patent Application 20030078385) was employed i.e. the T366W mutation (knob) was inserted into the HC and the T366S, L368A, Y407V mutations (hole) were inserted into the tHC or visa versa.

Example 3: Purification and Characterization of Antibodies or Fragments Hereof All purification steps were carried out at 4° C. For lab scale, Milli-Q water was used for buffer preparation. The HPLC system used for SE-HPLC analysis was Agilent 1100. Aggregation and LC/MS were assessed for QC.

Capturing of Fab was performed with HiTrap KappaSelect (Cytiva) affinity chromatography with binding buffer in 1×PBS (10 mM Na2HPO4, 1.8 mM KH2PO4, 137 mM NaCl, 2.7 mM KCl), pH 7.4. One step elution was performed with 0.1M Glycine, pH 2.8. Eluted Fabs were purified further and buffer-exchanged by size-exclusion chromatography on a 320 mL Superdex 200 26/60 column (Cytiva) into formulation buffer (20 mM HEPES, 150 mM NaCl) with pH 7.4 and concentrated by centrifugal ultrafilter (30$K_D$ C.O.) for storage at −80° C.

To assess the quality of the purified Fab, SDS-PAGE and high-performance size-exclusion chromatography (SE-HPLC) analysis were performed. LC/MS was carried out to verify the identity of Fab protein. Molecular weights (MWs) of all Fabs were shown to be consistent with theoretical MW of heavy chain and light chain, respectively.

Antibody Purification and Characterization

Purification of the antibodies was conducted by affinity chromatography using a Protein A MabSelect PrismA resin (Cytiva)). For small-scale antibody productions, protein A based purification was performed in 96-well plates, while for larger productions, the AktaXpress chromatography system (Cytiva) was used with an equilibration buffer composed of 20 mM NaPhosphate pH 7.2, 150 mM NaCl and an elution buffer composed of 10 mM Formic acid pH 3.5. Cell supernatants were applied directly without any adjustments onto a pre-equilibrated MabSelect SuRe column. The column was washed with approximately 5 column volumes of equilibration buffer and the antibodies were eluted isocratically in approx. 2-5 column volume of elution buffer. Eluted antibodies were applied directly on a 320 mL Superdex 200 26/60 column (Cytiva) for removal of aggregates and buffer-exchange into 20 mM HEPES, 150 mM NaCl pH 7.4

The purified antibodies were characterized using different methods such as SDS-PAGE/Coomassie, size-exclusion high-performance liquid-chromatography (SE-HPLC) and liquid-chromatography mass spectrometry (LC-MS) analyses. The SDS-PAGE/Coomassie analysis was performed using NuPage 4-12% Bis-Tris gels (Invitrogen, cat. no. NP0321 BOX). Here, all antibodies displayed expected light chain and heavy chain components. Intact molecular mass determinations were performed using a Liquid Chromatography Electrospray Ionisation Time-of-Flight Mass Spectrometry method setup on an Agilent 6210 instrument with a desalting column MassPREP (Waters, cat. no. USRM10008656). The buffer system used was an equilibration buffer composed of 0.1% Formic acid in LC-MS graded-$H_2O$ and an elution buffer composed of 0.1% formic acid in LC-MS graded Acetonitrile (ACN). Analyses were performed with and without N-Glycosidase F (Roche Diagnostics, cat. no. 11365177001) and reducing agent (i.e. mercaptoethanol or DTT). All antibodies displayed expected intact molecular masses in accordance with sequence and one heavy chain N-glycan. Purity was determined based on SE-HPLC. The final protein purity was analysed based on SE-HPLC method setup on an Agilent LC 1100/1200 system and using a BIOSep-SEC-53000 300×7.8 mm column (Phenomenex, cat. no. 00H-2146-KO) and a running buffer composed of 200 mM NaPhosphate pH 6.9, 300 mM NaCl and 10% isopropanol. UV280 and fluorescence (Ex 280 nm/Em 354 nm) detectors was used for detection. The antibodies eluted as single symmetric peaks with retention times reflecting the size of the antibodies. Purity estimates were all between 95-99% for the different antibodies. To measure the final protein concentrations, a NanoDrop spectrophotometer (Thermo Scientific) was used together with specific extinction coefficients for each of the antibodies.

Example 4: Assay to Determine Inhibition of rhANGPTL3-Mediated LPL Inhibition

Inhibition of hANGPTL3-mediated LPL inhibition was measured in a recombinant hANGPTL3-LPL assay. In this assay, the in vitro enzymatic activity of lipoprotein lipase (LPL) is measured using EnzChek™ Lipase as substrate. The activity of bovine LPL is inhibited by addition of recombinant hANGPTL3 (rhANGPTL3). This inhibition can then be blocked by rhANGPTL3 inhibitory compounds such as the anti-hANGPTL3 antibodies disclosed herein. The apparent affinities of the anti-hANGPTL3 antibodies were measured relative to Evinacumab SIA.

rhANGPTL3-LPL Enzymatic Activity Procedure

All solutions were made with Assay Buffer (DPBS(1×) (Gibco 14190-144)+1% fatty-acid free BSA (MP Biomedicals 05033)) except for the EnzChek™/Zwittergent reagent that was made with ultrapure water.

Dilution series of anti-rhANGPTL3 antibodies were prepared as follows. Starting concentration was 3 µM and a 3-fold dilution was made in Assay buffer. This was repeated 7 times to prepare a dilution series. The mixing of compounds for the analysis is described below.

Assay Buffer and 10 µL of each dilution were mixed with 10 µL 1.2 µM rhANGPTL3 (SEQ ID NO:1) and 10 µL 60 nM heparin (Sigma H3149) in an assay plate (96-well half-area black plates, Corning 3993) and pre-incubated at room temperature for 1 hour. After incubation, 10 µL 1.8 µM human ApoCII (Chemically synthesized residues 59-79) and 10 µL 60 nM bovine LPL (Sigma L2254) were added to each well and incubation continued for 15 minutes at room temperature. Finally, 10 µL EnzChek™/Zwittergent substrate (4.8 µM EnzChek™ Lipase (Thermo Fisher Scientific E33955), 0.03% Zwittergent 3-18 (Merck 41570) was added to each well and fluorescence was measured kinetically (every minute for 20 minutes) using excitation wavelength 485 nm and emission wavelength 535 nm in an Envision Multimode Plate Reader (PerkinElmer).

In addition to the diluted compounds, the plate also contained six wells where the compound was replaced by 10 µL Assay Buffer, and six wells where both the compound and rhANGPTL3 were replaced by 10 µL Assay Buffer each. These wells were used to establish the fully inhibited and the non-inhibited LPL activity levels, respectively. Additionally, the plate contained one well per compound using the next-to-highest compound concentration but without rhANGPTL3 to assess the effect of the anti-ANGPTL3 antibodies directly on LPL activity without the presence of rhANGPTL3.

Each plate contained a dilution series of evinacumab SIA in duplicate.

Statistical Analysis

The LPL activity in each well of the assay plates was calculated by performing a set of linear regressions over a window of 5 consecutive time points from the kinetic data, selecting the fit with the highest slope (Vmax) and a correlation of determination above 0.95, and calculating the slope of the selected line. The Vmax values were then normalized using the mean of Vmax from the six fully inhibited LPL activity control wells as the value 0 and the mean of the Vmax from the six non-inhibited LPL activity control wells as the value 1. The apparent affinity for rhANGPTL3 for the tested compounds were calculated from a non-linear 4-parameter logistic (4PL) curve fit of the normalized Vmax ~concentration data from the dilution series of the compounds. The fit was performed using the LL.4 function from the drc R package. The value 0 (i.e. the normalized mean of Vmax of the six fully inhibited LPL activity level control wells) was used as a common lower asymptote in the fitting. The apparent affinity of the compound was extracted from the 4PL fit as the "e" parameter, named $IC_{50}$, and the relative apparent affinity was calculated using the mean of the on-plate evinacumab SIA $IC_{50}$s as denominator. Further, for each compound it was determined that the normalized Vmax of the control well assessing the direct effect of the compound on LPL activity in the absence of rhANGPTL3 did not differ significantly from 1 (i.e. the mean of the normalized Vmax of the non-inhibited LPL activity control wells).

Results

Table 1 shows the average relative $IC_{50}$ and standard deviation of the rhANGPTL3-mediated LPL inhibition of five compounds. The number of replicates that form the basis for the averages are included for completeness. For evinacumab SIA, the average relative $IC_{50}$ is 1.0 per definition, but the standard deviation for the 58 replicates is calculated from the individual results. As tmAb4 was only analysed once the standard deviation could not be calculated. Relative to evinacumab SIA, the monovalent antibodies show similar or slightly reduced activity towards inhibition of rhANGPTL3, showed by the ratio of more than 1 when compared to the relative $IC_{50}$ value measured for evinacumab SIA.

TABLE 1

| Compound | Average relative $IC_{50}$ | Standard deviation | Number of replicates |
|---|---|---|---|
| evinacumab SIA | 1.0 | 0.15 | 58 |
| tmAb1 | 3.7 | 1.14 | 7 |
| tmAb2 | 2.5 | 0.70 | 3 |
| tmAb3 | 4.8 | 3.57 | 3 |
| tmAb4 | 1.3 | NA | 1 |

Example 5: In Vivo Evaluation of Anti-ANGPTL3 Antibodies in Normal Mice

A study to measure the effect of inhibiting ANGPTL3 on plasma triglyceride level and endogenous ANGPLT3 (250-300 µg/ml at T=0h) levels in healthy male C57bl6/6J mice from Janvier Labs, France using evinacumab SIA and monovalent anti-ANGPTL3 antibodies designated tmAb0.1, tmAb0.2, tmAb0.3 and tmAb0.4 was carried out as described below.

The monovalent antibodies tested, differ from tmAb1-4 in not being modified at positions 234, 238, 250, 252, 254, 256, 264, 307, 311, 330, 343 in the Fc region, i.e. comprising wild-type human IgG1 residues in said positions.

Wild-type human IgG1 residues in said positions (in particular 234L, 238P, 250T, 252M, 254S, 256T, 264V, 307T, 311Q, 330A, 343P) were used due to the lack of functionality of the Fc substitutions in the mouse. The effect of Fc substitutions as introduced in tmAb1-4 are specific to human receptors (see example 2).

Blood Sampling

From 12 mice in each group a blood sample was taken at 0h, 48h, 168h, 240h and 336h. Blood samples (120 µL) were taken by puncture of vena sublingualis (tongue blood) and transferred to EDTA coated tubes (Microvette® VetMed 200 K3E, Sarstedt nr 09.1293.100). The blood was centrifuged 5 minutes, 6000 G, 4° C. within 20 minutes. The plasma samples were transferred to micronic tubes, 25 µl for triglyceride measurement and µl for mANGPTL3 and hIgG measurements (antibody plasma exposure measurements).

Triglycerides were measured on a COBAS 6000 multi-analyser according to the manufacturer's recommendation (Roche Diagnostics).

Mouse plasma samples were analysed for mouse ANGPTL3 using an ELISA from R&D Systems (Mouse Angiopoietin-like 3 ELISA kit—Quantikine ELISA. Cat no. MANL30) according to kit protocol. The samples were diluted minimum 250× in calibrator diluent from the kit, to avoid a matrix effect. The assay range spans from 62.5-4000 pg/ml. Samples measured above ULOQ were diluted further in calibrator diluent. LLOQ was 15.625 pg/ml (250×62.5 pg/ml).

Analysis of Mouse ANGPTL3 in Mouse Plasma

Mouse plasma samples are analysed for mouse ANGPTL3 using an ELISA from R&D Systems (Mouse Angiopoietin-like 3 ELISA kit—Quantikine ELISA. Cat no. MANL30) according to kit protocol. The samples are diluted minimum 250× in calibrator diluent from the kit, to avoid matrix effect. The assay range spans from 62.5-4000 pg/ml. Samples measured above ULOQ are to be diluted further in calibrator diluent. LLOQ is 15.625 pg/ml (250×62.5 pg/ml).

Principle of LOCI Assay for Determination of Anti-ANGPTL3 Antibody Concentration Plasma samples are analysed for anti-ANGPTL3 antibodies (hIgG) using Luminescence Oxygen Channelling Immunoassay (LOCI). The donor beads are coated with streptavidin, while acceptor beads are conjugated with a first monoclonal mouse anti-human IgG Fc antibody (Southern Biotech, cat.no 9040-01) specific for the Fc region of the anti-ANGPTL3 antibodies. The other antibody used is polyclonal from goat and specific for the human IgG Fc region (Jackson ImmunoResearch, code:109-005-098). This polyclonal antibody is biotinylated in-house. The three reactants (donor beads with streptavidin, acceptor beads conjugated with target-specific Ab, and another biotinylated target-specific Ab) are combined with the anti-ANGPTL3 antibodies (hIgG) and form a two-sited immuno-complex. Illumination of the complex release singlet oxygen atoms from the donor beads. They are channelled into the acceptor beads and triggers chemiluminescence, which is measured by the EnVision plate reader. The amount of light is proportional to the concentration of anti-ANGPTL3 antibody (tmAb0.1).

Analysis of hIgG in Mouse Plasma

One µL of plasma sample/calibrator/control is applied to the wells of 384-well LOCI plates followed by a 15 µL mixture of acceptor beads (0.5 pg/well) coated with mAb anti-hIgG and biotinylated pAb anti-hIgG. The plates are incubated for 1 h at room temperature (RT). Then 30 µL streptavidin-coated donor-beads (2 pg/well) are added to each well and incubated for 30 minutes at RT. The plates are read in an Envision plate reader at 21-22° C. with a filter having a bandwidth of 520-645 nm after excitation by a 680 nm laser. The total measurement time per well is 210 ms including a 70 ms excitation time. The calibrator material is the anti-ANGPTL3 antibody diluted in mouse plasma (Untreated K2EDTA plasma, 0.22 µm filtrated from Bioreclamation). As the calibrator differ from antibody to antibody the lower limit of quantification is estimated from run to run (generally between 100-500 pM).

The assay range spans from 41-30.000 pM. The mouse samples are tested undiluted and diluted with 20× in mouse plasma. Samples measured above ULOQ are to be diluted further in mouse plasma.

Study groups in vivo study 1:
Gr. 1: 11 mice were dosed with vehicle (i.v.)
Gr. 2: 11 mice were dosed with evinacumab SIA 40 nmol/kg (i.v.)
Gr. 3: 11 mice were dosed with tmAb0.1 40 nmol/kg (i.v.)
Gr. 4: 11 mice were dosed with tmAb0.2 40 nmol/kg (i.v.)
Gr. 5: 11 mice were dosed with tmAb0.3 40 nmol/kg (i.v.)
Gr. 6: 11 mice were dosed with tmAb0.4 40 nmol/kg (i.v.)
Vehicle was 20 mM HEPES; 150 mM sodium chloride, pH=7.4; Injection volume was 5 ml/kg and the concentration of dosing solution 8 nmol/ml.

Results

TG Levels

Figure 3:
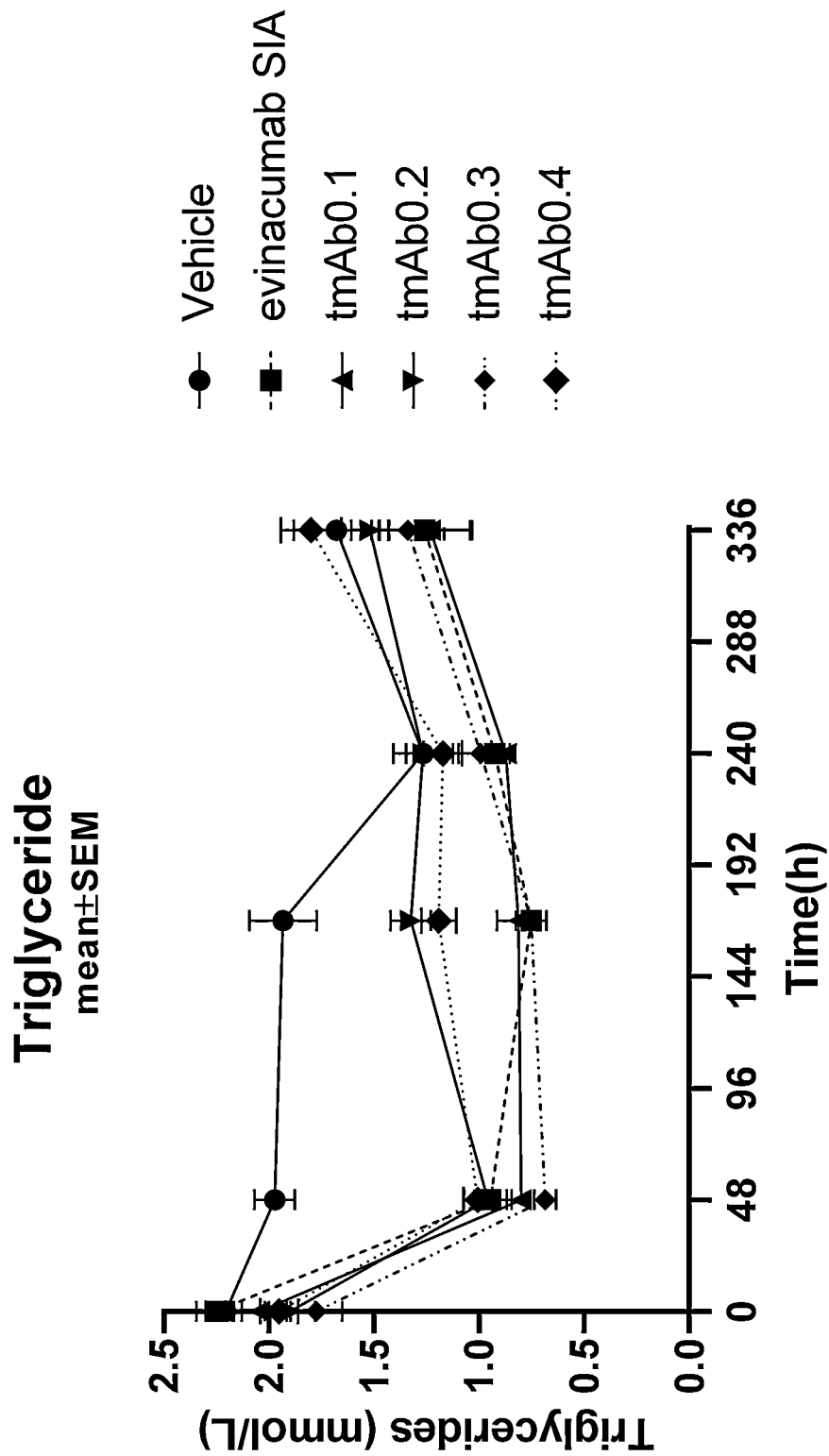
FIG. 3 shows the effect of administration of tmAb0.1, tmAb0.2, tmAb0.3, tmAb0.4 and an evinacumab sequence identical analogue (SIA) on triglyceride concentration in mouse plasma at various time points.

All antibodies lowered triglyceride (TG) level by 50-60% after 48 hours with evinacumab SIA and tmAb0.1 showing the highest capacity for TG lowering. Evinacumab SIA, tmAb0.1 and tmAb0.3 were still able to lower TG by 58-67% after 168 h, whereas the efficacy of tmAb0.2 and tmAb0.4 was less pronounced (31-38%). After 336 hours only, evinacumab SIA and tmAb0.1 were observed to significantly lower TG levels as compared to the vehicle group, both being 40-45% below baseline. See FIG. 3.

ANGPTL3 Levels

Figure 4A:
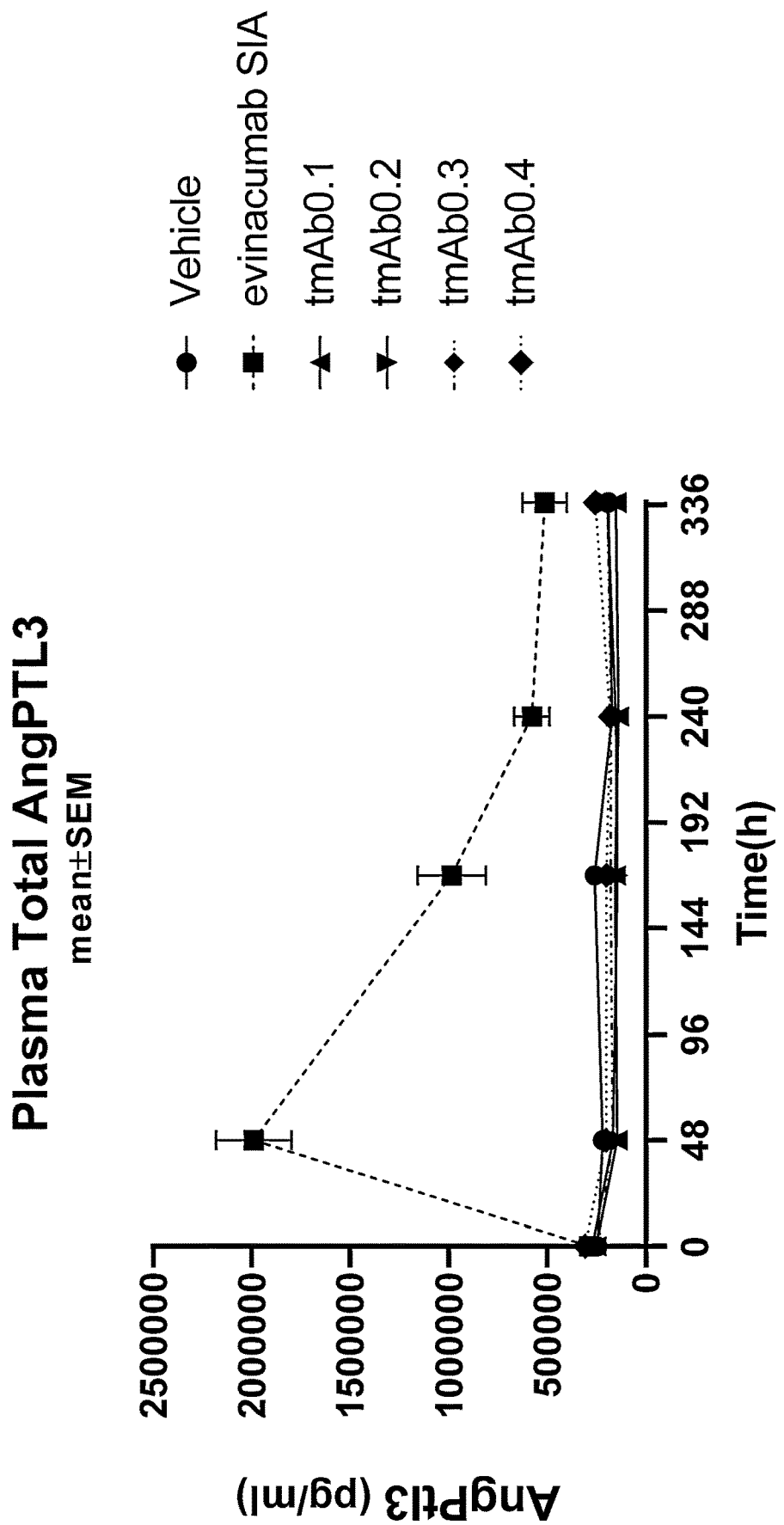

Evinacumab SIA increased plasma total ANGPTL3 levels approximately 10-fold from baseline after 48 hours, hereafter slowly declining towards baseline. In contrast, tmAb0.1, tmAb0.2, tmAb0.3 all decreased plasma total ANGPTL3 levels to or below baseline for the whole study period. See FIGS. 4A and 4B.

Antibody Levels

Figure 5:
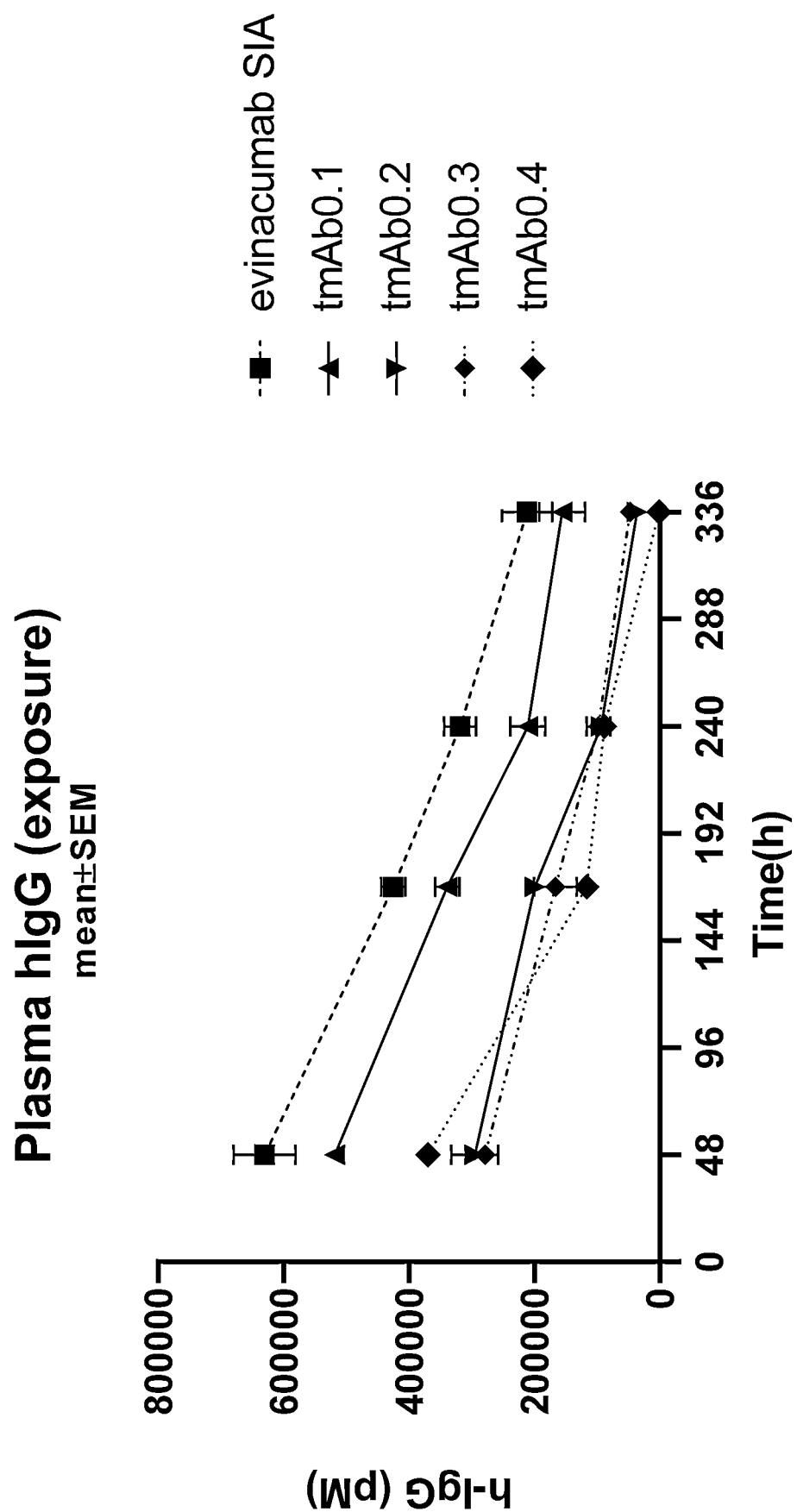
FIG. 5 shows the mouse plasma concentration of tmAb0.1, tmAb0.2, tmAb0.3 and tmAb0.4 and an evinacumab sequence identical analogue (SIA) following administration thereof.
Figure 6A:
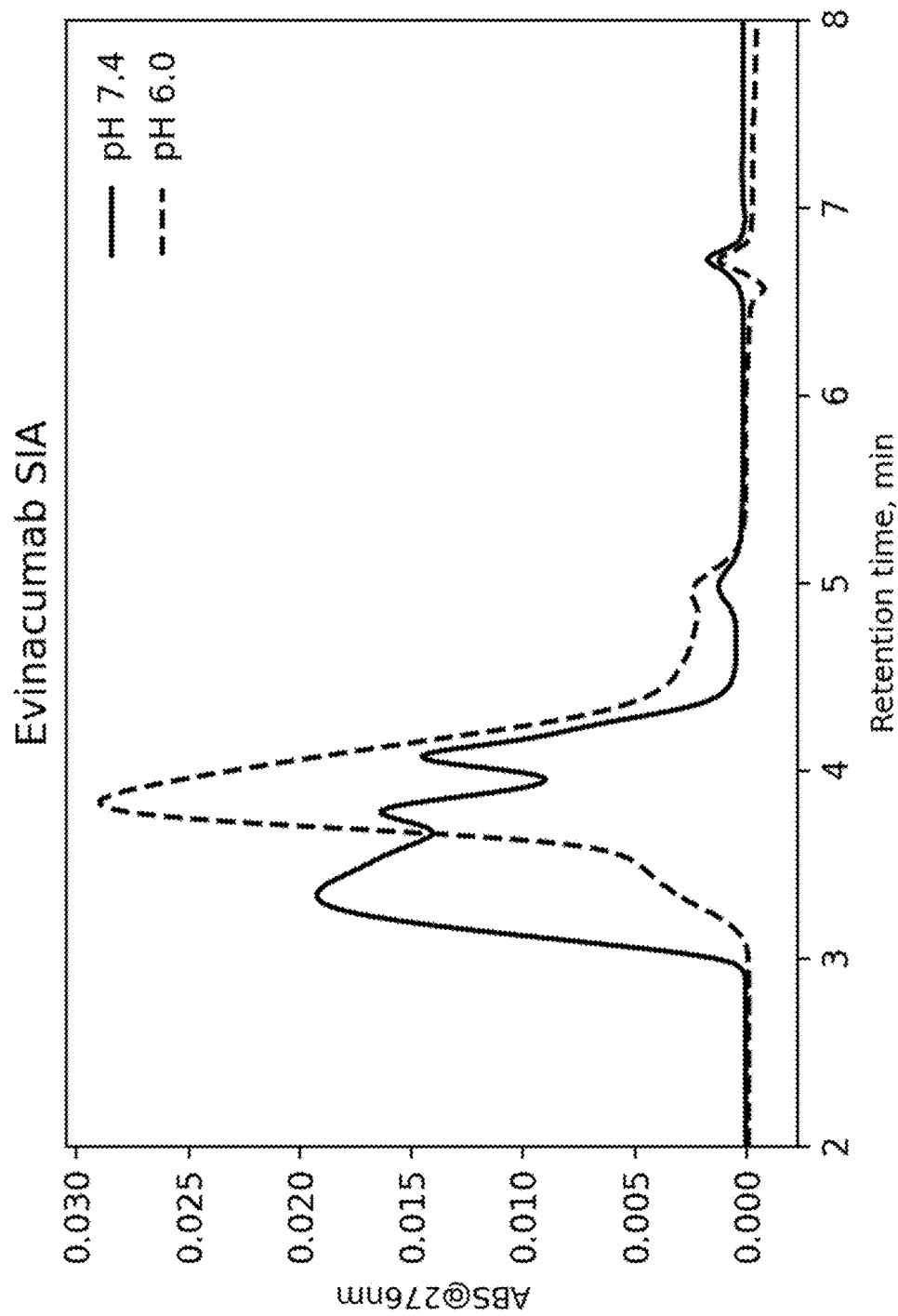
Figure 6B:
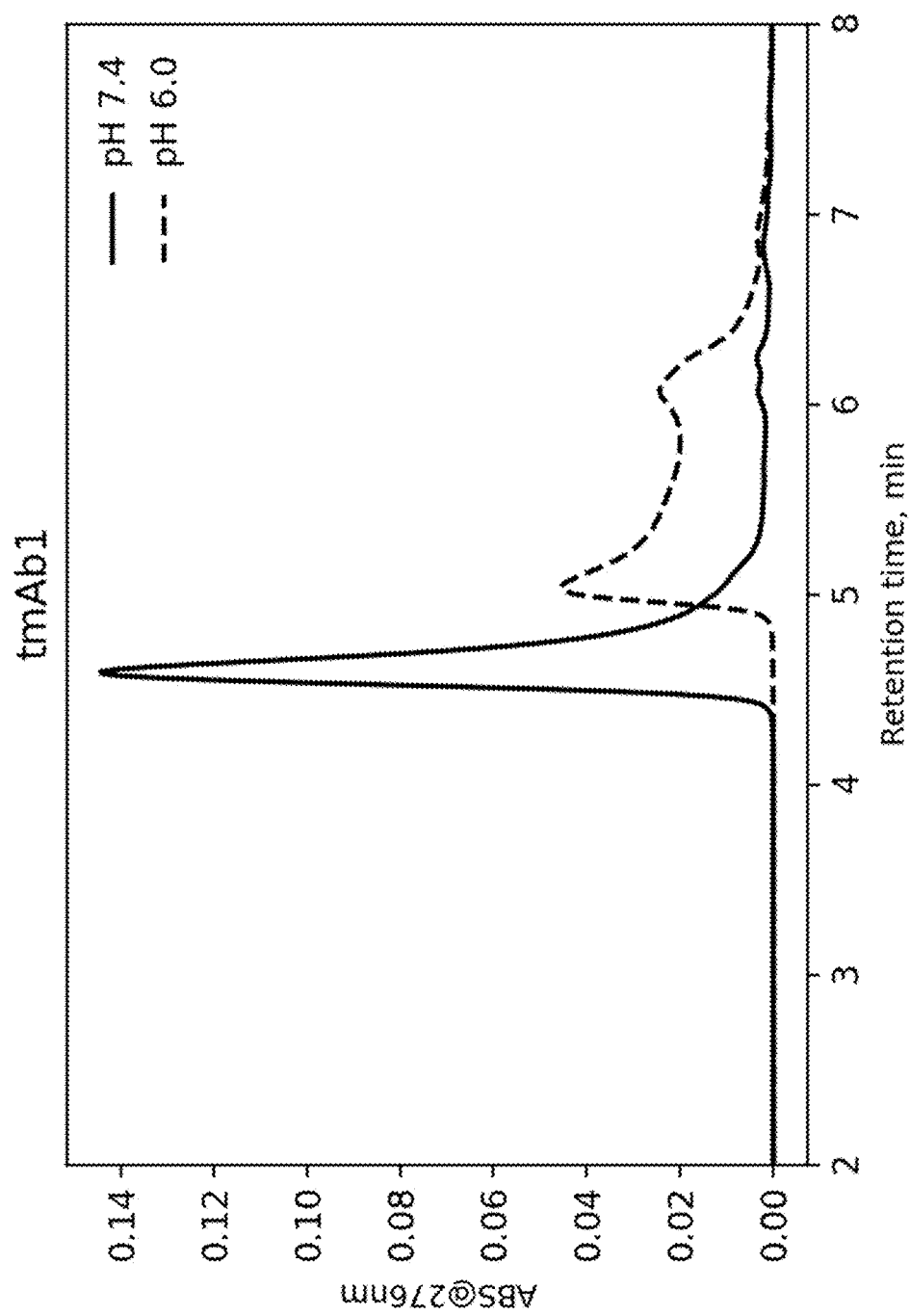
Figure 6C:
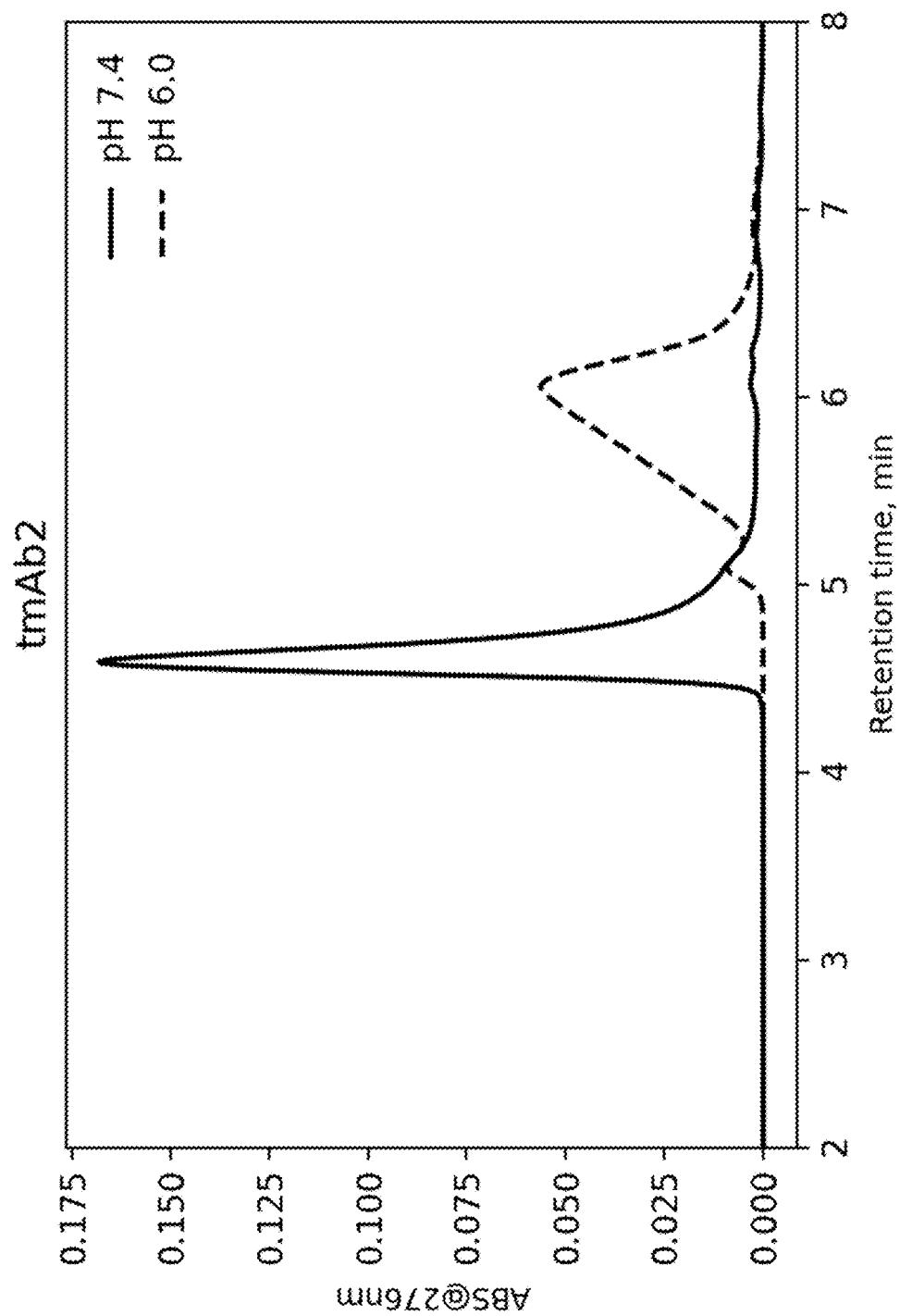
Figure 6D:
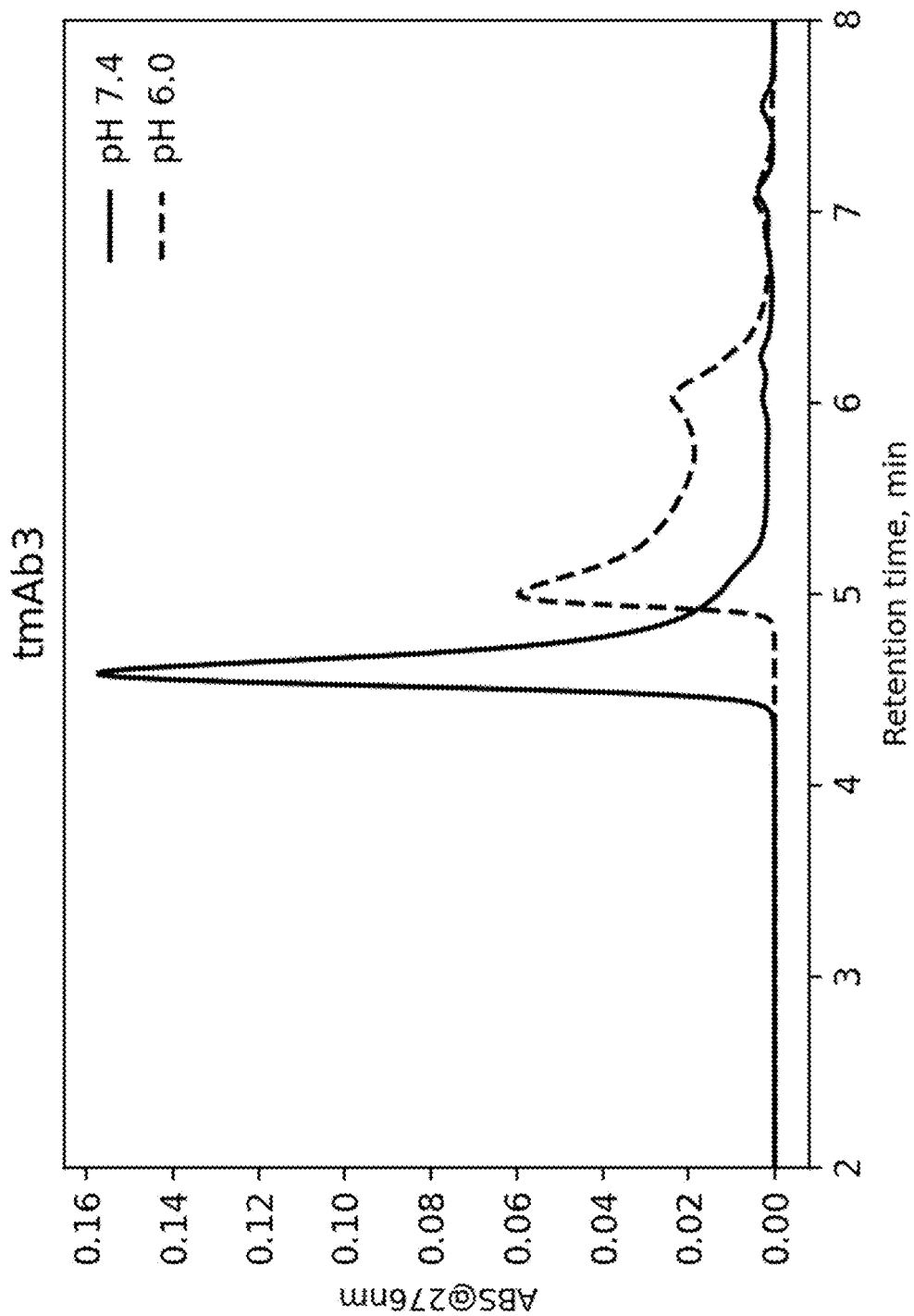

All antibodies were present in plasma in the nanomolar range, with evinacumab SIA and tmAb0.1 showing the highest exposure level staying above 200 nM throughout the study period. See FIG. 5.

Conclusion

From this study tmAb0.1 appears to be on par with evinacumab SIA in terms of TG lowering efficacy.

The results are impressive in view of tmAb0.1, tmAb0.2, tmAb0.3 and tmAb0.4 being monovalent antibodies (i.e. each having only one antagonistic ANGPTL3 binding site). Moreover, the lower exposures of tmAb0.1, tmAb0.2, tmAb0.3 and tmAb0.4 (FIG. 5) compared to evinacumab SIA show that despite the lower plasma concentrations of the monovalent antibodies, these are able to reduce the triglycerides levels in plasma to levels similar to those obtained when using evinacumab SIA.

Also, tmAb0.1, tmAb0.2, tmAb0.3 and tmAb0.4 show the capacity to remove the target ANGPTL3 in plasma. In contrast, evinacumab SIA administration resulted in an accumulation in plasma of total ANGPTL3. Combining the Fc substitutions as described herein with the Fabs of tmAb0.1-0.4, (leading to tmAb1-4) the expectation of the inventors is that the level of circulating hANGPTL3 will be significantly reduced in a human setting.

Example 6: Determination of ANGPTL3 Antibody Complexes by SE-UPLC Chromatography Immune complexes were analysed with SE-UPLC on a Waters ACQUITY UPLC System. The complexes were formed by mixing antibodies, ranging in concentration from 0.2-2.0 mg/ml, with rhANGTPL3 in 1:3 molar ratio. The antibody-antigen mixtures were equilibrated for an hour before analysis on a ACQUITY UPLC Protein BEH SEC Column, 450 Å, 2.5 μm. Each sample was injected twice, using an injection volume of 20 uL and a flow rate of 0.3 mL/min, in run buffer composed of either A) 300 mM NaCl, 10 mM Na-citrate, pH 6.0 or B) 300 mM NaCl, 10 mM TRiS/HCl, pH 7.4. The sample chamber was refrigerated at 4° C., while the column temperature was kept constant at 22° C.+/−2° C. The elution profile was monitored with UV-VIS absorption at 276 nm.

Quantification of Immune Complex Size and pH Dependent Target Binding

The size of the complex was evaluated by their retention time as well as the mean retention time (MRT), i.e., the mass midpoint of the chromatographic trace. The pH-responsiveness of the target binding, on the other hand, was evaluated by subtracting the mean retention time at pH 6.0 from the mean retention time at pH 7.4.

Results

The results from the SE-UPLC analysis are shown in FIGS. 6A-6E and in table 2 below. It is evident that the evinacumab SIA and tmAb1, tmAb2, tmAb3 and tmAb4 form immune complexes with the target antigen, rhANGTPL3. However, the evinacumab SIA forms larger and more polydisperse immune complexes compared to tmAbs1-4 (see FIGS. 6A-6E).

Moreover, as can be seen by comparing the MRT shifts in table 2, the formation of tmAb1 immune complexes is considerably more sensitive to changes in pH. Using tmAb1, the complexes are shown to be less heterogenous (more uniform) as compared to those formed by evinacumab SIA. Well-defined antibody/antigen complexes are important for increased target sweeping and antibody recycling by cellular uptake of the complexes. Having more than one binding site to the Fc receptor at the cell-surface, increases avidity and thereby increases the uptake of the complex. Furthermore, complex size and complexity is correlated with immunologic reactions which is believed to be less pronounced with smaller antibody/antigen complexes. Almost full dissociation is observed at pH6.0. The higher dissociation at pH 6.0 the better sweeping potential the antibody is believed to have. Being able to completely release the antigen when an antibody-antigen complex is being taken up by the cell is important for the sweeping behaviour of the antibodies. For the antibody being able to release the antigen and to be recycled to the circulation for continued function/binding of antigens (Igawa et al. (2016) Immun. Rev. 270:132-151).

TABLE 2

| | Retention times | | | | |
|---|---|---|---|---|---|
| | RT, min | | MRT, min | | MRT shift, min |
| Antibody | pH 6.0 | pH 7.4 | pH 6.0 | pH 7.4 | pH 7.4 -> pH 6.0 |
| evinacumab SIA | 3.83 | 3.72 | 3.82 | 3.72 | 0.10 |
| tmAb1 | 4.01 | 3.92 | 4.39 | 3.92 | 0.47 |

Retention time (RT) and mean retention time (MRT) for immune complexes eluted at pH 6.0 and pH 7.4. Listed in the rightmost column are the changes in mean retention time going from pH 7.4 to 6.0.

Example 7: Characterisation of Interaction Kinetics for Monovalent Antibodies to ANGPTL3 Proteins Binding studies were performed on a Biacore 8K (GE-Healthcare) that measures molecular interactions in real time through surface plasmon resonance. Experiments were run at 37° C. and the samples were stored at 15° C. in the sample compartment. The signal (RU, response units) reported by the Biacore is directly correlated to the mass on the individual sensor chip surfaces in four serial flow cells. Anti-HPC4 monoclonal antibody was immobilized onto both flow cells in the active channels of a C1 sensor chip according to the manufacturer's instructions. Capture of purified trimeric target protein, human ANGPTL3 (SEQ ID NO:1 residues 17-220 with a C-terminal HPC4 tag) was conducted by diluting the proteins into running buffer (20 mM tris-HCl, 150 mM NaCl, 1 mM $CaCl_2$), 0.05% v/v P20, 0.1% BSA pH 7.4 or 20 mM histidine, 150 mM NaCl, 1 mM $CaCl_2$), 0.05% v/v P20, 0.1% BSA, pH6.0) and injected over flow cell 2, creating a reference surface in flow cell 1 with only anti-HPC4 antibody immobilized. Binding of monovalent antibodies to captured target was conducted by injecting analyte (monovalent antibody) over both flow cells to allow for comparative analyses of binding of different monovalent antibodies to captured target relative to binding to the reference surface. Monovalent antibodies were diluted serially into running buffer, injected at 30 pl/min for 240 s and allowed to dissociate for 300s. The C1 surface was regenerated after each injection cycle of analyte via injection of 20 mM Tris, 150 mM NaCl, 50 mM EDTA, 0.05% P20, pH7.4. This regeneration step removed the captured target and any bound monovalent antibody from the immobilized capture antibody surface and allowed for the subsequent binding of the next interaction sample pair. The regeneration procedure did not remove the directly immobilized anti-HPC4 capture antibody from the chip surface.

Binding affinity between monovalent antibody and the target was quantified by determination of the equilibrium dissociation constant ($K_D$) determined by measurement of the kinetics of complex formation and dissociation. The rate constants corresponding to the association and the dissociation of a monovalent complex such as $k_a$ (association rate) and $k_d$ (dissociation rate) were retrieved by global fitting data to 1:1 Langmuir model with local Rmax using the Biacore evaluation software for data analysis. $K_D$ is related to $k_a$ and $k_d$ through the equation $K_D=k_d/k_a$.

Binding curves were processed by double referencing (subtraction of reference surface signals as well as blank buffer injections over captured bispecific proteins prior to data analysis). This allowed correction for instrument noise, bulk shift and drift during sample injections.

Table 3 shows the results from measurements of binding constants $K_D$ (equilibrium dissociation constant) for the interaction of human ANGPTL3 with tmAbs1-4. The calculated ratio of $K_D$ is expressed as value at pH6.0/value at pH7.4.

When introducing a HC G26D mutation to tmAb1 (resulting in tmAb2), $K_D$ increased 2-fold driven by a slower on-rate. Weaker binding at pH7.4 was associated with a weaker binding at pH6.0. All listed variants were characterised by being too low to be measured or by a low (µM range) affinity at pH6.0.

TABLE 3

$K_D$ values and ratios

| Compound ID | pH 7.4 $K_D$ (M) | pH 6.0 $K_D$ (M) | $K_D$ pH 6.0/$K_D$ pH 7.4 ratio |
|---|---|---|---|
| tmAb1 | 2.1E-08 | 2.0E-06 | 95 |
| tmAb2 | 4.3E-08 | n.d. | >100 |
| tmAb3 | 1.8E-08 | 3.0E-06 | 166 |
| tmAb4 | 5.6E-08 | n.d. | >100 | n.d. Affinity could not be determined by the SPR-assay.

Example 8: The Monovalent Format Reduces Self-Association

It is important that antibodies have a low self-association tendency across a broad pH interval, to ensure successful development of bioprocessing steps and formulation. Here the self-association of tmAb1 and the bivalent form thereof designated "mAb1" were evaluated to investigate the effect of changing antibody format from bivalent to monovalent.

Materials and Methods tmAb1 and mAb1 were prepared at 40 mg/ml concentration in 10 mM L-histidine, 10 mM NaCl, pH 6.0 as initial protein stock solutions. Protein stock solutions were mixed 1:1 (10 µl protein stock: 10 µl pH screen) with pH screen stock to reach final pH values of 3.3, 3.7, 4.2, 5.2, 5.6, 6.0, 6.4, 6.9, 7.2, 7.5, 8.1, 8.4 and a final protein concentration of 20 mg/ml. pH screen stock solutions consist of 70 mM succinic acid, 70 mM L-histidine adjusted to pH of interest. Protein stock solution and pH screen stock solutions are mixed in a 384 well plate (corning 3540), sealed with transparent plastic film and incubated over night at room temperature and away from light. Hereafter, the plate is centrifuged for 5 min at 1400 rpm (corresponding to 169×g) and then analysed with a dynamic light scattering (DLS) plate reader (Wyatt DynaPro) with an acquisition time of 5 seconds and a 40 acquisitions per sample. The hydrodynamic radius ($R_h$) is derived using the instrument software and plotted as a function of pH (see also Dingfelder et al. (2022) In: Houen G. (eds) Therapeutic Antibodies. Methods in Molecular Biology, vol 2313. Humana, New York, NY).

Results and Discussion

The increase in hydrodynamic radius ($R_h$) of mAb1 suggest that it has an extraordinarily high self-association which is likely to compromise further development of this molecule. In particular, in the pH range from pH 6.4 to 8.4, a pronounced increase in $R_h$ is observed, which could potentially also lead to issues in vivo. By changing the molecular format from the bivalent to monovalent form, a dramatic decrease in the self-association tendency was observed with only subtle increase at pH 6.4 to 8.4. The subtle increase in self-association of tmAb1 is considered to be low and acceptable. See table 4 and FIG. 7. The data supports that a highly concentrated compositions (formulations) suitable for subcutaneous administration can be prepared.

TABLE 4

Hydrodynamic radius ($R_h$) of tmAb1 and mAb at varying pH values

| pH | $R_h$ of tmAb1 (nm) | $R_h$ of mAb1 (nm) |
|---|---|---|
| 3.3 | 5.6 | 5.5 |
| 3.7 | 3.9 | 4.2 |
| 4.2 | 4.4 | 4.8 |
| 5.2 | 5.9 | 6.9 |
| 5.6 | 6.0 | 7.8 |
| 6.0 | 6.4 | 8.3 |
| 6.4 | 6.9 | 10.1 |
| 6.9 | 7.8 | 12.5 |
| 7.2 | 7.9 | 15.4 |
| 7.5 | 8.2 | 17.8 |
| 8.1 | 8.7 | 13.9 |
| 8.4 | 7.9 | 15.6 |

Example 9: The Monovalent Format Reduces Gel Formation

High physical stability at high protein concentration (50-175 mg/ml) is typically important for the successful development of antibodies as pharmaceuticals. This is required during many steps in development including the final steps of the purification process, the formulation process and for subcutaneous administration. Here we evaluate the physical stability at high protein concentrations at physiological pH at low and high ionic strength.

Materials and Methods tmAb1 and the bivalent form thereof designated "mAb1" were buffer exchanged to high ionic strength formulation (20 mM Hepes, 150 mM NaCl, pH 7.4) and low ionic strength formulation (20 mM Hepes, pH 7.4). Hereafter the samples were concentrated in Amicon 30 kDa centrifugal spin filters at room temperature with the aim of reaching 70 mg/ml. Protein concentration was determined with absorbance at 280 nm.

Figure 8:
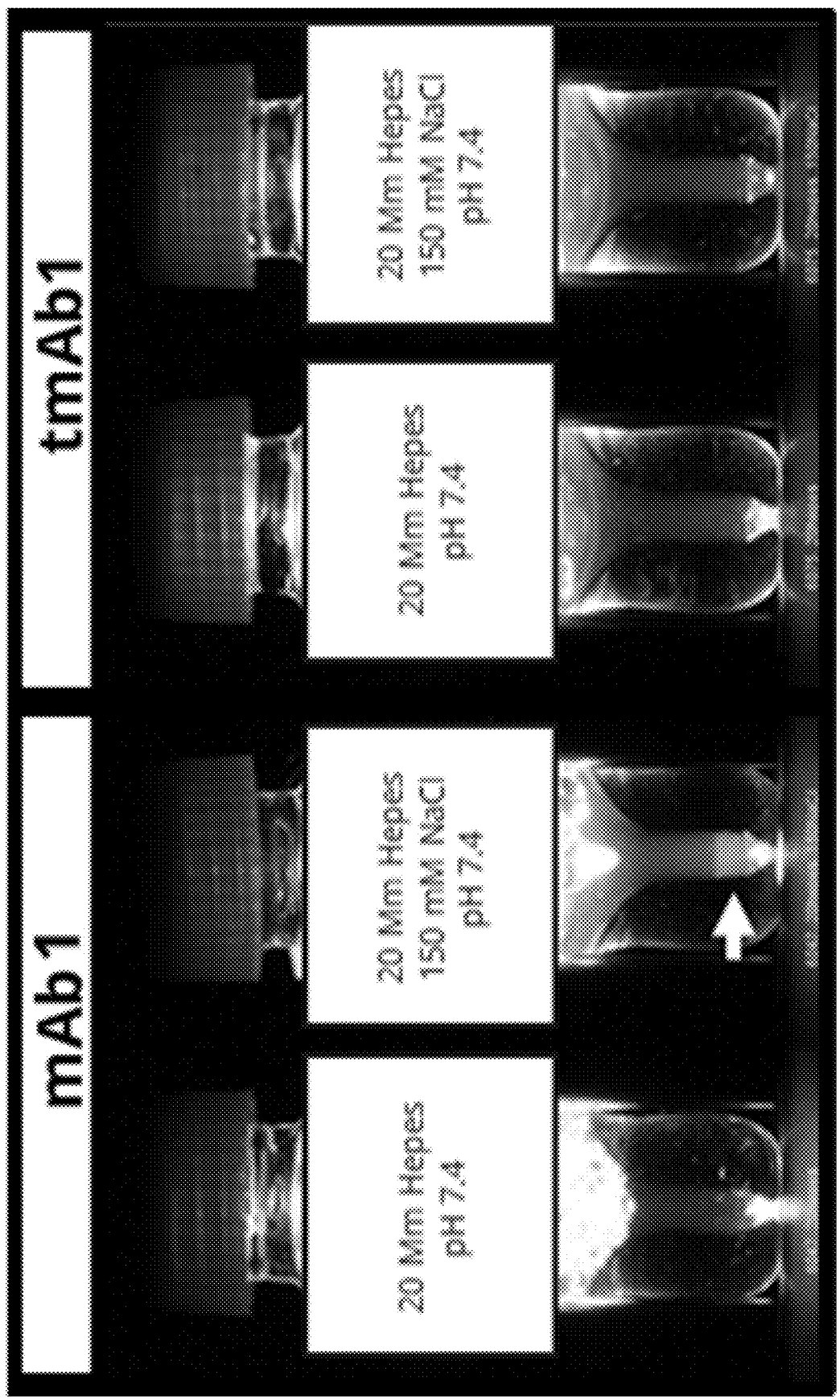
FIG. 8 shows pictures of mAb1 and tmAb1 in high- and low ionic strength formulations. Gel formation is observed for mAb1 (bivalent) post-concentration at high ionic strength (see white arrow).

Results and Discussion tmAb1 was easily concentrated to 70 mg/ml, for mAb1 (bivalent), however, it was not possible to concentrate to higher than 30 mg/ml in the high ionic strength formulation. As observed visually for mAb1, gel formation in the high ionic strength formulation resulted in phase separation, preventing the concentration to formulation relevant concentrations. See FIG. 8.

The data support that a highly concentrated formulation suitable for subcutaneous administration can be prepared, wherein the concentration of monovalent antibody tmAb1 or antigen-binding fragment thereof can be 70 mg/ml or more.

Example 10: The Monovalent Format Reduces Viscosity

Low solution viscosity of antibody solutions is critical for the final production steps, formulation, and subcutaneous administration. Here we evaluate the effect of changing from bivalent format (mAb1) to monovalent format (tmAb1) on the solution viscosity.

Materials and Methods tmAb1 and mAb1 were buffer exchanged to high ionic strength formulation (20 mM Hepes, 150 mM NaCl, pH 7.4) and low ionic strength formulation (20 mM Hepes, pH 7.4). Hereafter the samples were concentrated in Amicon 30 kDa centrifugal spin filters at room temperature with a target of 70 mg/ml.

Viscosity was measured using a Rheosense Initium instrument using 50 µl sample, a temperature of 5° C. No shear effect was observed when testing from 1.000-10.000 1/s shear suggesting Newtonian solutions, so a single shear rate of 5.000 1/s was used for comparison.

Results and Discussion

In the low ionic strength formulation, mAb1 has a high viscosity of 10.2 mPa*s whereas tmAb1 has a significant lower viscosity of 6.6 mPa*s (see table 5). In the high ionic strength formulation, tmAb1 has a similar viscosity of 5.8 mPa*s suggesting limited effect of the ionic strength of the formulation. However, for mAb1 it was not possible to concentrate to higher than 30 mg/ml in the high ionic strength formulation as gel formation resulted in phase separation as observed visually.

The results demonstrate how the poor properties of high concentration mAb1 solution can be rescued by changing from a bivalent to monovalent antibody format. mAb1 is considered to be undruggable, whereas tmAb1 has good and acceptable biophysical properties supporting that a highly concentrated formulation suitable for subcutaneous administration can be prepared.

TABLE 5

Viscosity of tmAb1 and mAb at 5° C. using a shear of 5000 1/s

| Formulation | tmAb1, 69 mg/ml | mAb1, 56 mg/ml |
|---|---|---|
| 20 mM Hepes, pH 7.4 | 6.6 mPa*s | 10.2 mPa*s |
| 20 mM Hepes, 150 mM NaCl, pH 7.4 | 5.8 mPa*s | Gel formation |

Example 11: In Vivo Evaluation of tmAb1 in Healthy Cynomolgus Monkeys

The aim of the present study was to determine the pharmacokinetics and the effect on triglycerides, of the anti-ANGPTL3 monoclonal antibody, tmAb1.

tmAb1 was administered at three different dose levels (0.3, 3, and 30 mg/kg) to normolipidemic cynomolgus monkeys as a single intravenous bolus injection. The injection volume was 0.3 mL/kg. All animals were naïve to administration of therapeutic antibodies and other protein-based therapeutics.

Blood Sampling and Sample Analysis:

Blood samples (0.5 mL) were taken from all animals at the following time-points: pre-dose, 10 min, 30 min, 1, 2, 4, 8, 14, 24, 48, 72, 96, 120, 144, 168, 192 and 240 hours (h) post dose. The blood was taken from the femoral vein and collected into Teklab $K_3$EDTA tubes (part No 3K200PP), containing 1.75 mg of EDTA/mL blood. Samples were mixed thoroughly by inversion and immediately placed on wet ice for a maximum of 30 minutes prior to centrifugation. The samples were centrifuged at approximately 2000 g for 10 minutes at 2-8° C., and plasma aliquots were transferred to Micronic tubes (cat. no. MP32022).

The samples were analysed to quantify tmAb1 and triglyceride concentrations.

Triglycerides

Triglycerides were measured on a COBAS 6000 multi-analyser according to the manufacturer's recommendation (Roche Diagnostics).

Human IgG Measurements (tmAb1), Principle of Assay:

Plasma samples were analysed for anti-ANGPTL3 hIgG (tmAb1) using Luminescence Oxygen Channeling Immunoassay (LOCI). The donor beads were coated with streptavidin, while acceptor beads were conjugated with an in-house monoclonal mouse anti-human IgG not cross-binding to cynomolgus IgG. A biotinylated recombinant antibody fragment (nanobody/$V_H$H) cross-binding to human IgG-Fc (not cynomolgus) is from ThermoFisher (CaptureSelect, cat:7103322500). The three reactants (donor beads with streptavidin, acceptor beads conjugated with target-specific Ab, and a biotinylated target-specific antibody fragment) were combined with the anti-ANGPTL3 antibodies (hIgG) such to form a two-sited immuno-complex. Illumination of the complex release singlet oxygen atoms from the donor beads. They are channelled into the acceptor beads and triggers chemiluminescence, which is measured by an EnVision plate reader (PerkinElmer) according to manufacturer instructions. The amount of light is proportional to the concentration of the anti-ANGPTL3 antibody (tmAb1).

Human IgG Measurements (tmAb1), Assay Procedure:

Two µL of plasma sample/calibrator/control were applied to the wells of 384-well LOCI plates followed by a 15 µL mixture of acceptor beads (0.5 µg/well) coated with MAb anti-hIgG and biotinylated antibody fragment. The plates were incubated for 1 h at room temperature (RT). Then 30 µL streptavidin-coated donor-beads (2 pg/well) were added to each well and incubated for 30 min at RT. The plates were read in an Envision plate reader at 21-22° C. with a filter having a bandwidth of 520-645 nm after excitation by a 680 nm laser. The total measurement time per well was 210 ms including a 70 ms excitation time. The calibrator material was tmAb1 diluted in PBS+1% cynomolgus plasma. The assay range spans from 11-20.000 pM. The cynomolgus samples were tested diluted 100× in PBS plasma. Samples measured above Upper Limit of Quantification (ULOQ) were diluted further in PBS+1% cynomolgus plasma.

Results

PK

Figure 9:
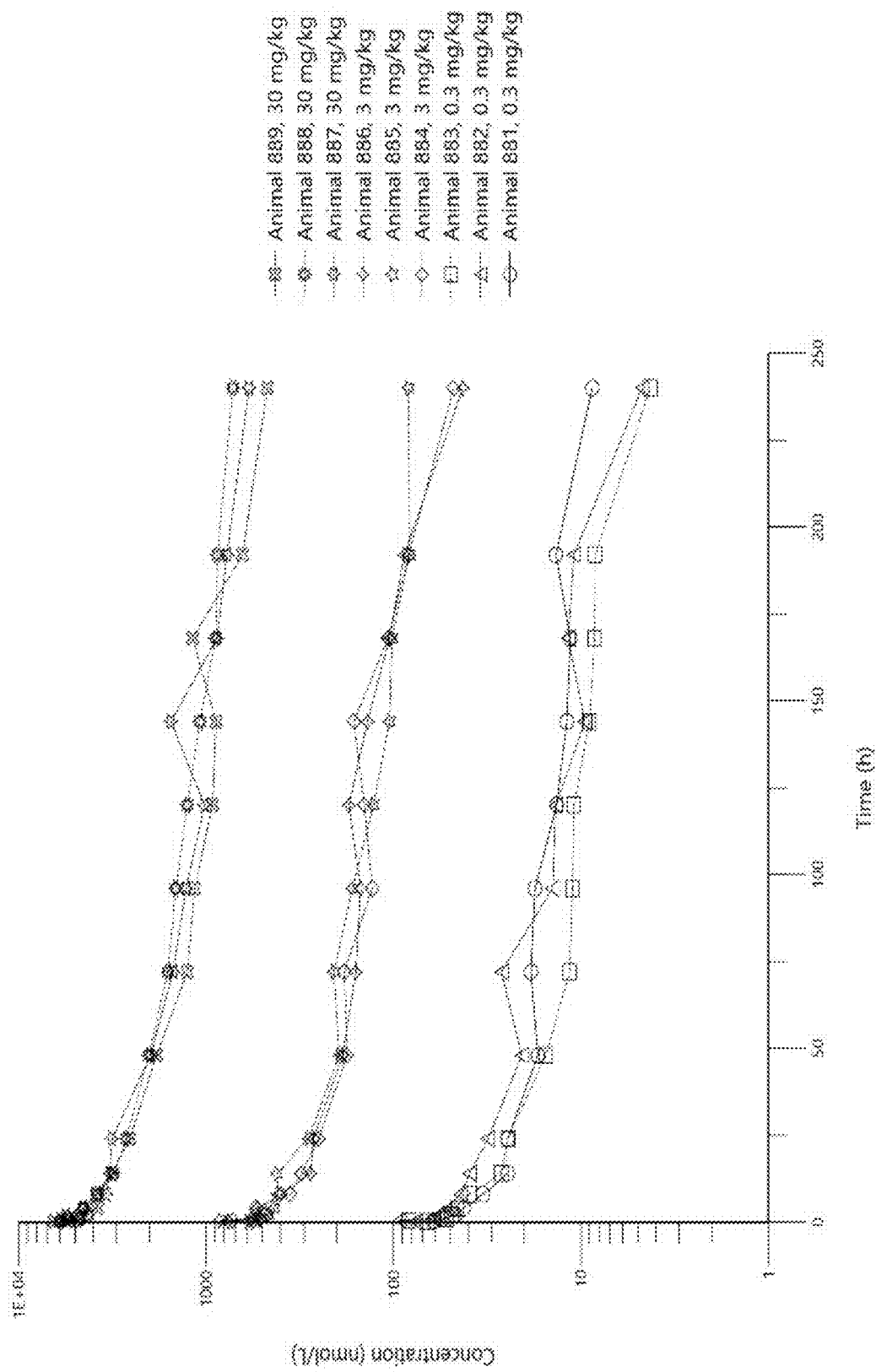
FIG. 9 shows levels of tmAb1 in plasma samples from cynomolgus monkeys.

The pharmacokinetics (PK) of tmAb1 are shown in FIG. 9. The PK appears linear at all dose levels for 240h, with signs of extensive non-linearity across all dose-levels.

The half-life calculated using non-compartmental analysis and the "linear-up log-down" method, was in the range of 90.9-171 for all animals, with geometric means of 119, 107, and 107 hours for the 0.3, 3, and 30 mg/kg groups, respectively, based on observations for 240h.

TG

Figure 10:
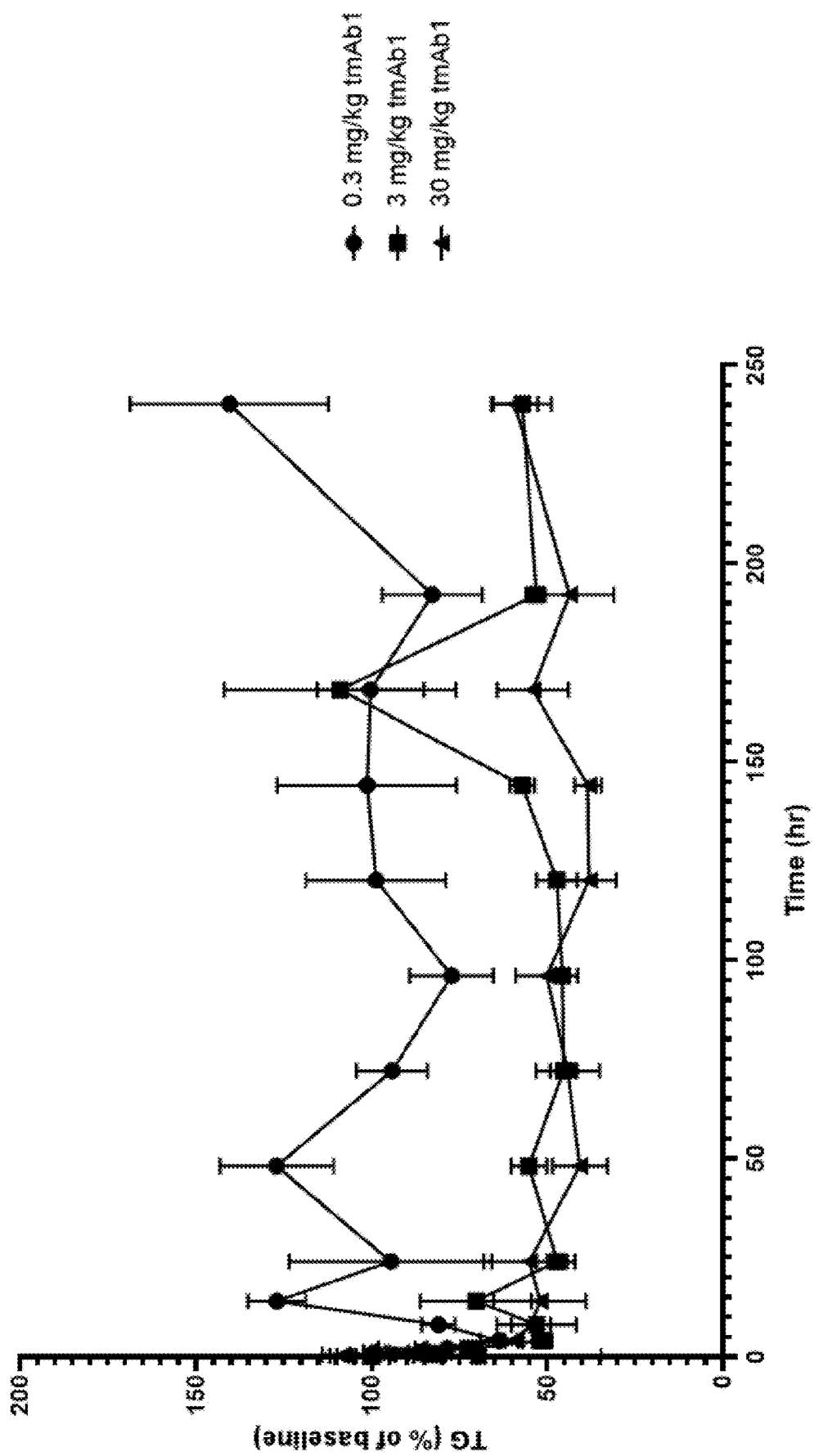
FIG. 10 shows levels of triglycerides in plasma samples from cynomolgus monkeys, administered with tmAb1 in three different doses.

The effect on TG was evaluated during the period 0-240h (FIG. 10). The 3 mg/kg and 30 mg/kg provided a rapid decrease in TG levels, with around 40-50% reduction after 4 hours. The maximal reduction seen during the study varied between 56-78%. In general, the effect on TG persisted for at least 240h. At the 0.3 mg/kg dose level, there is a transient effect seen of between 28-44% on the TG levels, after 4 hours and after 12 hours the TG levels are back to baseline levels.

Example 12: tmAb2, tmAb3, tmAb4 Generation

CDR single site mutagenesis libraries of the variable domain sequences of tmAb1 were generated to explore possibilities for further modulation of pH dependent target binding (see Examples 6 and 7) and LPL activity (Example 4). The best performing molecules were evaluated as tmAbs wrt. the effect on formulation (Example 8, 9 and 10), activity and target binding parameters (Example 4 and 7), IC formation (Example 6) and in vivo effector function (Example 5) resulting in selection of tmAb2, tmAb3 and tmAb4.

The invention claimed is:

1. A monovalent antibody or antigen-binding fragment thereof capable of binding human ANGPTL3 (hANGPTL3) (SEQ ID NO:1),
   wherein
   a) the heavy chain of said antibody or antigen-binding fragment thereof comprises:
      a CDR1 sequence of amino acid residues SYWMT (SEQ ID NO:2), and
      a CDR2 sequence of amino acid residues SISSHSTYIYYADSVKG (SEQ ID NO:3), and
      a CDR3 sequence of amino acid residues EGWYDNWFDP (SEQ ID NO:4); or
   b) the heavy chain of said antibody or antigen-binding fragment thereof comprises:
      a CDR1 sequence of amino acid residues SYWMT (SEQ ID NO:24), and
      a CDR2 sequence of amino acid residues SISSHSTYIYYADSVKG (SEQ ID NO:25), and
      a CDR3 sequence of amino acid residues EGWYDNWNDP (SEQ ID NO:26),
   and
   wherein the light chain of said antibody or antigen-binding fragment thereof comprises:
      a CDR1 sequence of amino acid residues RASQNIRSPYLA (SEQ ID NO:9), and
      a CDR2 sequence of amino acid residues GVSSRAA (SEQ ID NO:10), and
      a CDR3 sequence of amino acid residues QQYDDHPYT (SEQ ID NO:11).

2. The monovalent antibody or antigen-binding fragment thereof according to claim 1, wherein the heavy chain of said monovalent antibody or antigen-binding fragment thereof comprises:
   a CDR1 sequence of amino acid residues SYWMT (SEQ ID NO:2),
   a CDR2 sequence of amino acid residues SISSHSTYIYYADSVKG (SEQ ID NO:3), and
   a CDR3 sequence of amino acid residues EGWYDNWFDP (SEQ ID NO:4).

3. The monovalent antibody or antigen-binding fragment thereof according to claim 1, wherein the heavy chain of said monovalent antibody or antigen-binding fragment thereof comprises:
   a CDR1 sequence of amino acid residues SYWMT (SEQ ID NO:24),
   a CDR2 sequence of amino acid residues SISSHSTYIYYADSVKG (SEQ ID NO:25), and
   a CDR3 sequence of amino acid residues EGWYDNWNDP (SEQ ID NO:26).

4. The monovalent antibody or antigen-binding fragment thereof according to claim 1, wherein the heavy chain variable domain has at least 95, 96, 97, 98 or 99% identity to SEQ ID NO:5, and the light chain variable domain has at least 95, 96, 97, 98 or 99% identity to SEQ ID NO:12.

5. The monovalent antibody or antigen-binding fragment thereof according to claim 1, wherein
   a) the heavy chain variable domain comprises SEQ ID NO:5 and the light chain variable domain comprises SEQ ID NO:12, or
   b) the heavy chain variable domain comprises SEQ ID NO:17 and the light chain variable domain comprises SEQ ID NO:12, or
   c) the heavy chain variable domain comprises SEQ ID NO:22 and the light chain variable domain comprises SEQ ID NO:12, or
   d) the heavy chain variable domain comprises SEQ ID NO:27 and the light chain variable domain comprises SEQ ID NO:12.

6. The monovalent antibody or antigen-binding fragment thereof according to claim 1, wherein said monovalent antibody or antigen-binding fragment thereof comprises
   tyrosine (Y) in position 252,
   threonine (T) in position 254, and
   glutamate (E) in position 256,
   in the heavy chain(s) (EU residues).

7. The monovalent antibody or antigen-binding fragment thereof according to claim 1, wherein said monovalent antibody or antigen-binding fragment thereof comprises one or more of
   tyrosine (Y) in position 234,
   aspartate (D) in position 238,
   valine (V) in position 250,
   isoleucine (I) in position 264,
   proline (P) in position 307, and/or
   lysine (K) in position 330,
   in the heavy chain(s) (EU residues).

8. The monovalent antibody or antigen-binding fragment thereof according to claim 1, wherein said monovalent antibody or antigen-binding fragment thereof comprises arginine (R) in positions 311 and 343 in the heavy chain(s) (EU residue).

9. The monovalent antibody or antigen-binding fragment thereof according to claim 1 wherein said monovalent antibody or antigen-binding fragment thereof is an antagonist capable of inhibiting hANGPTL3-mediated inhibition of Lipoprotein lipase (LPL) and capable of reducing the concentration of hANGPTL3 in human plasma.

10. The monovalent antibody or antigen-binding fragment thereof according to claim 1, comprising an Fc region.

11. The monovalent antibody or antigen-binding fragment thereof according to claim 1 wherein the isotype of said monovalent antibody is based on IgG1, IgG2, IgG3 or IgG4.

12. A monovalent antibody or antigen-binding fragment thereof capable of binding human ANGPTL3 (hANGPTL3) (SEQ ID NO:1), comprising a heavy chain, a truncated heavy chain and a light chain,
   wherein the heavy chain comprises SEQ ID NO:6, the truncated heavy chain comprises SEQ ID NO:7 and the light chain comprises SEQ ID NO:13.

13. A pharmaceutical composition comprising the monovalent antibody or antigen-binding fragment thereof according to claim 1 and one or more pharmaceutically acceptable carrier(s).

14. A pharmaceutical composition comprising the monovalent antibody or antigen-binding fragment thereof according to claim 12 and one or more pharmaceutically acceptable carrier(s).

15. A method of treating elevated triglyceride concentration in human plasma, comprising administering the pharmaceutical composition of claim 13 to a patient in need thereof.

16. A method of treating elevated triglyceride concentration in human plasma, comprising administering the pharmaceutical composition of claim 14 to a patient in need thereof.

17. A method of treating atherosclerotic cardiovascular disease (ASCVD), comprising administering the pharmaceutical composition of claim 13 to a patient in need thereof.

18. A method of treating atherosclerotic cardiovascular disease (ASCVD), comprising administering the pharmaceutical composition of claim 14 to a patient in need thereof.

19. The method according to claim 15, wherein the composition is administered subcutaneously.

20. The method according to claim 16, wherein the composition is administered subcutaneously.

21. The method according to claim 17, wherein the composition is administered subcutaneously.

22. The method according to claim 18, wherein the composition is administered subcutaneously.

23. A kit comprising the monovalent antibody or antigen-binding fragment thereof according to claim 1, and instructions for use.

24. A kit comprising the monovalent antibody or antigen-binding fragment thereof according to claim 12, and instructions for use.

* * * * *

UNITED STATES PATENT AND TRADEMARK OFFICE
CERTIFICATE OF CORRECTION

| | | |
|---|---|---|
| PATENT NO. | : 11,780,910 B1 | Page 1 of 1 |
| APPLICATION NO. | : 18/142242 | |
| DATED | : October 10, 2023 | |
| INVENTOR(S) | : Anette Henriksen et al. | |

It is certified that error appears in the above-identified patent and that said Letters Patent is hereby corrected as shown below:

On the Title Page

At Column 1, item (54), please amend as follows: "NOVEL ANTI-ANGPTL3 ANTIBODIES SUITABLE FOR HIGH CONCENTRATION COMPOSITIONS AND SUBCUTANEOUS ADMINISTRATION"

In the Specification

At Column 1, Line number 1-4, please amend as follows: "NOVEL ANTI-ANGPTL3 ANTIBODIES SUITABLE FOR HIGH CONCENTRATION COMPOSITIONS AND SUBCUTANEOUS ADMINISTRATION"

Signed and Sealed this
Twenty-seventh Day of August, 2024

Katherine Kelly Vidal
*Director of the United States Patent and Trademark Office*